US006183976B1

(12) United States Patent
Reed et al.

(10) Patent No.: US 6,183,976 B1
(45) Date of Patent: Feb. 6, 2001

(54) **COMPOUNDS AND METHODS FOR THE DIAGNOSIS AND TREATMENT OF *B. MICROTI* INFECTION**

(75) Inventors: Steven G. Reed, Bellevue; Michael J. Lodes, Seattle; Raymond Houghton, Bothell; Paul R. Sleath, Seattle, all of WA (US)

(73) Assignee: Corixa Corporation, Seattle, WA (US)

( * ) Notice: Under 35 U.S.C. 154(b), the term of this patent shall be extended for 0 days.

(21) Appl. No.: 08/845,258

(22) Filed: Apr. 24, 1997

Related U.S. Application Data

(63) Continuation-in-part of application No. 08/723,142, filed on Oct. 1, 1996.

(51) Int. Cl.[7] ........................ C07K 14/44; G01N 33/569; A61K 39/018

(52) U.S. Cl. ........................ 435/7.22; 530/350; 530/822; 424/191.1; 424/270.1

(58) Field of Search ........................ 435/7.22; 424/191.1, 424/270.1; 530/350, 822

(56) References Cited

U.S. PATENT DOCUMENTS

| | | | |
|---|---|---|---|
| 4,879,213 | 11/1989 | Fox et al. | 435/5 |
| 5,171,685 | 12/1992 | McElwain et al. | 435/252.33 |

FOREIGN PATENT DOCUMENTS

WO 90/11776 10/1990 (WO) .

OTHER PUBLICATIONS

Tetzlaff, C.L. et al. Molecular and Biochemical Parasitology 40:183–192, 1990.*

Burgess et al., "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue," *The Journal of Cell Biology* 111: 2129–2138, 1990.

Foglino et al., "Nucleotide sequence of the *pepN* gene encoding aminopeptidase N of *Escherichia coli,* " *Gene* 49: 303–309, 1986.

Lazar et al., "Transforming Growth Factor α: Mutation of Aspartic Acid 47 Leucine 48 Results in Different Biological Activities," *Molecular and Cellular Biology* 8(3): 1247–1252, 1988.

McCaman and Gabe, "The nucleotide sequence of the *pepN* gene and its over–expression in *Escherichia coli,* " *Gene* 48: 145–153, 1986.

Plotkin et al., *Vaccines*, W.B. Saunders Company, Philadelphia, 1988, Chapter 29, p. 571 ($2^{nd}$ full paragraph).

* cited by examiner

*Primary Examiner*—Mary E. Mosher
(74) *Attorney, Agent, or Firm*—Seed Intellectual Property Law Group PLLC

(57) ABSTRACT

Compounds and methods for the diagnosis and treatment of *B. microti* infection are disclosed. The compounds provided include polypeptides that contain at least one antigenic portion of a *B. microti* antigen and DNA sequences encoding such polypeptides. Antigenic epitopes of such antigens are also provided, together with pharmaceutical compositions and vaccines comprising such polypeptides, DNA sequences or antigenic epitopes. Diagnostic kits containing such polypeptides, DNA sequences or antigenic epitopes and a suitable detection reagent may be used for the detection of *B. microti* infection in patients and biological samples. Antibodies directed against such polypeptides and antigenic epitopes are also provided.

11 Claims, 7 Drawing Sheets

```
AACTAGATGCAGCACCACAATCACTACCACGTACCAATCATATACCAATAATGTACTAATAATGTACCAATAACTATGGTTTATAAAGATGGTGTCATTTAAATCAATATTAGTTCCTTATATTA   125
                                                                      M  V  S  F  K  S  I  L  V  P  Y  I

CACTCTTTTTAATGAGCGGTGCTGTCTTTGCAAGTGATACCGATCCCGAAGCTGGTGGGCCTAGTGAAGCTGGTGGGCCTAGTGGAACTGTTGGGCCCAGTGAAGCTGGTGGGCCTAGTGAAGCT   250
                                                                  Repeat Sequences
 T  L  F  L  M  S  G  A  V  F  A  S  D  T  D  P  E  A  G  G  P  S  E  A  G  G  P  S  G  T  V  G  P  S  E  A  G  G  P  S  E  A GGTGGGCCTAGTGGAACTGGTTGGCCTAGTGAAGCTGGTGGGCCTAGTGAAGCTGGTGGGCCTAGTGAAGCTGGTGGGCCTAGTGGAACTGGTTGGCCTAGTGGAAC   375
                                              Repeat Sequences
 G  G  P  S  G  T  G  W  P  S  E  A  G  G  P  S  E  A  G  G  P  S  E  A  G  G  P  S  G  T  G  W  P  S  G  T TGGTTGGCCTAGTGAAGCTGGTTGGTCTAGTGAACGATTTGGATATCAGCTTCTTCCGTATTCTAGAAGAATAGTTATATTTAATGAAGTTTGTTTATCTTATATATACAAACATAGTGTTATGA   500
      Repeat Sequences
 G  W  P  S  E  A  G  W  S  S  E  R  F  G  Y  Q  L  L  P  Y  S  R  R  I  V  I  F  N  E  V  C  L  S  Y  I  Y  K  H  S  V  M TATTGGAACGAGATAGGGTGAACGATGGTCATAAAGACTACATTGAAGAAAAAACCAAGGAGAAGAATAAATTGAAAAAAGAATTGGAAAAATGTTTTCCTGAACAATATTCCCTTATGAAGAAA   625
 I  L  E  R  D  R  V  N  D  G  H  K  D  Y  I  E  E  K  T  K  E  K  N  K  L  K  K  E  L  E  K  C  F  P  E  Q  Y  S  L  M  K  K GAAGAATTGGCTAGAATATTTGATAATGCATCCACTATCTCTTCAAAATATAAGTTATTGGTTGATGAAATATCAAACAAGGCCTATGGTACATTGGAAGGTCCAGCTGCTGATAATTTTGACCA   750
 E  E  L  A  R  I  F  D  N  A  S  T  I  S  S  K  Y  K  L  L  V  D  E  I  S  N  K  A  Y  G  T  L  E  G  P  A  A  D  N  F  D  H TTTCCGTAATATATGGAAGTCTATTGTACTTAAAGATATGTTTATATATTGTGACTTATTATTAGAACATTTAATCTATAAATTCTATTATGACAATACCGTTAATGATATCAAGAAAAATTTTG   875
 F  R  N  I  W  K  S  I  V  L  K  D  M  F  I  Y  C  D  L  L  L  Q  H  L  I  Y  K  F  Y  Y  D  N  T  V  N  D  I  K  K  N  F ACGAATCCAAATCTAAAGCTTTAGTTTTGAGGGATAAGATCACTAAAAAGGATGGAGATTATAACACTCATTTTGAGGACATGATTAAGGAGTTGAATAGTGCAGCAGAAGAATTTAATAAAATT   1000
 D  E  S  K  S  K  A  L  V  L  R  D  K  I  T  K  K  D  G  D  Y  N  T  H  F  E  D  M  I  K  E  L  N  S  A  A  E  E  F  N  K  I GTTGACATCATGATTTCCAACATTGGGGATTATGATGAGTATGACAGTATTGCAAGTTTCAAACCATTTCTTTCAATGATCACCGAAATCACTAAAATCACCAAAGTTTCTAATGTAATAATTCC   1125
 V  D  I  M  I  S  N  I  G  D  Y  D  E  Y  D  S  I  A  S  F  K  P  F  L  S  M  I  T  E  I  T  K  I  T  K  V  S  N  V  I  I  P TGGAATTAAGGCACTAACTTTAACCGTTTTTTTAATATTTATTACAAAATAGATGTAATACCAGATGTATACATTATTATATATTACAAAATTTACACATTATTTATGTATGAACGAACGAACAT   1250
 G  I  K  A  L  T  L  T  V  F  L  I  F  I  T  K
```

Fig. 1A

```
CTCAGTCTTAAATGAAGAAATTGGGATAAATATGGAAATAGATTAAAGTAACATGAGAAAGATGAATATAATATTAGAATATGAAATTTAACAGAAATAAAATGAAGTAAAAGAGTGTATTTTGT  1375
AATAATTTATAATAAATTAGTATACAATGATTATATTACAGATGACTATTGATTATTGTATCAATTAAATATTGATTATTAATGATATCATATATGTATATGTTAATGATTGATTTGTTATACGT  1500
TGTGAATATGTTATATAATGACATACTATAATAATTAATATAATGTAGAGGATATTTTTTTTAATAGTATTTAATGAATATTATAGTTATAATTATAATAATGTAGATAAAAATGACATTAATTT  1625
GAATGTTTAAATTGAAATGTATGTAAAAATATGTATTTATAATCTGAATTGATTAATAATATAATATTCTACAATTAATTATTTTTGTAATTATAATAATTGATTATATTAATCTTTGAATTATT  1750
ATAAATAATATTATACTTCATTAAATTATTTCACATAAATTTCCAAATTATTATCCTTTATCTTAATGTTATCCAATTTTACACATCTTTCTTCATTACAATATTTTTTTACTAATCCTGTATGC  1875
TCATATTCATATTCTTTAGAAAATATAACGAAAATTAGATGTAACTTCGCCACTTACAAGTAAACTACCATCAATATAATAATAATGAATACCATTCATGTCCGTATATTCTTTATATTTTTTATC  2000
ATATTTTATTTTGTGATTATTCCATTCATTTGTATCATTATTCAATGAGAGAAATAATAGCAGAAAGATCCTTCTATAGAAACATAAAATTCAATTAATACTGGATTATTATGTTTGCAAGTATA  2125
GATGTTTAAATCAATAACACTACCAGTTGGTAATTTAGCATTGTCATCAAATTCAATTATATAATCAGAAATTTTGATTTTATCAATTTTATTCGGATGTGATAATTTATTTTGTTCTGATTCAT  2250
CGATCATGTATACAAATACTATTGTTAAAGGTTCCCTATCCTTATAATTAAAGTGGCCAATAAGATTGGCATTAATTACATTAGTAGTGTGTATTTGTAATAGTATCATTAGTGGTACTGACA  2375
GTTGTTATAGGTTTTGATTTCCATAATGAAACATCATTTTTATCTACACAATACA  2430
```

*Fig. 1B*

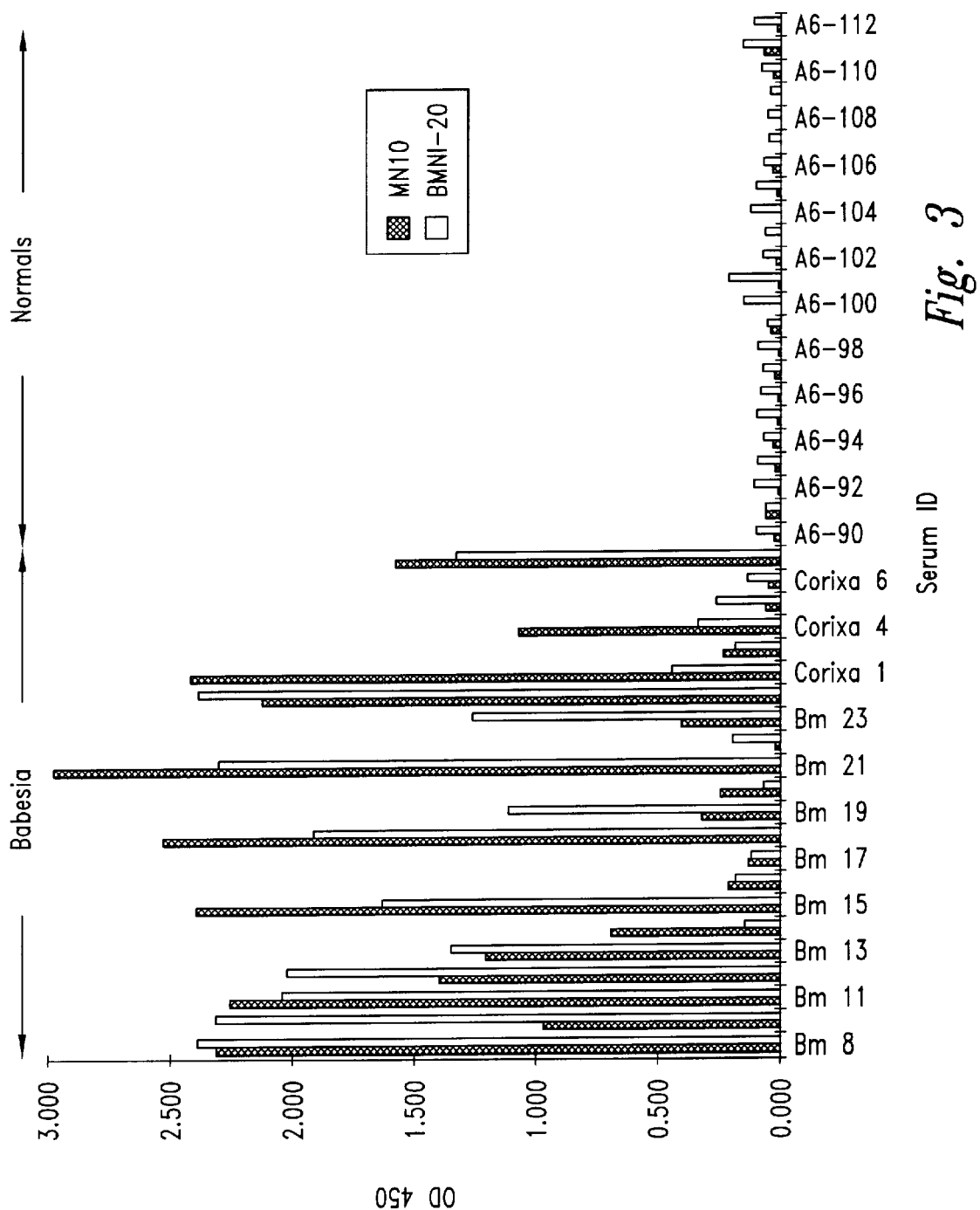

```
                           SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
          (A) LENGTH: 792 base pairs
          (B) TYPE: nucleic acid
          (C) STRANDEDNESS: single
          (D) TOPOLOGY: linear (xi) SEQUENCE DESCRIPTION: SEQ ID NO:1:

CACTCTTTTT AATGAGCGGT GCTGTCTTTG CAAGTGATAC CGATCCCGAA GCTGGTGGGC      60

CTAGTGAAGC TGGTGGGCCT AGTGGAACTG TTGGGCCCAG TGAAGCTGGT GGGCCTAGTG     120

AAGCTGGTGG GCCTAGTGGA ACTGGTTGGC CTAGTGAAGC TGGTGGGCCT AGTGAAGCTG     180

GTGGGCCTAG TGAAGCTGGT GGGCCTAGTG AAGCTGGTGG GCCTAGTGGA ACTGGTTGGC     240

CTAGTGGAAC TGGTTGGCCT AGTGAAGCTG GTTGGTCTAG TGAACGATTT GGATATCAGC     300

TTCTTCCGTA TTCTAGAAGA ATAGTTATAT TTAATGAAGT TTGTTTATCT TATATATACA     360

AACATAGTGT TATGATATTG GAACGAGATA GGGTGAACGA TGGTCATAAA GACTACATTG     420

AAGAAAAAAC CAAGGAGAAG AATAAATTGA AAAAAGAATT GGAAAAATGT TTTCCTGAAC     480

AATATTCCCT TATGAAGAAA GAAGAATTGG CTAGAATATT TGATAATGCA TCCACTATCT     540

CTTCAAAATA TAAGTTATTG GTTGATGAAA TATCAAACAA GGCCTATGGT ACATTGGAAG     600

GTCCAGCTGC TGATAATTTT GACCATTTCC GTAATATATG GAAGTCTATT GTACTTAAAG     660

ATATGTTTAT ATATTGTGAC TTATTATTAC AACATTTAAT CTATAAATTC TATTATGACA     720

ATACCGTTAA TGATATCAAG AAAAATTTTG ACGAATCCAA ATCTAAAGCT TTAGTTTTGA     780

GGGATAAGAT CA                                                        792

(2) INFORMATION FOR SEQ ID NO:2:

(i) SEQUENCE CHARACTERISTICS:
```

(A) LENGTH: 2732 base pairs
(B) TYPE: nucleic acid
(C) STRANDEDNESS: single
(D) TOPOLOGY: linear (xi) SEQUENCE DESCRIPTION: SEQ ID NO:2:

```
AAACCCTAAA CCCTAAACCC TAAACCCTAA ACCCTAAACC CCTAAACCCT AAACCCTAAA      60
CCCTAAACCC TAAACCCTAA AACCCTAAAC CCTAAACCCT AAACCCTAAA CCCTAAACCC     120
TAAACCCTAA ACCCTAAACC CTAAACCCTA ACCCTAAACC CTAAACCCT AAACCCTAAA      180
CCCTAAACCC TAAACCCTAA ACCCTAAACC CTAAACCCCT AAACCCTAAA CCCTAAACCC     240
TAAACCCTAA ACCCTAAACC CTAAACCCTA ACCCTAAACC CTAAACCCT AAACCCTAAA      300
CCCTAAACCC TAAACCCTAA ACCCTAAACC CTAAAACCCT AAACCCTAAA CCCTAAACCC     360
TAAACCCTAA ACCCTAAACC CCTAAACCCT AAACCCTAAA CCCTAAACCC TAAACCCTAA     420
ACCCCTAAAC CCTAAACCCC TAAACCCTAA ACCCTAAACC CTAAACCCTA AACCCTAAAC     480
CCTAAACCCT AAACCCTAAA CCCTAAACCC TAAACCCCTA ACCCTAAAC CCTAAACCCT      540
AAACCCTAAA CCCTAAACCC TAAACCCTAA ACCCTAACCC TAACCCTAAC CCTAACCCTA     600
ACCTAGCCTT CATTGACGTC TATCCCCAAT CTTAGAAAAA TCTTCAAATC GATTCTAGAA     660
TAACTGGAAA CAATTATCAG AAATTGTATA ACTGCTTATT AGCTTATTAG CTTATTAGTT     720
AGGATGTATG CACATTGATG ACAACTAGAT GCAGCACCAC AATCACTACC ACGTACCAAT     780
CATATACCAA TAATGTACTA ATAATGTACC AATAACTATG GTTTATAAAG ATGGTGTCAT     840
TTAAATCAAT ATTAGTTCCT TATATTACAC TCTTTTTAAT GAGCGGTGCT GTCTTTGCAA     900
GTGATACCGA TCCCGAAGCT GGTGGGCCTA GTGAAGCTGG TGGGCCTAGT GGAACTGTTG     960
GGCCCAGTGA AGCTGGTGGG CCTAGTGAAG CTGGTGGGCC TAGTGGAACT GTTGGGCCCA    1020
GTGAAGCTGG TGGGCCTAGT GAAGCTGGTG GGCCTAGTGG AACTGGTTGG CCTAGTGAAG    1080
CTGGTGGGCC TAGTGAAGCT GGTGGGCCTA GTGGAACTGT TGGGCCCAGT GAAGCTGGTG    1140
GGCCTAGTGA AGCTGGTGGG CCTAGTGAAC TGGTTGGCC TAGTGAAGCT GGTGGGCCTA     1200
GTGAAGCTGG TGGGCCTAGT GAAGCTGGTG GGCCTAGTGA AGCTGGTGGG CCTAGTGGAA    1260
CTGGTTGGCC TAGTGGAACT GGTTGGCCTA GTGAAGCTGG TTGGTCTAGT GAACGATTTG    1320
GATATCAGCT TCTTCCGTAT TCTAGAAGAA TAGTTATATT TAATGAAGTT TGTTTATCTT    1380
ATATATACAA ACATAGTGTT ATGATATTGG AACGAGATAG GGTGAACGAT GGTCATAAAG    1440
ACTACATTGA AGAAAAAACC AAGGAGAAGA ATAAATTGAA AAAAGAATTG GAAAAATGTT    1500
TTCCTGAACA ATATTCCCTT ATGAAGAAAG AAGAATTGGC TAGAATATTT GATAATGCAT    1560
CCACTATCTC TTCAAAATAT AAGTTATTGG TTGATGAAAT ATCAAACAAG GCCTATGGTA    1620
CATTGGAAGG TCCAGCTGCT GATAATTTTG ACCATTTCCG TAATATATGG AAGTCTATTG    1680
TACTTAAAGA TATGTTTATA TATTGTGACT TATTATTACA ACATTTAATC TATAAATTCT    1740
ATTATGACAA TACCGTTAAT GATATCAAGA AAAATTTTGA CGAATCCTGG ACACAGACAT    1800
TAAAAGAATA AGCCTGCTTG GGGGTTTCTG GGCATCTCTT CATGAGTGCC AGTCACACAA    1860
CTCTTCTGTG AGCCTTCTAC AATAAGGACT TTGTGTGCTT CGATATTTTT TTAGACTAAA    1920
GTGAACTCTC TCCTCCACCT TTGGCTTCAG TTAGTTATTT CAAATGGCAA AAGTTATTAA    1980
AAATTCCAGT GTGGAAACTG GCTTAACCAA CAGGAAAGGG GTTTTGAGGT CGCATCACTA    2040
AGCATCAAGT TTAACACCAA CATGCCTGGA GGATTGGCTT AGCCGGTTGC TAGGGCAGGC    2100
CTGTGGCAGG GTTCTTATCC CAGCTATTAA CGCTCCCTTC CCACTCCTCC AAGTCCTGCA    2160
```

```
AGTCCTGGAT ACAGTGAAAT GTAATTGCAT ATCCCATATC CTTTGCTAGT ATCAAATGGA      2220

TAAAACCCAA AATGGAGTCA TACCAAATGA TCTCATGTAT ACAATACCTG AATAGTCTTG      2280

AACTGATGCA CTGTTAGATA GTATGCACTT ACTCTTCAGC TATTCATAGT GTGCCTCTGC      2340

ACAGTGATGG AAAAGAGGAG CACTGGGGGA GCTCGGTTTT CAAGGGACAA AGGAGAATAA      2400

GACACACAAA GAAATCCAAG GTAGAGCAGA GAAAGGATGG AGACACAGAA GGTTTGCAGG      2460

AACAGGAAGC GAAGGATGCT CCAGTCTGAG GGGGAGGGGA AAGAGAGCCT CTTGAGTAGC      2520

CAGCACCTGA ACTTGGCCTG GAAGCTTGGT GGATAAGGCA GGATAAAGGA GGTGTGGCCT      2580

CTTTGGTATC CTCCCATTGA TAAAGGAGCT CCCTGACCCT TCACTAGACC ATCATCAGTC      2640

CTATGGTTCT TAGACCAATA GAACACAATG GAATTGATTT GTTCCACTTT CCAGGTTAAG      2700

ACTTACAGTC AGGGAAGTTT GTTTTTCTTG CC                                    2732

(2) INFORMATION FOR SEQ ID NO:3:

(i) SEQUENCE CHARACTERISTICS:
        (A) LENGTH: 2430 base pairs
        (B) TYPE: nucleic acid
        (C) STRANDEDNESS: single
        (D) TOPOLOGY: linear (xi) SEQUENCE DESCRIPTION: SEQ ID NO:3:

AACTAGATGC AGCACCACAA TCACTACCAC GTACCAATCA TATACCAATA ATGTACTAAT        60

AATGTACCAA TAACTATGGT TTATAAAGAT GGTGTCATTT AAATCAATAT TAGTTCCTTA       120

TATTACACTC TTTTTAATGA GCGGTGCTGT CTTTGCAAGT GATACCGATC CCGAAGCTGG       180

TGGGCCTAGT GAAGCTGGTG GGCCTAGTGG AACTGTTGGG CCCAGTGAAG CTGGTGGGCC       240

TAGTGAAGCT GGTGGGCCTA GTGGAACTGG TTGGCCTAGT GAAGCTGGTG GGCCTAGTGA       300

AGCTGGTGGG CCTAGTGAAG CTGGTGGGCC TAGTGAAGCT GGTGGGCCTA GTGGAACTGG       360

TTGGCCTAGT GGAACTGGTT GGCCTAGTGA AGCTGGTTGG TCTAGTGAAC GATTTGGATA       420

TCAGCTTCTT CCGTATTCTA GAAGAATAGT TATATTTAAT GAAGTTTGTT TATCTTATAT       480

ATACAAACAT AGTGTTATGA TATTGGAACG AGATAGGGTG AACGATGGTC ATAAAGACTA       540

CATTGAAGAA AAAACCAAGG AGAAGAATAA ATTGAAAAAA GAATTGGAAA AATGTTTTCC       600

TGAACAATAT TCCCTTATGA AGAAAGAAGA ATTGGCTAGA ATATTTGATA ATGCATCCAC       660

TATCTCTTCA AAATATAAGT TATTGGTTGA TGAAATATCA AACAAGGCCT ATGGTACATT       720

GGAAGGTCCA GCTGCTGATA ATTTTGACCA TTTCCGTAAT ATATGGAAGT CTATTGTACT       780

TAAAGATATG TTTATATATT GTGACTTATT ATTACAACAT TTAATCTATA AATTCTATTA       840

TGACAATACC GTTAATGATA TCAAGAAAAA TTTTGACGAA TCCAAATCTA AAGCTTTAGT       900

TTTGAGGGAT AAGATCACTA AAAAGGATGG AGATTATAAC ACTCATTTTG AGGACATGAT       960

TAAGGAGTTG AATAGTGCAG CAGAAGAATT TAATAAAATT GTTGACATCA TGATTTCCAA      1020

CATTGGGGAT TATGATGAGT ATGACAGTAT TGCAAGTTTC AAACCATTTC TTTCAATGAT      1080

CACCGAAATC ACTAAAATCA CCAAAGTTTC TAATGTAATA ATTCCTGGAA TTAAGGCACT      1140

AACTTTAACC GTTTTTTTAA TATTTATTAC AAAATAGATG TAATACCAGA TGTATACATT      1200

ATTATATATT ACAAAATTTA CACATTATTT ATGTATGAAC GAACGAACAT CTCAGTCTTA      1260

AATGAAGAAA TTGGGATAAA TATGGAAATA GATTAAAGTA ACATGAGAAA GATGAATATA      1320

ATATTAGAAT ATGAAATTTA ACAGAAATAA AATGAAGTAA AAGAGTGTAT TTTGTAATAA      1380

TTTATAATAA ATTAGTATAC AATGATTATA TTACAGATGA CTATTGATTA TTGTATCAAT      1440
```

-continued

```
TAAATATTGA TTATTAATGA TATCATATAT GTATATGTTA ATGATTGATT TGTTATACGT    1500

TGTGAATATG TTATATAATG ACATACTATA ATAATTAATA TAATGTAGAG GATATTTTTT    1560

TTAATAGTAT TTAATGAATA TTATAGTTAT AATTATAATA ATGTAGATAA AAATGACATT    1620

AATTTGAATG TTTAAATTGA AATGTATGTA AAAATATGTA TTTATAATCT GAATTGATTA    1680

ATAATATAAT ATTCTACAAT TAATTATTTT TGTAATTATA ATAATTGATT ATATTAATCT    1740

TTGAATTATT ATAAATAATA TTATACTTCA TTAAATTATT TCACATAAAT TTCCAAATTA    1800

TTATCCTTTA TCTTAATGTT ATCCAATTTT ACACATCTTT CTTCATTACA ATATTTTTTT    1860

ACTAATCCTG TATGCTCATA TTCATATTCT TTAGAAATAT AACGAAAATT AGATGTAACT    1920

TCGCCACTTA CAAGTAAACT ACCATCAATA TAATAATAAT GAATACCATT CATGTCCGTA    1980

TATTCTTTAT ATTTTTTATC ATATTTTATT TTGTGATTAT TCCATTCATT TGTATCATTA    2040

TTCAATGAGA GAAATAATAG CAGAAAGATC CTTCTATAGA AACATAAAAT TCAATTAATA    2100

CTGGATTATT ATGTTTGCAA GTATAGATGT TTAAATCAAT AACACTACCA GTTGGTAATT    2160

TAGCATTGTC ATCAAATTCA ATTATATAAT CAGAAATTTT GATTTATCA ATTTATTCG     2220

GATGTGATAA TTTATTTTGT TCTGATTCAT CGATCATGTA TACAAATACT ATTGTTAAAG    2280

GTTCCCTATC CTTATAATTA AAGTGGCCAA TAAGATTGGC ATTAATTACA TTAGTAGTGT    2340

GTGTATTTGT AATAGTATCA TTAGTGGTAC TGACAGTTGT TATAGGTTTT GATTTCCATA    2400

ATGAAACATC ATTTTTATCT ACACAATACA                                    2430

(2) INFORMATION FOR SEQ ID NO:4:

(i) SEQUENCE CHARACTERISTICS:
        (A) LENGTH: 1991 base pairs
        (B) TYPE: nucleic acid
        (C) STRANDEDNESS: single
        (D) TOPOLOGY: linear (xi) SEQUENCE DESCRIPTION: SEQ ID NO:4:

AATGTACAAG ATCAAAATTT CTGATTATAT AATTGAATTT GATGACAATG CTAAATTACC      60

AACTGATAAT GTTATTGGTA TATCCATCTA TACTTGTGAA CACAATAATC CAGTATTAAT     120

TGAATTTTAT GTTTCTAAAA AAGGATCAAT CTGCTATTAT TTCTACTCAA TGAATAATGA     180

TACAAATAAA TGGAATAATC ACAAAATAAA ATATGACAAA AGATTTAATG AACATACTGA     240

CATGAATGGT ATTCATTATT ATTATATTGA TGGTAGTTTA CTTGCGAGTG GCGAAGTTAC     300

ATCTAATTTT CGTTATATTT CTAAAGAATA TGAATATGAG CATACAGAAT TAGCAAAAGA     360

GCATTGCAAG AAAGAAAAAT GTGTAAATGT GGATAACATT GAGGATAATA ATTTGAAAAT     420

ATATGCGAAA CAGTTTAAAT CTGTAGTTAC TACTCCAGCT GATGTAGCGG GTGTGTCAGA     480

TGGATTTTTT ATACGTGGCC AAAATCTTGG TGCTGTGGGC AGTGTAAATG AACAACCTAA     540

TACTGTTGGT ATGAGTTTAG AACAATTCAT CAAGAACGAG CTTTATTCTT TTAGTAATGA     600

AATTTATCAT ACAATATCTA GTCAAATCAG TAATTCTTTC TTAATAATGA TGTCTGATGC     660

AATTGTTAAA CATGATAACT ATATTTTAAA AAAAGAAGGT GAAGGCTGTG AACAAATCTA     720

CAATTATGAG GAATTTATAG AAAAGTTGAG GGGTGCTAGA AGTGAGGGGA ATAATATGTT     780

TCAGGAAGCT CTGATAAGGT TTAGGAATGC TAGTAGTGAA GAAATGGTTA ATGCTGCAAG     840

TTATCTATCC GCCGCCCTTT TCAGATATAA GGAATTTGAT GATGAATTAT TCAAAAGGC      900

CAACGATAAT TTTGGACGCG ATGATGGATA TGATTTTGAT TATATAAATA CAAAGAAAGA     960

GTTAGTTATA CTTGCCAGTG TGTTGGATGG TTTGGATTTA ATAATGGAAC GTTTGATCGA    1020
```

| AAATTTCAGT GATGTCAATA ATACAGATGA TATTAAGAAG GCATTTGACG AATGCAAATC | 1080 |
| TAATGCTATT ATATTGAAGA AAAAGATACT TGACAATGAT GAAGATTATA AGATTAATTT | 1140 |
| TAGGGAAATG GTGAATGAAG TAACATGTGC AAACACAAAA TTTGAAGCCC TAAATGATTT | 1200 |
| GATAATTTCC GACTGTGAGA AAAAAGGTAT TAAGATAAAC AGAGATGTGA TTTCAAGCTA | 1260 |
| CAAATTGCTT CTTTCCACAA TCACCTATAT TGTTGGAGCT GGAGTTGAAG CTGTAACTGT | 1320 |
| TAGTGTGTCT GCTACATCTA ATGGAACTGA ATCTGGTGGA GCTGGTAGTG GAACTGGAAC | 1380 |
| TAGTGTGTCT GCTACATCTA CTTTAACTGG TAATGGTGGA ACTGAATCTG GTGGAACAGC | 1440 |
| TGGAACTACT ACGTCTAGTG GAACTTGGTT TGGAAAATGA AAAATTAGCT CTAGAAACAC | 1500 |
| TTTATTGTTA ATTTTTAAAA ACCTATTGAA AAATCAGATT GTAAAACATA ATTCCACTTC | 1560 |
| TAACCATGCT ATGATTTAAC TAATCAGGAC AAAAAGAAAG CATAATCAAC ATTATTCATT | 1620 |
| CAGTGATGGT GACATAATTC AGAGAATGTG GCAATTGCCT CTTGAAGACC AGAGTTCCAT | 1680 |
| CCACAGGACC CACATGGTTA AGGAGAGAG CTAACTCCTG AAAGTTGTCC TCTGACTAAC | 1740 |
| ACATTCAACT TTTGAGTGTC TCATTTATGT GTTGGCTTCT GTCTAATGTG GAAAATCAT | 1800 |
| TAAGGGCTCT TAAATCAGAT CCTCATTCTC TCTATTAATA AACTATGTGA TAACATCCTT | 1860 |
| CAGCTATGAA AATGTCAGGA GAGAGTCAGG AAAATGGAAG ATATTGTTCA GGACTTAACT | 1920 |
| AGGTGGTGGC ACACAGTTCC TTTACACAGA TTCCTCAGGA CAAGTTTTAG GTGAGGTTTT | 1980 |
| GATCTATCCT G | 1991 |

(2) INFORMATION FOR SEQ ID NO:5:

(i) SEQUENCE CHARACTERISTICS:
        (A) LENGTH: 1271 base pairs
        (B) TYPE: nucleic acid
        (C) STRANDEDNESS: single
        (D) TOPOLOGY: linear (xi) SEQUENCE DESCRIPTION: SEQ ID NO:5:

| TTCACTAGGC CAACCAGCTT CACTAGGCCA ACCAGCTTCA CTAGGCCAAC CAGCTTCACT | 60 |
| AGGCCAACCA GCTTCACTAG GCCAACCAGC TTCACTAGGC CAACCAGTTC CACTAGGCCC | 120 |
| ACCAGCTTCA CTAGGCCCAC CAGCTTCACT AGGCCCACCA GCTTCACTAG GCCAACCAGT | 180 |
| TCCACTAGGC CCACCAGCTT CACTAGGCCC ACCAGCTTCA CTAGGCCCAC CAGCTTCACT | 240 |
| AGGCCCACCA GCTTCACTAG GCCCACCAGC TTCACTAGGC CCACCAGCTT CACTAGGCCC | 300 |
| ACCAGCTTCA CTAGGCCCAC CAGCTTCACT AGGCCCAACA GTTCCACTAG GCCCACCAGC | 360 |
| TTCGCGATCG GTATCACCTG CAAAGACAGC ACCGCTCATT AAAAAGAGTG TAATATAAGG | 420 |
| AACTAATATT GATTTAAATG ACACCATCTT TATAAACCAT AGTTATTGGT ACATTATTAG | 480 |
| TACATTATTG GTATATGATT GGTACGTGGT AGTGATTGTG GTGCTGCATC TAGTTGTCAT | 540 |
| CAATGTGCAT ACATCCTAAC TAATAAGCTA ATAAGCTAAT AAGCAGTTAT ACAATTTCTG | 600 |
| ATAATTGCTT CCAGTTATTC TAGAATCGAT TTGAAGATTT TTCTAAGATT GGGGATAGAC | 660 |
| GTCAATGAAG GCTAGGTTAG GGTTAGGGTT AGGGTTAGGG TTAGGGTTTA GGGTTAGGG | 720 |
| TTTAGGGTTT AGGGTTTAGG GTTAGGGTTT AGGGTTAGG GTTAGGGTT TAGGCTCCCA | 780 |
| AGTTGTCCCG TGAAAGGGCC GTGTCTTTGA TAAATTTTGC CGTCCTGTAC GTTTCCTTTC | 840 |
| TAGAATGCAC AAAAACAAGA ATTTGGCAGC TAGAAACATC GTTAATCACC TCTTGGTAGA | 900 |
| GAATTTCGTT GATTGCGTTG AAACGTTTGA TAGCCTTCTT CTCCTTCACG CCATAATACA | 960 |
| CCTGCTCCAA GGGCACAGGC CTAAAGTGGC TGCCAAAGTA GAAAAGCCCT CGGTCTAGAT | 1020 |

| | |
|---|---|
| TAACAGTGAG AAATCTAGCC ACGTCTTCGT AGTTTGGAAG CGTGGCCGAT AGACCAACTA | 1080 |
| GCCTTACGCG TTCGGGCCTC TGACTCAGGC GGGCCACAAT AGCCTCCAGC ACTGGACCCC | 1140 |
| TAGTGTCATG GAGTAGGTGT ATTTCATCAA TTATAACCAA TCTAAGCCGC TCAAGCAGGG | 1200 |
| GCTCATTGCC TGTTTTACGT GTAACTACGT CAAACTTCTC TGGCGTAGTT ACAATTATAT | 1260 |
| GCGTTTTCTC A | 1271 |

(2) INFORMATION FOR SEQ ID NO:6:

(i) SEQUENCE CHARACTERISTICS:
        (A) LENGTH: 1821 base pairs
        (B) TYPE: nucleic acid
        (C) STRANDEDNESS: single
        (D) TOPOLOGY: linear (xi) SEQUENCE DESCRIPTION: SEQ ID NO:6:

| | |
|---|---|
| TAAACCCTAA ACCCCTAAAC CCTAAACCCT AAACCCTAAA CCCTAAACCC TAAACCCCTA | 60 |
| AACCCTAAAC CCTAAACCCT AAACCCTAAA CCCTAACCCT AAACCCTAAA CCCTAAACCC | 120 |
| TAAACCCTAA ACCCTAACCC TAACCCTAAC CCTAACCCTA ACCTAGCCTT CATTGACGTC | 180 |
| TATCCCCAAT CTTAGAAAAA TCTTCAAATC GATTCTAGAA TAACTGGAAG CAATTATCAG | 240 |
| AAATTGTATA ACTGCTTATT AGCTTATTAG CTTATTAGTT AGGATGTATG CACATTGATG | 300 |
| ACAACTAGAT GCAGCACCAC AATCACTACC ACGTACCAAT CATATACCAA TAATGTACTA | 360 |
| ATAATGTACC AATAACTATG GTTTATAAAG ATGGTGTCAT TTAAATCAAT ATTAGTTCCT | 420 |
| TATATTACAC TCTTTTTAAT GAGCGGTGCT GTCTTTGCAG GTGATACCGA TCGCGAAGCT | 480 |
| GGTGGGCCTA GTGGAACTGT TGGGCCTAGT GAAGCTGGTG GGCCTAGTGA AGCTGGTGGG | 540 |
| CCTAGTGAAG CTGGTGGGCC TAGTGAAGCT GGTGGGCCTA GTGAAGCTGG TGGGCCTAGT | 600 |
| GAAGCTGGTG GGCCTAGTGA AGCTGGTGGG CCTAGTGAAG CTGGTGGGCC TAGTGGAACT | 660 |
| GGTTGGCCTA GTGAAGCTGG TTGGCCTAGT GAAGCTGGTT GGCCTAGTGA AGCTGGTTGG | 720 |
| CCTAGTGAAG CTGGTTGGCC TAGTGAAGCT GGTTGGCCTA GTGAACGATT TGGATATCAG | 780 |
| CTTCTTTGGT ATTCTAGAAG AATAGTTATA TTTAATGAAA TTTATTTATC TCATATATAC | 840 |
| GAACATAGTG TTATGATATT GGAACGAGAT AGGGTGAACG ATGGTCATAA AGACTACATT | 900 |
| GAAGAAAAAA CCAAGGAGAA GAATAAATTG AAAAAAGAAT TGGAAAAATG TTTTCCTGAA | 960 |
| CAATATTCCC TTATGAAGAA AGAAGAATTG GCTAGAATAA TTGATAATGC ATCCACTATC | 1020 |
| TCTTCAAAAT ATAAGTTATT GGTTGATGAA ATATCCAACA AAGCCTATGG TACATTGGAA | 1080 |
| GGTCCAGCTG CTGATGATTT TGACCATTTC CGTAATATAT GGAAGTCTAT TGTACCTAAA | 1140 |
| AATATGTTTC TATATTGTGA CTTATTATTA AAACATTTAA TCCGTAAATT CTATTGTGAC | 1200 |
| AATACCATTA ATGATATCAA GAAAAATTTT GACGACATAG AGAAATTGGG CTGTTTTCAA | 1260 |
| GCTAGAAGCT TCCTCCCTGT TAACTAATGT ATTCATGGTG CCAGAAGGTG CTATGCAGGT | 1320 |
| TGCTAGGGAA TCAAATTCAT CAATAGTCCT GCCCAAGAGT AGTGTGTTAA CTGGCGGTGC | 1380 |
| AAGATGTGCC CTTTGATGCA GTAGTGGCAT GCTTGTTTGT GGGGTAACCC AGTGCTTTCT | 1440 |
| GATTGAGGTC TACTCCACAG GAGGAATAGA TACCTGCTTC TGTAAACTTG GTCAAAACTT | 1500 |
| ATGACTGCAC ATGAAGACAG AGTGGAAAAG ACCTGAAAAC ACACGGGG TCAGGACTGA | 1560 |
| GGAAGACAGG GTTAGTATTA GAGAGATTTG GGAAAAAAA GAGTTAGCAA ATATAGAGTG | 1620 |
| TGATAGTCTA ATGGGGGGAT GAATGGTATC AAAATGAATT ATTTATATGT ATAAAACTGA | 1680 |
| CAATTTTTTA ATTGTGAAAA GGAATGCAAT CCGACCCATC TGGGGGAATT CTAGCTAGCA | 1740 |

```
TCAGTGAGAG AAGAGGCAAG GTGTTAGGAA ATCGTGCAGA ACATGCTCAT CCAGGCTTTA      1800

TTTCTCCATT TACATCTAGA G                                                1821
```

(2) INFORMATION FOR SEQ ID NO:7:

(i) SEQUENCE CHARACTERISTICS:
        (A) LENGTH: 4223 base pairs
        (B) TYPE: nucleic acid
        (C) STRANDEDNESS: single
        (D) TOPOLOGY: linear (xi) SEQUENCE DESCRIPTION: SEQ ID NO:7:

```
CATCACAATT ATTGGCTGTT ACATCACTAT AGTGCTGTAT GTAAAAAATT ATAAAGTGTG        60

ACATCATTAT AATGCAATAT GACATCACAA TTATATACTG TGACTTCACT ATCTTGCACT       120

TTAACATCAC AATTATACAT TGTGACATCA ATATACTGCA CTATGACATC ACGATTATTG       180

ACTGTGACAT CAATACATTC TCTATGAACA CAGTTATACA CTCTGACATC ACTAGCTTGC       240

ACTGTGACAT GACAATTAAA AACTGTGACA TCAATATAAT GGACTGTGAC CTACAATTAT       300

TCACTGTGAA ACCACAACAC TGCAATTGTG TATAATTGGG ATGGGTACTG ATCTGCTGCC       360

CGAGGCTCAA TAGATTACCT AGGCCTCCTC ACTGACACCC ACATTCAGGG GGTCTTGATC       420

AGTCCCATGA TGGATTCCCA GGCTGATGCC TGGGATTCAA GAGTTAACCT TTGTCTGGTC       480

AGCTCTTTCT GGGGGTTAAA CGGATTAAAT GTTTTAATAA TAAGTCACAA TATAGAAACA       540

TATTTTTAGG TACAATAGAC TTCCATATAT TACGGAAATG GTCAAAATCA TCAGCAGCTG       600

GACCTTCCAA TGTACCATAG GCTTTGTTGG ATATTTCATC AACCAATAAC TTATATTTTG       660

AAGAGATAGT GGATGCATTA TCAATTATTC TAGCCAATTT TTCTTTCTTC ATAAGGGAAT       720

ATTGTTCAGG AAAACATTTT TCCAATTCTT TTTTCAATTT ATTCTTCTCC TTGGTTTTTT       780

CTTCAATGTA GTCTTTATGA CCATCGTTCA CCCTATCTCG TTCCAATATC ATAACACTAT       840

GTTCGTATAT ATGAGATAAA TAAATTTCAT TAAATATAAC TATTCTTCTA GAATACCAAA       900

GAAGCTGATA TCCAAATCGT TCACTAGGCC AACCAGCTTC ACTAGGCCAA CCAGCTTCAC       960

TAGGCCAACC AGCTTCACTA GGCCAACCAG CTTCACTAGG CCAACCAGCT TCACTAGGCC      1020

AACCAGCTTC ACTAGGCCCA CCAGCTTCAC TAGGCCCACC AGCTTCACTA GGCCCACCAG      1080

CTTCACTAGG CCCAACAGTT CCACTAGGCC CACCAGCTTC ACTAGGCCCA CCAGCTTCAC      1140

TAGGCCCACC AGCTTCACTA GGCCCACCAG CTTCACTAGG CCCACCAGCT TCACTAGGCC      1200

CACCAGCTTC ACTAGGCCCA CCAGCTTCAC TAGGCCCAAC AGTTCCACTA GGCCCACCAG      1260

CTTCGCGATC GGTATCACCT GCAAAGACAG CACCGCTCAT TAAAAAGAGT GTAATATAAG      1320

GAACTAATAT TGATTTAAAT GACACCATCT TTATAAACCA TAGTTATTGG TACATTATTA      1380

GTACATTATT GGTATATGAT TGGTACGTGG TAGTGATTGT GGTGCTGCAT CTAGTTGTCA      1440

TCAATGTGCA TACATCCTAA CTAATAAGCT AATAAGCTAA TAAGCAGTTA TACAATTTCT      1500

GATAATTGCT TCCAGTTATT CTAGAATCGA TTTGAAGATT TTTCTAAGAT TGGGGATAGA      1560

CGTCAATGAA GGCTAGGTTA GGGTTAGGGT TAGGGTTAGG GTTAGGGTTT AGGGTTTAGG      1620

GTTTAGGGTT TAGGGTTTAG GGTTAGGGTT TAGGGTTTAG GGTTAGGGT TTAGGGTTTA       1680

GGGGTTTAGG GTTTAGGGTT TAGGGTTTAG GGTTTAGGGT TTAGGGTTTA GGGAAGGCTG      1740

AGAACCACTG ACTTAGACTT TCCAAGACTT TGTCATCTTA TGACTTGCCG GTTGCCTCGT      1800

TTCTCCACAC AGCAACCTAT GTTCTCTCTT ATTACAGTTT CTGTGGGACA TGTCATGCTT      1860

CCAGCTTCGA GAATGGAAGC CTATTGTCTT AATGGGTGAG CAAAGTGGGC CCATTCATTA      1920
```

-continued

```
ATCACAGACT AATCCAAAAG GAAATGTGAC ACCTGACCTA AGTCCGACCA ATAGGAGCCA    1980

GGAAAGCTCA CTTCTGGAAT TGTGACTTAG ATATCACGGA TGCATACAGA CTCTTTTTCC    2040

TGCTGAAACA AATGGTGAGG ACCTGTCCAC CCTTGTGGGA AGCTTGCAGT GTAAGATTCT    2100

AATCCATATT GGGGAAATAA GGCTGAGAAG AGAGAGTTCC AGGCCTTGTG ACAGAATCTA    2160

ATCCCTGGAT AAAGTCTCTC TTTTTACAAA GAACATCAGT GTTGCAAGCT CCAAATTCCT    2220

GTTCTTACTT TCTTGAGTCT GTTTTCTTTA TGTATAACCC AAAGCACTTT AACTGACACA    2280

GCTGTGAAGT GAGAATATTT CATAGAAATC CTATTGTTTT GATGTCTTCT AAAAAAGAAA    2340

AAAAGCAATG ATCTGTAACA TTTTTTAACT TAAATAATTA GATTGATTTA AGTGACATCA    2400

AAACATCTGG AAAATGGTGT GGACACAAAT TCACTAGAGA GCCATATTTT TTGCTAACTA    2460

ATTGAGAAAT TAATCACTGG CAAGTCTTTG GTAAAAGTAT CACCTCAGTC ATGATCTCTC    2520

CTGCCTTCAT GACATTTTCC TCATTGGTGT GAGGATGCTA TTCTGCTTTC TATGTGACCA    2580

GGAAATAGTG CTGTCTTCTG TCTAGTTATG ATTTAGGTTG TACACCAGGT TTTCACATAT    2640

GTTCCCTAAC GTCTGTAGTA GGACCAGGGA CTGGTTGGCT TCAAGTTGTT GGATATGGTT    2700

ACCTTAAGTC ATTCATGTAC AGGAACTCAT TTGAGATGAT AGGAAATGAA GTGAAAGATT    2760

TTCTTGCCCC TGTTAAGTAA GATAAAAAGG ATTGTTATGA TGGGCAGGA GCAGATCTAT     2820

TTCCAATAAA CAGAATTTGA AGTGTTTGTG TGATATTCAG ATACCTCATT GTCATTTGAA    2880

TGAATTACTC CTGCTCTCAG TGAAGATGTC TAAGCTGCAA ATAAGAAATG GAGAGCGCTG    2940

TCAGAAGTCA GATGGAATTG AGAATAGGGG CCTGGCTGCA ATCTGTGGAG ACTGCCTAAA    3000

GCAGCTAGAT AAGAAACTAG CAGCTGGGGA GAGAAAGATC GAATTTAGTC GGCCTGTTTT    3060

ATATTTCTT ATAAAAAATA ACTGCTTCGA AATGTTTGAG AAGATAGAGG CAATGAGCAG     3120

AAAGTTGTTC CTTAAATCAG TTATAGAATG AACACATACA CGGGCACTCA GATCAAGCCA    3180

TGCTGAGCTT GAGACACCGG GTGACGCGTG ACTTGTTTAT TCCCAGGCTG CAAAGGAGAG    3240

TAAATGAAGT AACGGGAAGG CCCGGTGTGG TAGGCACACT CCTGCCTGGC ACCATCTGCT    3300

GCTTTTGTCC CTGTTACTCC TTGTTCCTTT CCCTCCTTTT CTCCCTCCCT TCCTCCCTCC    3360

CTCTCTCCCT CCTTCACACT TCTGTCTTTA TTTCCTCCTG GGAGTTAATT GGTGGTAGCC    3420

CCTCTGTGCT GTTCTTTCGG GGGTGCCTTT AATTTCGACA ATACAATGCC ATCCATGGGG    3480

GCATTTTATA TACAGTAATA ATTGTCATTG ATGTGGCCAT AAGGTACTTT TTTGTGGTAC    3540

CCTTCTTGAA CAGAACAGAC ACAGAAGGGC GTGCGTGCGT GCGTGCGTGC GTGCGTGCGT    3600

GCGTGTGTGC GTGTGTGCGT GCGTGTGTGC GTGTGTGCGT GCGTGCGTGT GTGCGTGCGT    3660

GCGTGTGTGC GTGTGTGTGT GTGTGTGTGT GTGTGTGTGT GTGTGTGTGT GTGTGTTGGG    3720

ATGGGGTGGG GAGCGCTAGC TTCCTACTTG TTGTAGGGTG ATGAGGTTTT ATATAGTCTG    3780

TTTCTGAGAC AGTTACCAAA TCCAGCTGGG TTACTTTTTT TTTGGTTTTT TATGAGACAG    3840

GGTTTCTCTG TATTGTTTTG GAGGCTGTCG GTCCAGCCTG GTCTCGAACT CACAGAGATC    3900

CGCCTGCCTC TGCCTCCCGA GTGCTGGGAT TAAAGGTGTG CGCCACCACC GCCCGGCCCC    3960

AGCTGGGTTA CTTATCACTC AGTGGATCTT TCTCTTTTCT TTGTAAGAAG AACTTTGCAT    4020

TGTGGGTCGT CATGGAAGAA CACTTGGAAA GGTACCCTTT CTGCCCCACC CGTTTATTGA    4080

ATGAGTCTTT TTTTTTTTTA ATTAAATAGC AGAACTTTGG GGAAAGATTT AGAAAAGGCC    4140

CTTTTCATAT TATAATACGA GGTATAGGAT GGTTTAAGAT AAGAGACTTT TTGTTAGCTG    4200

TTATCAGTTG AGAAAGGCAC GAG                                           4223
```

(2) INFORMATION FOR SEQ ID NO:8:

(i) SEQUENCE CHARACTERISTICS:
        (A) LENGTH: 2287 base pairs
        (B) TYPE: nucleic acid
        (C) STRANDEDNESS: single
        (D) TOPOLOGY: linear (xi) SEQUENCE DESCRIPTION: SEQ ID NO:8:

```
TTATAAACAT ATCTAAATAT TTTAATAATA ATGATGAAAT TTAACATAGA TAAGATAATA      60

TTAATCAATT TAATAGTATT ATTGAATCGA AATGTAGTGT ATTGTGTGGA TACAAATAAT     120

AGTTCATTAA TTGAATCACA ACCAGTAACA ACTAACATTG ACACTGATAA TACAATTACA     180

ACAAATAAAT ACACTGGTAC TATAATTAAT GCCAATATTG TTGAGTACCG TGAATTTGAG     240

GATGAACCTT TAACAATAGG GTTTAGATAC ACTATAGATA AATCACAACA AAATAAATTA     300

TCACATCCAA ATAAAATTGA TAAAATCAAA TTTTCTGATT ATATAATTGA ATTTGATGAC     360

AATGCTAAAT TACCAACTGA TAATGTTATT TGTATATCCA TCTATACTTG CAAGCATAAT     420

AATCCAGTAT TAATTAGATT CTCATGTTCT ATAGAAAAAT ATTACTACCA TTACTTCTAC     480

TCAATGAATA ATGATACAAA TAAATGGAAT AATCACAAAT TAAAATATGA TAAAACATAC     540

AATGAATATA CTGACAATAA TGGTGTTAAT TATTATAAAA TCTATTATAG TGATAAACAG     600

AATTCCCCTA CTAATGGAAA TGAATATGAG GATGTAGCAT TAGCAAGAAT ACATTGTAAT     660

GAAGAAAGAT GTGCAAATGT AAAGGTAGAT AAAATTAAAT ATAAGAATTT GGAAATTTAT     720

GTGAAACAGT TAGGTACTAT AATTAATGCC AATATTGTTG AGTACCTTGT ATTTGAGGAT     780

GAACCTTTAA CAATAGGGTT TAGATACACT ATAGATAAAT CACAACAAAA TGAATTATCA     840

CATCCAAATA AAATTTATAA AATCAAATTT TCTGATTATA TAATTGAATT TGATGATGAT     900

GCTAAATTAA CAACAATTGG TACTGTTGAA GATATAACCA TCTATACTTG CAAGCATAAT     960

AATCCAGTAT TAATTAGATT CTCATGTTCT ATAGAAAAAT ATTACTACTA TTACTTCTAC    1020

TCAATGAATA ATAATACAAA TAAATGGAAT AATCACAACT TAAAATATGA TAATAGATTC    1080

AAAGAACATA GTGACAAGAA TGGTATTAAT TATTATGAAA TCTCAGCTTT CAATGGAGT     1140

TTCTCTTGTT TTTTCGTTAA TAAATATGAG CATAAAGAAT TAGCAAGAAT ACATTGTAAT    1200

GAAGAAAGAT GTGCAAATGT AAAGGTAGAT AAAATTAAAT ATAAGAATTT GGAAATTTAT    1260

GTGAAACAGT TAGGTACTAT AATTAATGCC AATATTGTTG AGTACCTTGT ATTTGAGGAT    1320

GAACCTTTAA CAATAGGGTT TAGATACACT ATAGATAAAT CACAACAAAA TGAATTATCA    1380

CATCCAAATA AAATTTATAA AATCAAATTT TCTGATTATA TAATTGAATT TGATGATGAT    1440

GCTAAATTAA CAACAATTGG TACTGTTGAA GATATAACCA TCTATACTTG CAAGCATAAT    1500

AATCCAGTAT TAATTAGATT CTCATGTTCT ATAGAAAAAT ATTACTACTA TTACTTCTAC    1560

TCAATGAATA ATAATACAAA TAAATGGAAT AATCACAACT TAAAATATGA TAATAGATTC    1620

AAAGAACATA GTGACAAGAA TGGTATTAAT TATTATGAAA TCTCAGCTTT CAATGGAGT     1680

TTCTCTTGTT TTTTCGTTAA TAAATATGAG CATAAAGAAT TAGCAAGAAT ACATTGTAAT    1740

GAAGAAAAAT GTGTAAATGT AAAGGTAGAT AACATTGGGA ATAAAAATTT GGAAATTTAT    1800

GTGAAATAAT TTATGAAGT ATAATATTAT TTATAATAAT TCAAAGATTA ATATAATTAA    1860

TTATTATAAT TACAAAAATA ATTAATTGTA GAATATTATA TTATTAATCA ATTCAGATTA    1920

TAAATACATA TTTTTACATA CATTTCAATT TAAACATTCA AATTAATGTC ATTTTTATCT    1980

ACATTATTAT AATTATAACT ATAATATTCA TTAAATACTA TTTAAAAAAA TATCCTCTAC    2040

ATTATATCAA TCAATATAAT ATACAATTAT ATAATATATT CACAATGTAT AACAATCAAC    2100
```

```
CCTAACATGT ACATACATAA TATCATTACT AATCAATATT TAATTAATAA AATATTTAAT    2160

AGTCATCTGT AATATAATCA TTGTATACTA ATTTATTATA AATTATTACA AAATACACTC    2220

TTTTACTTCA TTTTATTTCT GTTAAATTTC ATATTCTAAT ATTATATTCA TCTTTCTCAT    2280

GTTACTT                                                              2287
```

(2) INFORMATION FOR SEQ ID NO:9:

(i) SEQUENCE CHARACTERISTICS:
        (A) LENGTH: 2784 base pairs
        (B) TYPE: nucleic acid
        (C) STRANDEDNESS: single
        (D) TOPOLOGY: linear (xi) SEQUENCE DESCRIPTION: SEQ ID NO:9:

```
CACTGCTTTC GCAGCGTTTC TTGCTTTTGG GAATATCTCA CCTGTACTTT CTGCTGGTGG      60

TAGTGGTGGT AATGGTGGTA ATGGTGGTGG TCATCAAGAG CAAAATAATG CTAATGATAG     120

TAGTAATCCC ACCGGAGCCG GTGGACAACC CAATAACGAA AGTAAGAAAA AGGCAGTAAA     180

ACTTGACTTG GACCTCATGA AGAAACAAA GAATGTTTGC ACCACTGTTA ATACTAAACT     240

AGTCGGAAAA GCAAAGAGCA AATTAAACAA ATTAGAAGGT GAATCCCATA AGGAGTATGT     300

AGCTGAGAAA ACGAAGGAGA TAGATGAGAA AAATAAGAAA TTTAACGAGA ATCTTGTTAA     360

AATAGAGAAA AAGAAGAAAA TTAAGGTTCC TGCCGATACT GGTGCTGAAG TGGATGCTGT     420

TGATGATGGT GTTGCGGGTG CACTATCCGA TTTATCCTCC GATATCTCCG CTATTAAGAC     480

TCTCACCGAC GATGTATCCG AGAAGGTTTC TGAAAACTTG AAAGATGATG AGGCCAGTGC     540

AACAGAACAC ACTGATATAA AAGAAAAAGC CACCCTGCTT CAAGAGTCTT GCAACGGAAT     600

TGGCACTATC CTAGATAAGT TGGCCGAATA TTTAAATAAT GATACAACTC AAAATATCAA     660

GAAAGAATTT GATGAACGCA AGAAGAATCT CACCTCTTTG AAGACAAAGG TAGAAAATAA     720

GGATGAAGAT TATGTTGATG TTACCATGAC ATCAAAAACA GATCTGATAA TACACTGTTT     780

AACTTGCACA AACGATGCAC ACGGACTGTT TGATTTCGAA TCGAAGAGCT TGATAAAACA     840

AACCTTTAAA TTGAGGTCCA AAGATGAAGG TGAACTCTGC TAATTTAGAT TTTAGATGGG     900

CCATGTATAT GTTAAACAGC AAGATTCATC TTATAGAAAG CAGTTTGATC GATAACTTCA     960

CCTTGGATAA TCCATCCGCA TACGAAATTT TACGCGTTTC TTATAACTCA AATGAATTTC    1020

AAGTACAATC ACCGCAGAAC ATTAACAATG AAATGGAATT TTCAACGCCC GAATCCAATA    1080

TCATTTGGGT TGTACATAGT GATGTTATAA TGAAAAGGTT CAACTGTAAA AATCGCAAAT    1140

CTCTCAGTAC TCATTCACTC ACTGAAAATG ATATTCTCAA GTTTGGCCGT ATAGAACTCT    1200

CTGTTAAATG TATAATTATG GGCGCAGGTA TCACTGCATC TGATCTTAAT CTAAAGGGAT    1260

TGGGGTTTAT TAGTCCAGAT AAACAATCAA CTAATGTATG TAACTATTTT GAAGATATGC    1320

ATGAATCTTA TCATATTCTT GATACACAAA GGGCCTCGGA TTGTGTATCA GATGATGGCG    1380

CTGATATTGA TATATCCAAC TTCGACATGG TCCAAGACGG TAACATAAAT TCTGTTGACG    1440

CTGATTCTGA AACATGTATG GCAAACTCTG GCGTAACGGT CAATAATACT GAAAATGTTA    1500

GTAATAGTGA GAATTTTGGA AAATTAAAAT CATTGGTAAG CACCACCACT CCTTTGTGCC    1560

GTATTTGCCT GTGTGGTGAA TCAGACCCTG GGCCACTAGT AACCCCTTGC AATTGCAAGG    1620

GGTCCCTAAA TTATGTCCAT CTTGAATGCC TAAGGACTTG GATTAAAGGG CGGTTGTCAA    1680

TTGTGAAGGA TGATGATGCT TCCTTTTTCT GGAAAGAGCT ATCATGTGAG CTATGCGGGA    1740

AGCCGTATCC ATCGGTCCTA CAAGTAGATG ATACAGAGAC TAATTTGATG GATATAAAAA    1800
```

```
AACCGGATGC ACCATATGTG GTATTGGAAA TGAGATCAAA TTCTGGTGAT GGGTGTTTCG    1860

TTGTTTCTGT AGCTAAAAAT AAGGCGATTA TTGGACGGGG GCATGAAAGT GACGTTAGGT    1920

TGAGTGATAT TTCAGTGTCA CGAATGCATG CTTCTTTGGA ATTGGATGGT GGAAAAGTAG    1980

TGATACATGA CCAGCAATCT AAGTTTGGTA CACTCGTTAG GGCCAAAGCG CCTTTTTCAA    2040

TGCCTATAAA GGGTCCCATC TGTCTACAGG TAAGCATTTT CTTTTTGAAC TTGAAAATAT    2100

CTACTCATAG TCTAACCATG GAGAGGGGCA TGGAACATGT CCTTCTCTAA TATTTCCAAA    2160

AAGGATCTAT GCCTGATAAC CTTGGTATTG AAGGTGGCTT TCTCAAAGTG AGACATTCCA    2220

TTTCTGTTGT TGGAGCTATC CTATCTGAGG TTAGTGTTCT GGTAAACATT CCTAGAAAAC    2280

TCATAAAGCA GAAATCTGTG TGTATACTAA ATTGCACAGA GAACTCCACG TGTGTGCTAG    2340

ACTTCACAGA GAACTCTGTG TGTGTGCTAA ACTGCATAGA GAAGAACATG TTGAGTGCAT    2400

CATGGTTGAG GGAAATTGCT TTATATAAAA GATTTATTTT CCTAAGGTAA CTTAGGATTA    2460

ATTTTTCTGA AAGCTTAGTT TTGGTGAGCA CAATTGTGAT CTTTGTTTCT CAGATGGTCG    2520

GGAAGGCACT CCCAGAAAGC AGGTGGATAC ACACTACACT GCATGCTACA CTCTGTAGAC    2580

TAGGAGTATC GTTTTCACAC TTATGAAATA GTCACCATGC TGGGCACAAA TATCTTTTTA    2640

TACACCATAT ATTGTTCATG TTCAGGTCCA CATTTCAATT TGTATGTGAA AAGCATCCGG    2700

GGCTGTCTGA TAAACACATA GAAATGAAGG AAACAGTGTA TGTAACTGAA GCCTTCAGTC    2760

CTTTGCAATT TCTTTGATTC TTAG                                          2784

(2) INFORMATION FOR SEQ ID NO:10:

(i) SEQUENCE CHARACTERISTICS:
        (A) LENGTH: 3701 base pairs
        (B) TYPE: nucleic acid
        (C) STRANDEDNESS: single
        (D) TOPOLOGY: linear (xi) SEQUENCE DESCRIPTION: SEQ ID NO:10:

ACCTATTTAT AATATAGTAT ATTACTGGTT TGTTTTAAAT CGAAAAAATG TATTGTATTT      60

AAGAATGAAA TTATTTATTT ATCATGATTA TCATATTTCT AAATATTAAA ATCTAGTAAC     120

GGTTGCTTGA ATATTTATTT AAATTATATG TAGTAGTATT AAAATGTGTT ATATATAAGT     180

AGTGTTCTAA ATCATCATTA GTAATATTGT ATAAATTAAT TGTAAAAATT GCGATACTAC     240

AATTAATCAA CAATTAAAAT ATATCAGTAT AGATAATTTA ATAAATAAT TAGATAAGAT      300

CTTAAGGATT AAATGACGAA TTTAGAATGA TAAATAATCA TCATAGGCAT TTGTTATAAT     360

ATCATTAATT ATATTCATGT GGTTATAATT ATAAAAGTAT ATATAGTTTT GTAATTGTAA     420

TGATATAAAA TTAGAACAGA TATAATTAAT AATTCAAATA TTATATTAAT TTTATTATAT     480

ATGATTATTA TTGATATTTA TATAATTACA TATTGTTATT GTATCATTTA ATGATTATAT     540

ATCAATATCC ATATATATAT ATAATAATTG AATTATAATT AAATTAATTG GCATATTACA     600

TTTATAATAA TATATTATTA GTCAATATGA CATCATATTA TATTATCCAT CATGATTGTG     660

AATGTAACTA GAACATTGAT TATTATATTA AATCACATAT TAATACTGAT TATAATAATA     720

TCATTGATAA TCTAATAATA TAGTATTATC TCTAATAATA TTGTATTATC TCTAATATTA     780

TGGTATAATA GATACTGTGA AAATAAATTC AACTGGAGAT AAGGAAACCA TTTTGTATAG     840

ATATTTTATA CAAATTATTA TGAAATAATC TAAATAAATG ACAAAAAATC GATTATACAA     900

ATCACATTAA TGACAAACAA ACTTGTATAC ATATATTGAT TAACATTACA AAACTAAATT     960

ATAATATTTA GATTGATAAT TGTTATAATA CTTAACAATA TTCTACTTTT TAATATAATT    1020
```

-continued

```
TTTTATTCAA TAATATACTC TTTCATATTT TGTACTATTT TATATAATCA TATATATTAT    1080

ATAATTATAT ATATTTGATA ATTGAATATA TCAATAATGA TGATATACAT GAATATGCAT    1140

ATATACCCCA TATAATGTTA TTATATTTAG TGCTTACATT ATTAATTATA AATATATTTA    1200

AATAATTAAA TAATAATGAA AATTAACATA GACAATATAA TATTAATCAA TTTGATAATA    1260

TTATTGAATC GTAATGTAGT ATATTGTGTG GATAAAAATG ATGTTTCATT ATGGAAATCA    1320

AAACCTATAA CAACTGTCAG TACCACTAAT GATACTATTA CAAATAAATA CACTAGTACT    1380

GTAATTAATG CCAATTTTGC TAGCTACCGT GAATTTGAGG ATAGGGAACC TTTAACAATA    1440

GGATTTGAAT ACATGATCGA TAAATCACAA CAAGATAAAT TATCACATCC AAATAAAATT    1500

GATAAAATCA AAATTTCTGA TTATATAATT GAATTTGATG ACAATGCTAA ATTACCAACT    1560

GGTAGTGTTA ATGATATATC CATCATTACT TGCAAGCATA ATAATCCAGT ATTAATTAGA    1620

TTCTCATGTT AATAGAAGG ATCTATCTGC TATTATTTCT ACTTATTGAA TAATGATACA    1680

AATAAATGGA ATAATCACAA ATTAAAATAT GATAAAACAT ACAATGAACA TACTGACAAT    1740

AATGGTATTA ATTATTATAA AATCGATTAT AGTGAATCTA CAGAACCTAC TACCGAATCT    1800

ACTACCTGTT TTTGTTTTCG CAAAAAAAAT CATAAATCTG AGCGTAAAGA ATTAGAAAAT    1860

TATAAATATG AGGGTACAGA ATTAGCAAGA ATACATTGTA ATAAAGGGAA ATGTGTAAAA    1920

TTGGGTGACA TTAAGATAAA GGATAAGAAT TTGAAATTT ATGTGAAACA GTTAATGTCT    1980

GTAAATACTC CAGTAAATTT TGACAACCCT ACATCGATTA ATCTACCAAC TGTCAGTACT    2040

ACCAATGATA CTATTACAAA TAAATACACT GGTACTATAA TTAATGCCAA TATTGTTGAG    2100

TACTGTGAAT TGAGGATGA ACCTTTAACA ATAGGGTTTA GATACACTAT AGATAAATCA    2160

CAACAAAATA AATTATCACA TCCAAATAAA ATTGATAAAA TCAAATTTTT TGATTATATA    2220

ATTGAATTTG ATGATGATGT TAAATTACCA ACAATTGGTA CTGTCAATAT TATATATATC    2280

TATACTTGCG AGCATAATAA TCCAGTATTA GTTGAATTTA TAGTTTCTAT AGAAGAATCT    2340

TACTACTTTT ACTTCTACTC AATGAATAAT AATACAAATA AATGGAATAA TCACAAATTA    2400

AAATATGATA AAAGATTCAA AAAATATACT AAGAATGGTA TTAATTGTTA TGAATATGTA    2460

CTTCGTAAAT GCAGTTCTTA TACTCGTAAA ATGAATATG AGCATAAAGA ATTAGCAAGA    2520

ATACATTGTA ATGAAGAAAA ATGTGTAAAT GTAAAGGTAG ATAACATTGA GAAAAAGAAT    2580

TTGGAAATTT ATGTAAAATA ATTTAACGAA GTGTAATATG TAAAATAGTT TAATGAAGTA    2640

TAATATTATT TAAAATAATT CAAAATTTCA GAAATTAATA TAATTAATTA TTATAAATAC    2700

AAAATAATTA ATTACAAATG TGTATTGTTA GTTATTTCAG ATTGTAAATA CATATTTTAC    2760

ATACATTTTT ATTAAAACTT TCAAATTAAT ATTTTCATTT TTATAAGCAT TATTATAATT    2820

ATATACTATA ATTATCAGTC ATCAAATAAT ATCCAAAGTT ATCCTCTACA TTATATCAAT    2880

CATACAGTAT ACAATTATAT AAAATATTAA CAACATATAA CAACCAACAT TAATATATAC    2940

ATAATATCTT TATTAATCAA TATTTAATCA ATACAATAAT TAATAGTTAA CTAACTATAC    3000

ACATAGTGTA TACTAAATTA TTATAAATTA TATGTTATAA TTACAAAAAC GTCATTTACT    3060

TATTTTATTT CAGTTATGTT TCATAGTCTA ATTTAGATTT GGTGAAACGC ATCTGGCTGA    3120

TGTGCTGGTG AGCAAGCAGT TCCACGAAGC AAACAATATG ACTGATGCGC TGGCGGCGCT    3180

TTCTGCGGCG GTTGCCGCAC AGCTGCCTTG CCGTGACGCG CTGATGCAGG AGTACGACGA    3240

CAAGTGGCAT CAGAACGGTC TGGTGATGGA TAAATGGTTT ATCCTGCAAG CCACCAGCCC    3300

GGCGGCGAAT GTGCTGGAGA CGGTGCGCGG CCTGTTGCAG CATCGCTCAT TTACCATGAG    3360
```

-continued

| | |
|---|---|
| CAACCCCGAA CCGTATTCGT TCGTTGATTG GCGCGTTTGC GGGCAGCAAT CCGGCAGCGT | 3420 |
| TCCATGCCGA AGATGGCAGC GGTTACCTGT TCCTGGTGGA AATGCTTACC GACCTCAACA | 3480 |
| GCCGTAACCC GCAGGTGGCT TCACGTCTGA TTGAACCGCT GATTCGCCTG AAACGTTACG | 3540 |
| ATGCCAAACG TCAGGAGAAA ATGCGCGCGG CGCTGGAACA GTTGAAAGGG CTGGAAAATC | 3600 |
| TCTCTGGCGA TCTGTACGAG AAGATAACTA AAGCACTGGC TTGATAAATA ACCGAATGGC | 3660 |
| GGCAATAGCG CCGCCATTCG GGGAATTTAC CCCTGTTTTC T | 3701 |

(2) INFORMATION FOR SEQ ID NO:11:

(i) SEQUENCE CHARACTERISTICS:
        (A) LENGTH: 1287 base pairs
        (B) TYPE: nucleic acid
        (C) STRANDEDNESS: single
        (D) TOPOLOGY: linear (xi) SEQUENCE DESCRIPTION: SEQ ID NO:11:

| | |
|---|---|
| CTCGTGCCGC TCGTGCCGAT TATTATAAAT ATTTAGTTGA TGAATATAGT TCTCCCAGGG | 60 |
| AGGAAAGAGA ATTAGCAAGA GTACATTGTA ATGAAGAAAA ATGTGTAAAA TTGGATGGCA | 120 |
| TTAAGTTTAA GGATAAGAAT TTGGAAATTT ATGTGAAACA GTTAATGTCT GTAAATACTC | 180 |
| CAGTTGTATT TGACAACAAT ACATTGATTA ATCCAACTAG CAGCAGTGGT GCCACTGATG | 240 |
| ACATAACATA TGAATTATCG GTGGAATCAC AACCTGTACC AACTAACATT GACACAGGTA | 300 |
| ATAATATTAC AACAAATACA TCAAATAATA ATCTAATTAA AGCTAAATTT CTTTATAATT | 360 |
| TTAATCTTCC TGGTAAACCT TCAACAGGAC TATTTGAATA CACTATAGAT AAATCAGAAC | 420 |
| AAAATAAATT ATCACATCCA AATAAAATTG ATAAAATCAA ATTTTCTGAT TATATAATTG | 480 |
| AATTTGATGA TGATGCTAAA TTACCAACAA TTGGTACTGT CAATATTATA TCCATCATTA | 540 |
| CTTGCAAGCA TAATAATCCA GTATTAGTTG AATTTATAGT TTCTACAGAA ATATATTGCT | 600 |
| ACTACAATTA CTTCTACTCA ATGAATAATA ATACAAATAA ATGGAATAAT CACAAATTAA | 660 |
| AATATGATAA AAGATATAAA GAAGAATATA CAGATGATAA TGGTATTAAT TATTATAAAT | 720 |
| TAAATGATAG TGAACCTACT GAATCTACAG AATCTACTAC CTGTTTTTGT TTTCGCAAAA | 780 |
| AAAATCATAA ATATGAAAAT GAGCGTACAG CATTAGCAAA AGAACATTGC AATGAAGAAA | 840 |
| GATGTGTAAA GGTAGATAAC ATTAAGGATA ATAATTTGGA AATTTATCTA AAATAATTTA | 900 |
| ACGAAGTATA ATATTATTTA TAATAATTCA AAATTTCAGA AATTAATATA ATTAATTATT | 960 |
| ATAAATACAA AATAATTAAT TACAAATGTG TATTGTTAGT TATTTCAGAT TGTAAATACA | 1020 |
| TATTTTACAT ACATTTTTAT TAAAACTTTC AAATTAATAT TTTCATTTTT ATAAGCATTA | 1080 |
| TTATAATTAT ATACTATAAT TATCAGTCAT CAAATAATAT CCAAAGTTAT CCTCTACATT | 1140 |
| ATATCAATCA TACAGTATAC AATTATATAA AATATTAACA ACATATAACA ACCAACATTA | 1200 |
| ATATATACAT AATATCTTTA TTAATCAATA TTTAATCAAT ACAATAATTA ATAGTTAACT | 1260 |
| AACTATACAC ATAGTGTATA CTAAATT | 1287 |

(2) INFORMATION FOR SEQ ID NO:12:

(i) SEQUENCE CHARACTERISTICS:
        (A) LENGTH: 572 base pairs
        (B) TYPE: nucleic acid
        (C) STRANDEDNESS: single
        (D) TOPOLOGY: linear (xi) SEQUENCE DESCRIPTION: SEQ ID NO:12:

| | |
|---|---|
| CTTCATTGAC GTCTATCCCC AATCTTAGAA AAATCTTCAA ATCGATTCTA GAATAACTGG | 60 |

-continued

```
AAACAATTAT CAGAAATTGT ATAACTGCTT ATTAGCTTAT TAGCTTATTA GTTAGGATGT      120

ATGCACATTG ATGACAACTA GATGCAGCAC CACAATCACT ACCACGTACC AATCATATAC      180

CAATAATGTA CTAATAATGT ACCAATAACT ATGGTTTATA AGATGGTGT  CATTTAAATC      240

AATATTAGTT CCTTATATTA CACTCTTTTT AATGAGCGGT GCTGTCTTTG CAAGTGATAC      300

CGATCCCGAA GCTGGTGGGC CTAGTGAAGC TGGTGGGCCT AGTGAAGCTG GTGGGCCTAG      360

TGGAACTGTT GGGCCCAGTG AAGCTGGTGG GCCTAGTGAA GCTGGTGGGC CTAGTGGAAC      420

TGGTTGGCCT AGTGAAGCTG GTGGGCCTAG TGAAGCTGGT GGGCCTAGTG AACTGGTTG       480

GCCTAGTGAA GCTGGTTGGT CTAGTGAACG ATTTGGATAT CAGCTTCTTC CGTATTCTAG      540

AAGAATAGTT ACATTTAATG AAGTTTGTTT AT                                    572
```

(2) INFORMATION FOR SEQ ID NO:13:

(i) SEQUENCE CHARACTERISTICS:
        (A) LENGTH: 2338 base pairs
        (B) TYPE: nucleic acid
        (C) STRANDEDNESS: single
        (D) TOPOLOGY: linear (xi) SEQUENCE DESCRIPTION: SEQ ID NO:13:

```
CTCGTGCCGA ATCTTAGAAA AATCTTCAAA TCGATTCTAG AATAACTGGA AACAATTATC       60

AGAAATTGTA TAACTGCTTA TTAGCTTATT AGCTTATTAG TTAGGATGTA TGCACATTGA      120

TGACAACTAG ATGCAGCACC ACAATCACTA CCACGTACCA ATCATATACC AATAATGTAC      180

TAATAATGTA CCAATAACTA TGGTTTATAA AGATGGTGTC ATTTAAATCA ATATTAGTTC      240

CTTATATTAC ACTCTTTTTA ATGAGCGGTG CTGTCTTTGC AAGTGATACC GATCCCGAAG      300

CTGGTGGGCC TAGTGAACT  GTTGGGCCCA GTGAAGCTGG TGGGCCTAGT GAAGCTGGTG      360

GGCCTAGTGG AACTGGTTGG CCTAGTGAAG CTGGTGGGCC TAGTGAAGCT GGTGGGCCTA      420

GTGGAACTGG TTGGCCTAGT GAAGCTGGTT GGTCTAGTGA ACGATTTGGA TATCAGCTTC      480

TTCCGTATTC TAGAAGAATA GTTACATTTA ATGAAGTTTG TTTATCTTAT ATATACAAAC      540

ATAGTGTTAT GATATTGGAA CGAGATAGGG TGAACGATGG TCATAAAGAC TACATTGAAG      600

AAAAAACCAA GGAGAAGAAT AAATTGAAAA AGAATTGGA  AAAATGTTTT CCTGAACAAT      660

ATTCCCTTAT GAAGAAAGAA GAATTGGCTA GAATATTTGA TAATGCATCC ACTATCTCTT      720

CAAAATATAA GTTATTGGTT GATGAAATAT CAAACAAGGC CTATGGTACA TTGGAAGGTC      780

CAGCTGCTGA TAATTTTGAC CATTTCCGTA ATATATGGAA GTCTATTGTA CTTAAAGATA      840

TGTTTATATA TTGTGACTTA TTATTACAAC ATTTAATCTA TAAATTCTAT TATGACAATA      900

CCATTAATGA TATCAAGAAA AATTTTGACG AATCCAAATC TAAAGCTTTA GTTTTGAGGG      960

ATAAGATCAC TAAAAAGGAC GTGTATGTAA ATGATCACTA AACGGGCTCC ACATATCTAT     1020

TACTGGGGTA GATATTATAA GTTATGGATA AGTAAATTTA TGGCGATAGA TTCCAACAAA     1080

TTTGTGGTTA GTAGCGACAA TGATTATGGC TAGTGTGTGG AGTACTTATG AGTGAATGAT     1140

TGTAGTGGTG GCTAGCAGTG AGTATAGTTA GGTAATCCCT ACACACCCAT TTAAATAAGA     1200

TGCAAATAGC ATTAAATTG  ACATATATTG TGTGTATGTC CACGTTTATT GCGTTTCCAT     1260

GACGTATCTG CTGAGGTGTG TCTTGTGTAT CTAAGTACCA GACACAGCAC TTAAATTGTT     1320

ATGGGCATGA CGATGGATGT TAAAGGTTTA TACACTCCAA AGGCACGTTC TTCTGCTAGG     1380

GAAACGAGGG ACAAGTTCGA TTTTGCTATA CAAAGCAAGT TTCACTCCCT GGACTTTACA     1440

CTGGATGACT TGATATAGG  TGCATTCGTG GTAAACCTCA AAATTTACTC AGGGCGATGG     1500
```

-continued

```
TGCCCATGGG CAGGTTTTTT TGGCAAGGGA ACGACGTACC GGTTTTATTT GCGTGTTAAA    1560

ATGCATTTTT AAATCACAAC TTGTGAAGTA ATTGCCTAAT AATCACACAG AAATGGACAG    1620

GAAGCTATTT TCAAGCGGGA AATCGAATTG CACGGGCATC TGAGACATCC AAACATAGCA    1680

TGGTATGTAC ATATTTATCC AGCTTGTATA CCTGGTTCAC TAGCCCTACT ATGATATTCA    1740

TAGTGATGGA ATATTGTTAC AATGGCGATC TATTTAATTA TATGTCAAAA CATGGCCAAC    1800

TGAGTGAAGA AAGGGTATCA GAGTATACAG ATATTTACAT AGAATTTTGT TCGAAGTCAT    1860

TTGGGCCATT AGAAGCTGCC ACGACAAACG CATAGCGCAC TTGGATATTA AACCAGTAAG    1920

GTTCTATGTT ACAGAGGAGA ATATATTATT GGACCATGAA AACAGGTGTA AATTGGCGGA    1980

CTTTGGATTC TCTGCACACA TAGGGCATTT GTACCGCTCA AACGGAGTGC TCATCATCGT    2040

GGCACGCATG GTAACACGCA ATTWATGGCA GATTATTGGT CTCCGGAGCA GTGTGCCAAA    2100

CATTTGGGTC TGGGGTTGAA GTATGGGGAG TATGATGAAC AAAGCGACAT ATGGGCGTTG    2160

GGCATATTGG CAGTTGAATT GTTTATTGGA TACCCTCCAT TTGGATCTAC TACTGAAGAG    2220

CCCAACAATG TGATTATGAA CAGAATCCAC ACTTACCACT GGACCAAACA TGTACTTTTA    2280

TCTATTACGC AGATTTTTGA AATGAAGAGG GAAAACATC TACTCTCGTC GACGCCTG     2338

(2) INFORMATION FOR SEQ ID NO:14:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (xi) SEQUENCE DESCRIPTION: SEQ ID NO:14:

TTGCCTGGAC CTTCTCTGTC CTAGAATTAC AGGAATTCTC TTATACTGTT AATACAAAA     60

CACTTGGAAG AATTTCACCA ATTGCATATG AAACATGGAA TCCAAGAGAC CAAAATTTAA   120

AACCTTGAAA TAGAAGCACT TATGCCAATA TTGGAAATTA CTTAGTGAAG TGATCCAAAG   180

TACTGATTTG GTCAGAAGAC ATCACCAGGG CACTAGCTGG CCTAGTGACC TGAGTATTTG   240

TGAAAGCTGA TTTTAATGTT GAGAACATGA AGGAAGCAGT ATTGAGGTAA TGGAATCTTG   300

TAGATTATAG TAGAAGCCAA CTGAGACCAA GAAATGTACG GTAGGAATGA AATAAGGTCT   360

TGGGTGGTCA TTGCATGGAG CTGTGAAAGT GAAGCGTTGT TGGGGTATAG ATTCGCAAGT   420

CTTGGGGCAT GACTATGTGG GGTTACCAAG GTTAGGTTAA CTGAGGTGGA AGATCCACT    480

CTAAATGGGG GAGTTACCAT TTCATGTGCT GGGATCCCAG AGATGTCAAA GGAGAAAATA   540

AGCTATTGAA TAAGAGCATC TATATCCCTT GCTTCTTGGC TATGGATGTT ATGTGACTAG   600

TCATCTCTTA GTCTTACCTT CACCATTATA ACAAGATTTT CTAGAACTTT GGGTTAAATT   660

AAATCCTTTA TTCCTCACGT TGCTGTCTTA GTTACTTTCC TGTTGCTTTG ATAAAGCATT   720

CTGGCCAAG                                                           729

(2) INFORMATION FOR SEQ ID NO:15:

(i) SEQUENCE CHARACTERISTICS:
        (A) LENGTH: 1448 base pairs
        (B) TYPE: nucleic acid
        (C) STRANDEDNESS: single
        (D) TOPOLOGY: linear (xi) SEQUENCE DESCRIPTION: SEQ ID NO:15:

ACATGTTGAC TTTTGGAAAT ATACGTTTTC ATAATATAAA TCTCCCACCA TTTTCATTGG     60
```

-continued

| | |
|---|---|
| GCATAATTCA CTCGATTACG GTAGAAAAGG CGATTAACTC TGAAGATTTT GACGGAATAC | 120 |
| AAACACTTTT ACAAGTGTCT ATCATTGCTA GTTACGGTCC ATCTGGCGAT TACAGTAGTT | 180 |
| TTGTGTTCAC TCCAGTTGTA ACAGCAGACA CCAACGTTTT TTACAAATTA GAGACGGATT | 240 |
| TCAAACTTGA TGTTGATGTT ATTACTAAGA CATCACTAGA ATTGCCCACA AGTGTTCCTG | 300 |
| GCTTTCACTA CACCGAAACT ATTTACCAAG GCACAGAATT GTCAAAATTT AGCAAGCCTC | 360 |
| AGTGCAAACT TAACGATCCT CCTATTACAA CAGGATCGGG GTTGCAAATA ATACATGATG | 420 |
| GTTTGAATAA TTCGACAATT ATAACCAACA AGAAGTTAA TGTGGATGGA ACAGATTTAG | 480 |
| TTTTTTTTGA ATTGCTCCCT CCATCGGATG GCATTCCCAC CTTGCGATCA AAATTATTTC | 540 |
| CCGTCCTGAA ATCAATTCCA ATGATATCTA CCGGGGTTAA TGAATTACTG TTGGAAGTAC | 600 |
| TCGAGAACCC CTCTTTCCCT AGTGCAATTA GCAATTACAC CGGACTGACA GGCCGACTTA | 660 |
| ACAAATTACT TACAGTTTTA GACGGTATTG TTGATAGCGC CATTAGTGTC AAGACTACAG | 720 |
| AAACTGTCCC TGACGACGCA GAAACTTCTA TTTCTTCATT GAAATCATTG ATAAAGGCAA | 780 |
| TACGAGATAA TATTACTACC ACTCGAAACG AAGTTACCAA AGATGATGTT TATGCATTGA | 840 |
| AGAAGGCCCT CACTTGTCTA ACGACACACC TAATATATCA TTCAAAAGTA GATGGTATAT | 900 |
| CATTCGACAT GCTGGGAACA CAAAAAAATA AATCTAGCCC ACTAGGCAAG ATCGGAACGT | 960 |
| CTATGGACGA TATTATAGCC ATGTTTTCGA ATCCCAATAT GTATCTTGTG AAGGTGGCGT | 1020 |
| ACTTGCAAGC CATTGAACAC ATTTTTCTCA TATCAACCAA ATACAATGAT ATATTTGATT | 1080 |
| ACACCATTGA TTTTAGTAAG CGTGAAGCTA CTGATTCTGG ATCATTTACC GATATATTGC | 1140 |
| TCGGAAACAA GGTGAAGGAA TCTTTGTCAT TTATTGAGGG TTTGATTTCT GACATAAAAT | 1200 |
| CTCACTCATT GAAAGCTGGG GTTACAGGAG GTATATCAAG TTCATCATTA TTTGATGAAA | 1260 |
| TCTTCGACGA GTTAAATTTG GATCAAGCAA CAATTAGAAC CCTTGTTGCA CCATTAGATT | 1320 |
| GGCCACTTAT CTCAGACAAA AGCCTCCACC CTTCACTGAA GATGGTTGTG GTCCTGCCAG | 1380 |
| GATTTTTCAT AGTTCCTTAA TAACATGACA TTTCATAGTC CCTTCAGTCC TGATGACAAG | 1440 |
| ACGGTGAA | 1448 |

(2) INFORMATION FOR SEQ ID NO:16:

(i) SEQUENCE CHARACTERISTICS:
        (A) LENGTH: 1350 base pairs
        (B) TYPE: nucleic acid
        (C) STRANDEDNESS: single
        (D) TOPOLOGY: linear (xi) SEQUENCE DESCRIPTION: SEQ ID NO:16:

| | |
|---|---|
| GCCTAAGCCC AAATGGGATT TAAGCAGGAG GGGATAAAAC AGATGACCTC CACCATGCCC | 60 |
| TACTAACTCT AAGCTAAGGA AATCCAGCCT GCTGGCTATT TACCTGCTTT CCTCGAAGTG | 120 |
| AAAGGCCAGA GTCACCCCCA ATCTTTCCCA AAAGATTGAA GTCACTCTCT CCATGCCGGC | 180 |
| AAAGGTAGAT GGTGCGAGGC TGGACATGGA TATTCATAAG GTAGTAGACA ATTTTACTCT | 240 |
| GGATGTAGTC CTGGACTCTG TTGACCAGAA ATCTCTGGCC TACATTAATC ACCTTGATGA | 300 |
| AGACAGATCC CTAGGACAGA GTAGAAAGAG CAATTTTATG GTCAGAAAAT CTGAAACTAG | 360 |
| GAGTGTGGCA AGCAAGGGGG CAAGGCTATC AGCACCTAGT GACAATCCCA GCACTTAGAA | 420 |
| GGCTTAGCTG GAAGGGGCTT AGGTTTGACC CTGACTCAAG ACAAATGAAC ATATGAAAAG | 480 |
| TATGGGGAGA ATGATCTGTG TATTGACTGG TAGGGCCTCA TCAGCTATTC CTTCTCTCCC | 540 |
| TGTCACTGCC ATCTCGTGCC GAATTCGGCA CGAGCTCGTG CCGAAACCCT AAACCCTAAA | 600 |

| | |
|---|---|
| CCCCTAAACC CTAAACCCTA AACCCTAAAC CCTAAACCCT AAACCCTAAA CCCTAAACCC | 660 |
| TAAACCCCTA AACCCCTAAA CCCTAAACCC TAAACCCTAA ACCCTAAACC CTAAACCCTA | 720 |
| AACCCTAACC CTAACCCTAA CCCTAACCCT AACCTAGCCT TCATTGACGT CTATCCCCAA | 780 |
| TCTTAGAAGA ATCTTCAAAT CGATTCTAGA ATAACTGGAA ACAATTATCA GAAATTGTAT | 840 |
| AACTGCTTAT TAGCTTATTA GCTTATTAGT TAGGATGTAT GCACATTGAT GACAACTAGA | 900 |
| TGCAGCACCA CAATCACTAC CACGTACCAA TCATATACCA ATAATGTACT AATAATGTAC | 960 |
| CAATAACTAT GGTTTATAAA GATGGTGTCA TTTAAATCAA TATTAGTTCC TTATATTACA | 1020 |
| CTCTTTTTAA TGAGCGGTGC TGTCTTTGCA AGTGATACCG ATCCCGAAGC TGGTGGGCCT | 1080 |
| AGTGAAGCTG GTGGGCCTAG TGGAACTGTT GGGCCCAGTG AAGCTGGTGG GCCTAGTGAA | 1140 |
| GCTGGTGGGC CTAGTGGAAC TGGTTGGCCT AGTGAAGCTG GTGGGCCTAG TGAAGCTGGT | 1200 |
| GGGCCTAGTG AAGCTGGTGG GCCTAGTGAA GCTGGTGGGC CTAGTGGAAC TGGTTGGCCT | 1260 |
| AGTGGAACTG GTTGGCCTAG TGAAGCTGGT TGGTCTAGTG AACGATTTGG ATATCAGCTT | 1320 |
| CTTCCGTATT CTAGAAGAAT AGTTATATTT | 1350 |

(2) INFORMATION FOR SEQ ID NO:17:

(i) SEQUENCE CHARACTERISTICS:
        (A) LENGTH: 1820 base pairs
        (B) TYPE: nucleic acid
        (C) STRANDEDNESS: single
        (D) TOPOLOGY: linear (xi) SEQUENCE DESCRIPTION: SEQ ID NO:17:

| | |
|---|---|
| GGAAAGCCTT AAACATGCAT GGGAATAATG AAATAGTAAA AATTGCAGCC ATGGCAATGT | 60 |
| AATAATGAGT GGATGTTTCA GTCTTGAGGC TCTTTAACAA GAGTGTTGTC TTGTAGTCAA | 120 |
| AGACAAAGTG ATTCGTCATG CCGCATTCGC AGCCACCATC ATCATCAGGC GACGACGGGT | 180 |
| CTCTTTCATT ATCCTCGGGC TTATTATTGC AACCATGACA CCCTTCTTTA CAAAAGTCTT | 240 |
| TTTTTTTCAG CGGTGTCTGA GTATTATGCG ATTTTATTCC AGCCTTCCCA CTTTTATTCT | 300 |
| TATTGAGATT GCCATGCTCT TCTTCATGAG CGTCACTTGT TTCCTGCGGT GTCTGAGTAT | 360 |
| CATACGATTT TATTCCAGCA TTTCCACTTT TATTCTTATT GATTTTGTCA TGCCCTTCTT | 420 |
| CACACTCTTC ACATATTTCT TGCGTTGTCT GAGTATCATG CGATTTTCTT TCAGCCTTCT | 480 |
| CACTTTTATT CGTATTGATT TTGTCATGCC CTTCTTCATG AGCGTCACTT GTTTCCTGCG | 540 |
| GTGTCTGAGT ATCATACGAT TTTATTCCAG CATTTCCACT TTTATTCTTA TTGATTTTGT | 600 |
| CATGCCCTTC TTCACACTCT TCACATATTT CTTGCGTTGT CTGAGTATCA TACGATTTTA | 660 |
| TTCCAGCATT TCCACTTTTA TTCTTATTGA TTTTGTCATG CCCTTCTTCA CACTCTTCAC | 720 |
| ATATTTCTTG CGTTGTCTGA GTATCATGCG ATTTTCTTTC AGCCTTCTCA CTTTTATTCG | 780 |
| TATTGGGTTT GCCATGCCCT TCTTTACGCT CTTCATATAT TTCTTGTGCC GTTAGTCTCA | 840 |
| GTAAGTTGTC AAGCTCTTCA TATATTTCTT GCGGTGTCTG AGTATCATGC GATTTTCTTT | 900 |
| CAGTCTTCTC ACTTTTATTC GTATTGAGTT TGCCATTCCC TTCTTCATGA TCGTCACTTG | 960 |
| TTTCTTGCGC CGTTAGTCTC ATTAAGTTGT CAAGCTCTTC ATCATCTATT GAATGGTATG | 1020 |
| GAGCTGTATC TTCCCAGGGT GGTTGAATTA TGTCATTCTC GCCGATTTTA AATGATGGTT | 1080 |
| CTTCATCATT TATATCAGAT GCCATGTCTG AGTGGTGCCC TAATCTAGAG AATTGGTGTG | 1140 |
| GTACCCCCTC ATCCAAACTT TCGGGCAACA CCCTGGTATC AGAATCCATT TGTTCGAGCG | 1200 |
| GCTCACTATC GCAAGCGTCT TGTGGATTGA TGTTATCATG TTCCTGGATT TCAACATGTA | 1260 |

-continued

```
CAGATTCTGA ATCCGCATTG GGTTCTGGAA TATAGTTGGT AACTACATTT GTTTCTAGAG      1320

AAGTATCATT CTTATATTAA TTCATCTAAG ATCTGTGCTT CTTTGTTTCT ACACATACAG      1380

GGTGTCTCTT TTCCCAACAT AAATATCTGTA AATTCTTCCC AGAAGCAGAA CCTTGTTGGT     1440

ACCAGACAGC ATCGGGTCTC TGTGAGTTTC TATTCAGGCA ACAGGTGTAT TCTGTTTGCC      1500

AGTCCAAGTG CATCCTGTAT TCTAGTACTG GCTTACTACC CCAAGCAAAT CACTGGCATC     1560

AACATCTAGC ACTGAGTGAA GCATGATCTC TTCTACAAGG TGTTTTTCCA TTGTGTTGTA     1620

AGCCCGTATA CAAGGCTGTT CCCACTCAAC AATGAAGAGA CCTCTTAGCA TGAATGGCCA     1680

GATGTCTGTT CTTTAAATTA AATCAATATG TTTTGCTCAA TATGTCAGAC TTGTTTGTGG     1740

TGGAGCCAAA ATTGGAGGTC CCATCGAGAT TTGGAGAAAC TTGAAATGAA TGCAAAAGAT     1800

GGTGGGGGCT ACTCGTGCCG                                                  1820
```

(2) INFORMATION FOR SEQ ID NO:18:

(i) SEQUENCE CHARACTERISTICS:
      (A) LENGTH: 263 amino acids
      (B) TYPE: amino acid
      (C) STRANDEDNESS:
      (D) TOPOLOGY: linear (xi) SEQUENCE DESCRIPTION: SEQ ID NO:18:

```
Leu Phe Leu Met Ser Gly Ala Val Phe Ala Ser Asp Thr Asp Pro Glu
1               5                   10                  15

Ala Gly Gly Pro Ser Glu Ala Gly Gly Pro Ser Gly Thr Val Gly Pro
            20                  25                  30

Ser Glu Ala Gly Gly Pro Ser Glu Ala Gly Gly Pro Ser Gly Thr Gly
        35                  40                  45

Trp Pro Ser Glu Ala Gly Gly Pro Ser Glu Ala Gly Gly Pro Ser Glu
    50                  55                  60

Ala Gly Gly Pro Ser Glu Ala Gly Gly Pro Ser Gly Thr Gly Trp Pro
65                  70                  75                  80

Ser Gly Thr Gly Trp Pro Ser Glu Ala Gly Trp Ser Ser Glu Arg Phe
                85                  90                  95

Gly Tyr Gln Leu Leu Pro Tyr Ser Arg Arg Ile Val Ile Phe Asn Glu
            100                 105                 110

Val Cys Leu Ser Tyr Ile Tyr Lys His Ser Val Met Ile Leu Glu Arg
        115                 120                 125

Asp Arg Val Asn Asp Gly His Lys Asp Tyr Ile Glu Glu Lys Thr Lys
    130                 135                 140

Glu Lys Asn Lys Leu Lys Lys Glu Leu Glu Lys Cys Phe Pro Glu Gln
145                 150                 155                 160

Tyr Ser Leu Met Lys Lys Glu Glu Leu Ala Arg Ile Phe Asp Asn Ala
                165                 170                 175

Ser Thr Ile Ser Ser Lys Tyr Lys Leu Leu Val Asp Glu Ile Ser Asn
            180                 185                 190

Lys Ala Tyr Gly Thr Leu Glu Gly Pro Ala Ala Asp Asn Phe Asp His
        195                 200                 205

Phe Arg Asn Ile Trp Lys Ser Ile Val Leu Lys Asp Met Phe Ile Tyr
    210                 215                 220

Cys Asp Leu Leu Leu Gln His Leu Ile Tyr Lys Phe Tyr Tyr Asp Asn
225                 230                 235                 240

Thr Val Asn Asp Ile Lys Lys Asn Phe Asp Glu Ser Lys Ser Lys Ala
                245                 250                 255
```

```
Leu Val Leu Arg Asp Lys Ile
            260
```

(2) INFORMATION FOR SEQ ID NO:19:

(i) SEQUENCE CHARACTERISTICS:
        (A) LENGTH: 310 amino acids
        (B) TYPE: amino acid
        (C) STRANDEDNESS:
        (D) TOPOLOGY: linear (xi) SEQUENCE DESCRIPTION: SEQ ID NO:19:

```
Met Ser Gly Ala Val Phe Ala Ser Asp Thr Asp Pro Glu Ala Gly Gly
1               5                   10                  15

Pro Ser Glu Ala Gly Gly Pro Ser Gly Thr Val Gly Pro Ser Glu Ala
            20                  25                  30

Gly Gly Pro Ser Glu Ala Gly Gly Pro Ser Gly Thr Val Gly Pro Ser
        35                  40                  45

Glu Ala Gly Gly Pro Ser Glu Ala Gly Gly Pro Ser Gly Thr Gly Trp
50                  55                  60

Pro Ser Glu Ala Gly Gly Pro Ser Glu Ala Gly Gly Pro Ser Gly Thr
65                  70                  75                  80

Val Gly Pro Ser Glu Ala Gly Gly Pro Ser Glu Ala Gly Gly Pro Ser
            85                  90                  95

Gly Thr Gly Trp Pro Ser Glu Ala Gly Gly Pro Ser Glu Ala Gly Gly
            100                 105                 110

Pro Ser Glu Ala Gly Gly Pro Ser Glu Ala Gly Gly Pro Ser Gly Thr
            115                 120                 125

Gly Trp Pro Ser Gly Thr Gly Trp Pro Ser Glu Ala Gly Trp Ser Ser
130                 135                 140

Glu Arg Phe Gly Tyr Gln Leu Leu Pro Tyr Ser Arg Arg Ile Val Ile
145                 150                 155                 160

Phe Asn Glu Val Cys Leu Ser Tyr Ile Tyr Lys His Ser Val Met Ile
            165                 170                 175

Leu Glu Arg Asp Arg Val Asn Asp Gly His Lys Asp Tyr Ile Glu Glu
            180                 185                 190

Lys Thr Lys Glu Lys Asn Lys Leu Lys Lys Glu Leu Glu Lys Cys Phe
            195                 200                 205

Pro Glu Gln Tyr Ser Leu Met Lys Lys Glu Glu Leu Ala Arg Ile Phe
            210                 215                 220

Asp Asn Ala Ser Thr Ile Ser Ser Lys Tyr Lys Leu Leu Val Asp Glu
225                 230                 235                 240

Ile Ser Asn Lys Ala Tyr Gly Thr Leu Glu Gly Pro Ala Ala Asp Asn
            245                 250                 255

Phe Asp His Phe Arg Asn Ile Trp Lys Ser Ile Val Leu Lys Asp Met
            260                 265                 270

Phe Ile Tyr Cys Asp Leu Leu Leu Gln His Leu Ile Tyr Lys Phe Tyr
            275                 280                 285

Tyr Asp Asn Thr Val Asn Asp Ile Lys Lys Asn Phe Asp Glu Ser Trp
            290                 295                 300

Thr Gln Thr Leu Lys Glu
305                 310
```

(2) INFORMATION FOR SEQ ID NO:20:

(i) SEQUENCE CHARACTERISTICS:
        (A) LENGTH: 367 amino acids

```
            (B) TYPE: amino acid
            (C) STRANDEDNESS:
            (D) TOPOLOGY: linear (xi) SEQUENCE DESCRIPTION: SEQ ID NO:20:

Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Ser Asp Thr Asp
                20                  25                  30

Pro Glu Ala Gly Gly Pro Ser Glu Ala Gly Gly Pro Ser Gly Thr Val
            35                  40                  45

Gly Pro Ser Glu Ala Gly Gly Pro Ser Glu Ala Gly Gly Pro Ser Gly
    50                  55                  60

Thr Gly Trp Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
                85                  90                  95

Trp Pro Ser Gly Thr Gly Trp Pro Ser Glu Ala Gly Trp Ser Ser Glu
                100                 105                 110

Arg Phe Gly Tyr Gln Leu Leu Pro Tyr Ser Arg Arg Ile Val Ile Phe
            115                 120                 125

Asn Glu Val Cys Leu Ser Tyr Ile Tyr Lys His Ser Val Met Ile Leu
    130                 135                 140

Glu Arg Asp Arg Val Asn Asp Gly His Lys Asp Tyr Ile Glu Glu Lys
145                 150                 155                 160

Thr Lys Glu Lys Asn Lys Leu Lys Lys Glu Leu Glu Lys Cys Phe Pro
                165                 170                 175

Glu Gln Tyr Ser Leu Met Lys Lys Glu Leu Ala Arg Ile Phe Asp
            180                 185                 190

Asn Ala Ser Thr Ile Ser Ser Lys Tyr Lys Leu Leu Val Asp Glu Ile
            195                 200                 205

Ser Asn Lys Ala Tyr Gly Thr Leu Glu Gly Pro Ala Ala Asp Asn Phe
    210                 215                 220

Asp His Phe Arg Asn Ile Trp Lys Ser Ile Val Leu Lys Asp Met Phe
225                 230                 235                 240

Ile Tyr Cys Asp Leu Leu Leu Gln His Leu Ile Tyr Lys Phe Tyr Tyr
                245                 250                 255

Asp Asn Thr Val Asn Asp Ile Lys Lys Asn Phe Asp Glu Ser Lys Ser
                260                 265                 270

Lys Ala Leu Val Leu Arg Asp Lys Ile Thr Lys Asp Gly Asp Tyr
    275                 280                 285

Asn Thr His Phe Glu Asp Met Ile Lys Glu Leu Asn Ser Ala Ala Glu
290                 295                 300

Glu Phe Asn Lys Ile Val Asp Ile Met Ile Ser Asn Ile Gly Asp Tyr
305                 310                 315                 320

Asp Glu Tyr Asp Ser Ile Ala Ser Phe Lys Pro Phe Leu Ser Met Ile
                325                 330                 335

Thr Glu Ile Thr Lys Ile Thr Lys Val Ser Asn Val Ile Ile Pro Gly
            340                 345                 350

Ile Lys Ala Leu Thr Leu Thr Val Phe Leu Ile Phe Ile Thr Lys
    355                 360                 365

(2) INFORMATION FOR SEQ ID NO:21:

(i) SEQUENCE CHARACTERISTICS:
```

(A) LENGTH: 492 amino acids
        (B) TYPE: amino acid
        (C) STRANDEDNESS:
        (D) TOPOLOGY: linear (xi) SEQUENCE DESCRIPTION: SEQ ID NO:21:

Met Tyr Lys Ile Lys Ile Ser Asp Tyr Ile Glu Phe Asp Asp Asn
1               5                   10                  15

Ala Lys Leu Pro Thr Asp Asn Val Ile Gly Ile Ser Ile Tyr Thr Cys
            20                  25                  30

Glu His Asn Asn Pro Val Leu Ile Glu Phe Tyr Val Ser Lys Lys Gly
            35                  40                  45

Ser Ile Cys Tyr Tyr Phe Tyr Ser Met Asn Asn Asp Thr Asn Lys Trp
50                      55                  60

Asn Asn His Lys Ile Lys Tyr Asp Lys Arg Phe Asn Glu His Thr Asp
65                  70                  75                  80

Met Asn Gly Ile His Tyr Tyr Ile Asp Gly Ser Leu Leu Ala Ser
                85                  90                  95

Gly Glu Val Thr Ser Asn Phe Arg Tyr Ile Ser Lys Glu Tyr Glu Tyr
            100                 105                 110

Glu His Thr Glu Leu Ala Lys Glu His Cys Lys Lys Glu Lys Cys Val
            115                 120                 125

Asn Val Asp Asn Ile Glu Asp Asn Asn Leu Lys Ile Tyr Ala Lys Gln
130                 135                 140

Phe Lys Ser Val Val Thr Thr Pro Ala Asp Val Ala Gly Val Ser Asp
145                 150                 155                 160

Gly Phe Phe Ile Arg Gly Gln Asn Leu Gly Ala Val Gly Ser Val Asn
                165                 170                 175

Glu Gln Pro Asn Thr Val Gly Met Ser Leu Glu Gln Phe Ile Lys Asn
            180                 185                 190

Glu Leu Tyr Ser Phe Ser Asn Glu Ile Tyr His Thr Ile Ser Ser Gln
            195                 200                 205

Ile Ser Asn Ser Phe Leu Ile Met Met Ser Asp Ala Ile Val Lys His
210                 215                 220

Asp Asn Tyr Ile Leu Lys Lys Glu Gly Glu Gly Cys Glu Gln Ile Tyr
225                 230                 235                 240

Asn Tyr Glu Glu Phe Ile Glu Lys Leu Arg Gly Ala Arg Ser Glu Gly
                245                 250                 255

Asn Asn Met Phe Gln Glu Ala Leu Ile Arg Phe Arg Asn Ala Ser Ser
            260                 265                 270

Glu Glu Met Val Asn Ala Ala Ser Tyr Leu Ser Ala Ala Leu Phe Arg
            275                 280                 285

Tyr Lys Glu Phe Asp Asp Glu Leu Phe Lys Lys Ala Asn Asp Asn Phe
290                 295                 300

Gly Arg Asp Asp Gly Tyr Asp Phe Asp Tyr Ile Asn Thr Lys Lys Glu
305                 310                 315                 320

Leu Val Ile Leu Ala Ser Val Leu Asp Gly Leu Asp Leu Ile Met Glu
                325                 330                 335

Arg Leu Ile Glu Asn Phe Ser Asp Val Asn Asn Thr Asp Asp Ile Lys
            340                 345                 350

Lys Ala Phe Asp Glu Cys Lys Ser Asn Ala Ile Ile Leu Lys Lys Lys
            355                 360                 365

Ile Leu Asp Asn Asp Glu Asp Tyr Lys Ile Asn Phe Arg Glu Met Val
370                 375                 380

```
Asn Glu Val Thr Cys Ala Asn Thr Lys Phe Glu Ala Leu Asn Asp Leu
385                 390                 395                 400

Ile Ile Ser Asp Cys Glu Lys Lys Gly Ile Lys Ile Asn Arg Asp Val
                405                 410                 415

Ile Ser Ser Tyr Lys Leu Leu Leu Ser Thr Ile Thr Tyr Ile Val Gly
                420                 425                 430

Ala Gly Val Glu Ala Val Thr Val Ser Val Ser Ala Thr Ser Asn Gly
            435                 440                 445

Thr Glu Ser Gly Gly Ala Gly Ser Gly Thr Gly Thr Ser Val Ser Ala
        450                 455                 460

Thr Ser Thr Leu Thr Gly Asn Gly Gly Thr Glu Ser Gly Gly Thr Ala
465                 470                 475                 480

Gly Thr Thr Thr Ser Ser Gly Thr Trp Phe Gly Lys
                485                 490
```

(2) INFORMATION FOR SEQ ID NO:22:

(i) SEQUENCE CHARACTERISTICS:
        (A) LENGTH: 138 amino acids
        (B) TYPE: amino acid
        (C) STRANDEDNESS:
        (D) TOPOLOGY: linear (xi) SEQUENCE DESCRIPTION: SEQ ID NO:22:

```
Ser Leu Gly Gln Pro Ala Ser Leu Gly Gln Pro Ala Ser Leu Gly Gln
1               5                   10                  15

Pro Ala Ser Leu Gly Gln Pro Ala Ser Leu Gly Gln Pro Ala Ser Leu
            20                  25                  30

Gly Gln Pro Val Pro Leu Gly Pro Pro Ala Ser Leu Gly Pro Pro Ala
        35                  40                  45

Ser Leu Gly Pro Pro Ala Ser Leu Gly Gln Pro Val Pro Leu Gly Pro
50                  55                  60

Pro Ala Ser Leu Gly Pro Pro Ala Ser Leu Gly Pro Pro Ala Ser Leu
65                  70                  75                  80

Gly Pro Pro Ala Ser Leu Gly Pro Pro Ala Ser Leu Gly Pro Pro Ala
                85                  90                  95

Ser Leu Gly Pro Pro Ala Ser Leu Gly Pro Pro Ala Ser Leu Gly Pro
            100                 105                 110

Thr Val Pro Leu Gly Pro Pro Ala Ser Arg Ser Val Ser Pro Ala Lys
            115                 120                 125

Thr Ala Pro Leu Ile Lys Lys Ser Val Ile
            130                 135
```

(2) INFORMATION FOR SEQ ID NO:23:

(i) SEQUENCE CHARACTERISTICS:
        (A) LENGTH: 303 amino acids
        (B) TYPE: amino acid
        (C) STRANDEDNESS:
        (D) TOPOLOGY: linear (xi) SEQUENCE DESCRIPTION: SEQ ID NO:23:

```
Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Gly Asp Thr Asp
            20                  25                  30

Arg Glu Ala Gly Gly Pro Ser Gly Thr Val Gly Pro Ser Glu Ala Gly
        35                  40                  45
```

-continued

Gly Pro Ser Glu Ala Gly Gly Pro Ser Glu Ala Gly Gly Pro Ser Glu
 50                  55                  60

Ala Gly Gly Pro Ser Glu Ala Gly Gly Pro Ser Glu Ala Gly Gly Pro
 65                  70                  75                  80

Ser Glu Ala Gly Gly Pro Ser Glu Ala Gly Gly Pro Ser Gly Thr Gly
                 85                  90                  95

Trp Pro Ser Glu Ala Gly Trp Pro Ser Glu Ala Gly Trp Pro Ser Glu
                100                 105                 110

Ala Gly Trp Pro Ser Glu Ala Gly Trp Pro Ser Glu Ala Gly Trp Pro
            115                 120                 125

Ser Glu Arg Phe Gly Tyr Gln Leu Leu Trp Tyr Ser Arg Arg Ile Val
130                 135                 140

Ile Phe Asn Glu Ile Tyr Leu Ser His Ile Tyr Glu His Ser Val Met
145                 150                 155                 160

Ile Leu Glu Arg Asp Arg Val Asn Asp Gly His Lys Asp Tyr Ile Glu
                165                 170                 175

Glu Lys Thr Lys Glu Lys Asn Lys Leu Lys Lys Glu Leu Glu Lys Cys
                180                 185                 190

Phe Pro Glu Gln Tyr Ser Leu Met Lys Lys Glu Glu Leu Ala Arg Ile
            195                 200                 205

Ile Asp Asn Ala Ser Thr Ile Ser Ser Lys Tyr Lys Leu Leu Val Asp
210                 215                 220

Glu Ile Ser Asn Lys Ala Tyr Gly Thr Leu Glu Gly Pro Ala Ala Asp
225                 230                 235                 240

Asp Phe Asp His Phe Arg Asn Ile Trp Lys Ser Ile Val Pro Lys Asn
                245                 250                 255

Met Phe Leu Tyr Cys Asp Leu Leu Lys His Leu Ile Arg Lys Phe
                260                 265                 270

Tyr Cys Asp Asn Thr Ile Asn Asp Ile Lys Lys Asn Phe Asp Asp Ile
            275                 280                 285

Glu Lys Leu Gly Cys Phe Gln Ala Arg Ser Phe Leu Pro Val Asn
290                 295                 300

(2) INFORMATION FOR SEQ ID NO:24:

(i) SEQUENCE CHARACTERISTICS:
        (A) LENGTH: 592 amino acids
        (B) TYPE: amino acid
        (C) STRANDEDNESS: single
        (D) TOPOLOGY: linear (xi) SEQUENCE DESCRIPTION: SEQ ID NO:24:

Met Met Lys Phe Asn Ile Asp Lys Ile Ile Leu Ile Asn Leu Ile Val
1                   5                  10                  15

Leu Leu Asn Arg Asn Val Val Tyr Cys Val Asp Thr Asn Asn Ser Ser
                20                  25                  30

Leu Ile Glu Ser Gln Pro Val Thr Thr Asn Ile Asp Thr Asp Asn Thr
            35                  40                  45

Ile Thr Thr Asn Lys Tyr Thr Gly Thr Ile Ile Asn Ala Asn Ile Val
        50                  55                  60

Glu Tyr Arg Glu Phe Glu Asp Glu Pro Leu Thr Ile Gly Phe Arg Tyr
65                  70                  75                  80

Thr Ile Asp Lys Ser Gln Gln Asn Lys Leu Ser His Pro Asn Lys Ile
                85                  90                  95

Asp Lys Ile Lys Phe Ser Asp Tyr Ile Ile Glu Phe Asp Asp Asn Ala
            100                 105                 110

```
Lys Leu Pro Thr Asp Asn Val Ile Cys Ile Ser Ile Tyr Thr Cys Lys
        115                 120                 125
His Asn Asn Pro Val Leu Ile Arg Phe Ser Cys Ser Ile Glu Lys Tyr
        130                 135                 140
Tyr Tyr His Tyr Phe Tyr Ser Met Asn Asn Asp Thr Asn Lys Trp Asn
145                 150                 155                 160
Asn His Lys Leu Lys Tyr Asp Lys Thr Tyr Asn Glu Tyr Thr Asp Asn
                165                 170                 175
Asn Gly Val Asn Tyr Tyr Lys Ile Tyr Tyr Ser Asp Lys Gln Asn Ser
                180                 185                 190
Pro Thr Asn Gly Asn Glu Tyr Glu Asp Val Ala Leu Ala Arg Ile His
            195                 200                 205
Cys Asn Glu Glu Arg Cys Ala Asn Val Lys Val Asp Lys Ile Lys Tyr
            210                 215                 220
Lys Asn Leu Glu Ile Tyr Val Lys Gln Leu Gly Thr Ile Ile Asn Ala
225                 230                 235                 240
Asn Ile Val Glu Tyr Leu Val Phe Glu Asp Glu Pro Leu Thr Ile Gly
                245                 250                 255
Phe Arg Tyr Thr Ile Asp Lys Ser Gln Gln Asn Glu Leu Ser His Pro
            260                 265                 270
Asn Lys Ile Tyr Lys Ile Lys Phe Ser Asp Tyr Ile Ile Glu Phe Asp
        275                 280                 285
Asp Asp Ala Lys Leu Thr Thr Ile Gly Thr Val Glu Asp Ile Thr Ile
        290                 295                 300
Tyr Thr Cys Lys His Asn Asn Pro Val Leu Ile Arg Phe Ser Cys Ser
305                 310                 315                 320
Ile Glu Lys Tyr Tyr Tyr Tyr Phe Tyr Ser Met Asn Asn Asn Thr
                325                 330                 335
Asn Lys Trp Asn Asn His Asn Leu Lys Tyr Asp Asn Arg Phe Lys Glu
            340                 345                 350
His Ser Asp Lys Asn Gly Ile Asn Tyr Tyr Glu Ile Ser Ala Phe Lys
            355                 360                 365
Trp Ser Phe Ser Cys Phe Phe Val Asn Lys Tyr Glu His Lys Glu Leu
        370                 375                 380
Ala Arg Ile His Cys Asn Glu Glu Arg Cys Ala Asn Val Lys Val Asp
385                 390                 395                 400
Lys Ile Lys Tyr Lys Asn Leu Glu Ile Tyr Val Lys Gln Leu Gly Thr
                405                 410                 415
Ile Ile Asn Ala Asn Ile Val Glu Tyr Leu Val Phe Glu Asp Glu Pro
            420                 425                 430
Leu Thr Ile Gly Phe Arg Tyr Thr Ile Asp Lys Ser Gln Gln Asn Glu
            435                 440                 445
Leu Ser His Pro Asn Lys Ile Tyr Lys Ile Lys Phe Ser Asp Tyr Ile
        450                 455                 460
Ile Glu Phe Asp Asp Asp Ala Lys Leu Thr Thr Ile Gly Thr Val Glu
465                 470                 475                 480
Asp Ile Thr Ile Tyr Thr Cys Lys His Asn Asn Pro Val Leu Ile Arg
                485                 490                 495
Phe Ser Cys Ser Ile Glu Lys Tyr Tyr Tyr Tyr Phe Tyr Ser Met
            500                 505                 510
Asn Asn Asn Thr Asn Lys Trp Asn Asn His Asn Leu Lys Tyr Asp Asn
        515                 520                 525
```

```
Arg Phe Lys Glu His Ser Asp Lys Asn Gly Ile Asn Tyr Tyr Glu Ile
        530                 535                 540

Ser Ala Phe Lys Trp Ser Phe Ser Cys Phe Val Asn Lys Tyr Glu
545                 550                 555                 560

His Lys Glu Leu Ala Arg Ile His Cys Asn Glu Lys Cys Val Asn
                565                 570                 575

Val Lys Val Asp Asn Ile Gly Asn Lys Asn Leu Glu Ile Tyr Val Lys
            580                 585                 590
```

(2) INFORMATION FOR SEQ ID NO:25:

(i) SEQUENCE CHARACTERISTICS:
        (A) LENGTH: 463 amino acids
        (B) TYPE: amino acid
        (C) STRANDEDNESS: single
        (D) TOPOLOGY: linear (xi) SEQUENCE DESCRIPTION: SEQ ID NO:25:

```
Ile Ile Met Lys Ile Asn Ile Asp Asn Ile Ile Leu Ile Asn Leu Ile
1               5                   10                  15

Ile Leu Leu Asn Arg Asn Val Val Tyr Cys Val Asp Lys Asn Asp Val
            20                  25                  30

Ser Leu Trp Lys Ser Lys Pro Ile Thr Thr Val Ser Thr Thr Asn Asp
        35                  40                  45

Thr Ile Thr Asn Lys Tyr Thr Ser Thr Val Ile Asn Ala Asn Phe Ala
    50                  55                  60

Ser Tyr Arg Glu Phe Glu Asp Arg Glu Pro Leu Thr Ile Gly Phe Glu
65                  70                  75                  80

Tyr Met Ile Asp Lys Ser Gln Gln Asp Lys Leu Ser His Pro Asn Lys
                85                  90                  95

Ile Asp Lys Ile Lys Ile Ser Asp Tyr Ile Ile Glu Phe Asp Asp Asn
            100                 105                 110

Ala Lys Leu Pro Thr Gly Ser Val Asn Asp Ile Ser Ile Ile Thr Cys
        115                 120                 125

Lys His Asn Asn Pro Val Leu Ile Arg Phe Ser Cys Leu Ile Glu Gly
    130                 135                 140

Ser Ile Cys Tyr Tyr Phe Tyr Leu Leu Asn Asn Asp Thr Asn Lys Trp
145                 150                 155                 160

Asn Asn His Lys Leu Lys Tyr Asp Lys Thr Tyr Asn Glu His Thr Asp
                165                 170                 175

Asn Asn Gly Ile Asn Tyr Tyr Lys Ile Asp Tyr Ser Glu Ser Thr Glu
            180                 185                 190

Pro Thr Thr Glu Ser Thr Thr Cys Phe Cys Phe Arg Lys Lys Asn His
        195                 200                 205

Lys Ser Glu Arg Lys Glu Leu Glu Asn Tyr Lys Tyr Glu Gly Thr Glu
    210                 215                 220

Leu Ala Arg Ile His Cys Asn Lys Gly Lys Cys Val Lys Leu Gly Asp
225                 230                 235                 240

Ile Lys Ile Lys Asp Lys Asn Leu Glu Ile Tyr Val Lys Gln Leu Met
                245                 250                 255

Ser Val Asn Thr Pro Val Asn Phe Asp Asn Pro Thr Ser Ile Asn Leu
            260                 265                 270

Pro Thr Val Ser Thr Thr Asn Asp Thr Ile Thr Asn Lys Tyr Thr Gly
        275                 280                 285

Thr Ile Ile Asn Ala Asn Ile Val Glu Tyr Cys Glu Phe Glu Asp Glu
    290                 295                 300
```

```
Pro Leu Thr Ile Gly Phe Arg Tyr Thr Ile Asp Lys Ser Gln Gln Asn
305                 310                 315                 320

Lys Leu Ser His Pro Asn Lys Ile Asp Lys Ile Lys Phe Phe Asp Tyr
            325                 330                 335

Ile Ile Glu Phe Asp Asp Val Lys Leu Pro Thr Ile Gly Thr Val
            340                 345                 350

Asn Ile Ile Tyr Ile Tyr Thr Cys Glu His Asn Asn Pro Val Leu Val
            355                 360                 365

Glu Phe Ile Val Ser Ile Glu Glu Ser Tyr Tyr Phe Tyr Phe Tyr Ser
370                 375                 380

Met Asn Asn Thr Asn Lys Trp Asn His Lys Leu Lys Tyr Asp
385                 390                 395                 400

Lys Arg Phe Lys Lys Tyr Thr Lys Asn Gly Ile Asn Cys Tyr Glu Tyr
            405                 410                 415

Val Leu Arg Lys Cys Ser Ser Tyr Thr Arg Lys Asn Glu Tyr Glu His
            420                 425                 430

Lys Glu Leu Ala Arg Ile His Cys Asn Glu Glu Lys Cys Val Asn Val
            435                 440                 445

Lys Val Asp Asn Ile Glu Lys Lys Asn Leu Glu Ile Tyr Val Lys
450                 455                 460

(2) INFORMATION FOR SEQ ID NO:26:

(i) SEQUENCE CHARACTERISTICS:
        (A) LENGTH: 297 amino acids
        (B) TYPE: amino acid
        (C) STRANDEDNESS:
        (D) TOPOLOGY: linear (xi) SEQUENCE DESCRIPTION: SEQ ID NO:26:

Arg Ala Ala Arg Ala Asp Tyr Tyr Lys Tyr Leu Val Asp Glu Tyr Ser
1               5                   10                  15

Ser Pro Arg Glu Glu Arg Glu Leu Ala Arg Val His Cys Asn Glu Glu
            20                  25                  30

Lys Cys Val Lys Leu Asp Gly Ile Lys Phe Lys Asp Lys Asn Leu Glu
            35                  40                  45

Ile Tyr Val Lys Gln Leu Met Ser Val Asn Thr Pro Val Val Phe Asp
50                  55                  60

Asn Asn Thr Leu Ile Asn Pro Thr Ser Ser Gly Ala Thr Asp Asp
65                  70                  75                  80

Ile Thr Tyr Glu Leu Ser Val Glu Ser Gln Pro Val Pro Thr Asn Ile
            85                  90                  95

Asp Thr Gly Asn Asn Ile Thr Thr Asn Thr Ser Asn Asn Leu Ile
            100                 105                 110

Lys Ala Lys Phe Leu Tyr Asn Phe Asn Leu Pro Gly Lys Pro Ser Thr
            115                 120                 125

Gly Leu Phe Glu Tyr Thr Ile Asp Lys Ser Glu Gln Asn Lys Leu Ser
130                 135                 140

His Pro Asn Lys Ile Asp Lys Ile Lys Phe Ser Asp Tyr Ile Ile Glu
145                 150                 155                 160

Phe Asp Asp Asp Ala Lys Leu Pro Thr Ile Gly Thr Val Asn Ile Ile
                165                 170                 175

Ser Ile Ile Thr Cys Lys His Asn Asn Pro Val Leu Val Glu Phe Ile
            180                 185                 190

Val Ser Thr Glu Ile Tyr Cys Tyr Tyr Asn Tyr Phe Tyr Ser Met Asn
```

```
                195                 200                 205
Asn Asn Thr Asn Lys Trp Asn Asn His Lys Leu Lys Tyr Asp Lys Arg
    210                 215                 220

Tyr Lys Glu Glu Tyr Thr Asp Asp Asn Gly Ile Asn Tyr Tyr Lys Leu
225                 230                 235                 240

Asn Asp Ser Glu Pro Thr Glu Ser Thr Glu Ser Thr Thr Cys Phe Cys
                245                 250                 255

Phe Arg Lys Lys Asn His Lys Tyr Glu Asn Glu Arg Thr Ala Leu Ala
                260                 265                 270

Lys Glu His Cys Asn Glu Glu Arg Cys Val Lys Val Asp Asn Ile Lys
                275                 280                 285

Asp Asn Asn Leu Glu Ile Tyr Leu Lys
                290                 295

(2) INFORMATION FOR SEQ ID NO:27:

(i) SEQUENCE CHARACTERISTICS:
        (A) LENGTH: 121 amino acids
        (B) TYPE: amino acid
        (C) STRANDEDNESS:
        (D) TOPOLOGY: linear (xi) SEQUENCE DESCRIPTION: SEQ ID NO:27:

Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Ser Asp Thr Asp
                20                  25                  30

Pro Glu Ala Gly Gly Pro Ser Glu Ala Gly Gly Pro Ser Glu Ala Gly
                35                  40                  45

Gly Pro Ser Gly Thr Val Gly Pro Ser Glu Ala Gly Gly Pro Ser Glu
                50                  55                  60

Ala Gly Gly Pro Ser Gly Thr Gly Trp Pro Ser Glu Ala Gly Gly Pro
65                  70                  75                  80

Ser Glu Ala Gly Gly Pro Ser Gly Thr Gly Trp Pro Ser Glu Ala Gly
                85                  90                  95

Trp Ser Ser Glu Arg Phe Gly Tyr Gln Leu Leu Pro Tyr Ser Arg Arg
                100                 105                 110

Ile Val Thr Phe Asn Glu Val Cys Leu
                115                 120

(2) INFORMATION FOR SEQ ID NO:28:

(i) SEQUENCE CHARACTERISTICS:
        (A) LENGTH: 267 amino acids
        (B) TYPE: amino acid
        (C) STRANDEDNESS:
        (D) TOPOLOGY: linear (xi) SEQUENCE DESCRIPTION: SEQ ID NO:28:

Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Ser Asp Thr Asp
                20                  25                  30

Pro Glu Ala Gly Gly Pro Ser Gly Thr Val Gly Pro Ser Glu Ala Gly
                35                  40                  45

Gly Pro Ser Glu Ala Gly Gly Pro Ser Gly Thr Gly Trp Pro Ser Glu
                50                  55                  60

Ala Gly Gly Pro Ser Glu Ala Gly Gly Pro Ser Gly Thr Gly Trp Pro
```

```
                65                  70                  75                  80
Ser Glu Ala Gly Trp Ser Glu Arg Phe Gly Tyr Gln Leu Leu Pro
                    85                  90                  95

Tyr Ser Arg Arg Ile Val Thr Phe Asn Glu Val Cys Leu Ser Tyr Ile
                100                 105                 110

Tyr Lys His Ser Val Met Ile Leu Glu Arg Asp Arg Val Asn Asp Gly
            115                 120                 125

His Lys Asp Tyr Ile Glu Glu Lys Thr Lys Glu Lys Asn Lys Leu Lys
    130                 135                 140

Lys Glu Leu Glu Lys Cys Phe Pro Glu Gln Tyr Ser Leu Met Lys Lys
145                 150                 155                 160

Glu Glu Leu Ala Arg Ile Phe Asp Asn Ala Ser Thr Ile Ser Ser Lys
                165                 170                 175

Tyr Lys Leu Leu Val Asp Glu Ile Ser Asn Lys Ala Tyr Gly Thr Leu
                180                 185                 190

Glu Gly Pro Ala Ala Asp Asn Phe Asp His Phe Arg Asn Ile Trp Lys
            195                 200                 205

Ser Ile Val Leu Lys Asp Met Phe Ile Tyr Cys Asp Leu Leu Leu Gln
    210                 215                 220

His Leu Ile Tyr Lys Phe Tyr Tyr Asp Asn Thr Ile Asn Asp Ile Lys
225                 230                 235                 240

Lys Asn Phe Asp Glu Ser Lys Ser Lys Ala Leu Val Leu Arg Asp Lys
                245                 250                 255

Ile Thr Lys Lys Asp Val Tyr Val Asn Asp His
                260                 265

(2) INFORMATION FOR SEQ ID NO:29:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO:29:

Ala Trp Thr Phe Ser Val Leu Glu Leu Gln Glu Phe Ser Tyr Thr Val
1               5                   10                  15

(2) INFORMATION FOR SEQ ID NO:30:

(i) SEQUENCE CHARACTERISTICS:
        (A) LENGTH: 465 amino acids
        (B) TYPE: amino acid
        (C) STRANDEDNESS:
        (D) TOPOLOGY: linear (xi) SEQUENCE DESCRIPTION: SEQ ID NO:30:

Met Leu Thr Phe Gly Asn Ile Arg Phe His Asn Ile Asn Leu Pro Pro
1               5                   10                  15

Phe Ser Leu Gly Ile Ile His Ser Ile Thr Val Glu Lys Ala Ile Asn
                20                  25                  30

Ser Glu Asp Phe Asp Gly Ile Gln Thr Leu Leu Gln Val Ser Ile Ile
            35                  40                  45

Ala Ser Tyr Gly Pro Ser Gly Asp Tyr Ser Ser Phe Val Phe Thr Pro
    50                  55                  60

Val Val Thr Ala Asp Thr Asn Val Phe Tyr Lys Leu Glu Thr Asp Phe
65                  70                  75                  80

Lys Leu Asp Val Asp Val Ile Thr Lys Thr Ser Leu Glu Leu Pro Thr
```

-continued

```
                85                  90                  95
Ser Val Pro Gly Phe His Tyr Thr Glu Thr Ile Tyr Gln Gly Thr Glu
                   100                 105                 110

Leu Ser Lys Phe Ser Lys Pro Gln Cys Lys Leu Asn Asp Pro Pro Ile
        115                 120                 125

Thr Thr Gly Ser Gly Leu Gln Ile Ile His Asp Gly Leu Asn Asn Ser
    130                 135                 140

Thr Ile Ile Thr Asn Lys Glu Val Asn Val Asp Gly Thr Asp Leu Val
145                 150                 155                 160

Phe Phe Glu Leu Leu Pro Pro Ser Asp Gly Ile Pro Thr Leu Arg Ser
                165                 170                 175

Lys Leu Phe Pro Val Leu Lys Ser Ile Pro Met Ile Ser Thr Gly Val
                180                 185                 190

Asn Glu Leu Leu Leu Glu Val Leu Glu Asn Pro Ser Phe Pro Ser Ala
                195                 200                 205

Ile Ser Asn Tyr Thr Gly Leu Thr Gly Arg Leu Asn Lys Leu Leu Thr
                210                 215                 220

Val Leu Asp Gly Ile Val Asp Ser Ala Ile Ser Val Lys Thr Thr Glu
225                 230                 235                 240

Thr Val Pro Asp Asp Ala Glu Thr Ser Ile Ser Ser Leu Lys Ser Leu
                245                 250                 255

Ile Lys Ala Ile Arg Asp Asn Ile Thr Thr Thr Arg Asn Glu Val Thr
                260                 265                 270

Lys Asp Asp Val Tyr Ala Leu Lys Lys Ala Leu Thr Cys Leu Thr Thr
                275                 280                 285

His Leu Ile Tyr His Ser Lys Val Asp Gly Ile Ser Phe Asp Met Leu
                290                 295                 300

Gly Thr Gln Lys Asn Lys Ser Ser Pro Leu Gly Lys Ile Gly Thr Ser
305                 310                 315                 320

Met Asp Asp Ile Ile Ala Met Phe Ser Asn Pro Asn Met Tyr Leu Val
                325                 330                 335

Lys Val Ala Tyr Leu Gln Ala Ile Glu His Ile Phe Leu Ile Ser Thr
                340                 345                 350

Lys Tyr Asn Asp Ile Phe Asp Tyr Thr Ile Asp Phe Ser Lys Arg Glu
                355                 360                 365

Ala Thr Asp Ser Gly Ser Phe Thr Asp Ile Leu Leu Gly Asn Lys Val
    370                 375                 380

Lys Glu Ser Leu Ser Phe Ile Glu Gly Leu Ile Ser Asp Ile Lys Ser
385                 390                 395                 400

His Ser Leu Lys Ala Gly Val Thr Gly Gly Ile Ser Ser Ser Ser Leu
                405                 410                 415

Phe Asp Glu Ile Phe Asp Glu Leu Asn Leu Asp Gln Ala Thr Ile Arg
                420                 425                 430

Thr Leu Val Ala Pro Leu Asp Trp Pro Leu Ile Ser Asp Lys Ser Leu
            435                 440                 445

His Pro Ser Leu Lys Met Val Val Leu Pro Gly Phe Phe Ile Val
            450                 455                 460

Pro
465
```

(2) INFORMATION FOR SEQ ID NO:31:

(i) SEQUENCE CHARACTERISTICS:
        (A) LENGTH: 128 amino acids (B) TYPE: amino acid
        (C) STRANDEDNESS:
        (D) TOPOLOGY: linear (xi) SEQUENCE DESCRIPTION: SEQ ID NO:31:

```
Leu Trp Phe Ile Lys Met Val Ser Phe Lys Ser Ile Leu Val Pro Tyr
1               5                  10                  15

Ile Thr Leu Phe Leu Met Ser Gly Ala Val Phe Ala Ser Asp Thr Asp
                20                  25                  30

Pro Glu Ala Gly Gly Pro Ser Glu Ala Gly Gly Pro Ser Gly Thr Val
                35                  40                  45

Gly Pro Ser Glu Ala Gly Gly Pro Ser Glu Ala Gly Gly Pro Ser Gly
                50                  55                  60

Thr Gly Trp Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
                    85                  90                  95

Trp Pro Ser Gly Thr Gly Trp Pro Ser Glu Ala Gly Trp Ser Ser Glu
                    100                 105                 110

Arg Phe Gly Tyr Gln Leu Leu Pro Tyr Ser Arg Arg Ile Val Ile Phe
                    115                 120                 125
```

(2) INFORMATION FOR SEQ ID NO:32:

(i) SEQUENCE CHARACTERISTICS:
        (A) LENGTH: 245 amino acids
        (B) TYPE: amino acid
        (C) STRANDEDNESS:
        (D) TOPOLOGY: linear (xi) SEQUENCE DESCRIPTION: SEQ ID NO:32:

```
Gln Glu Cys Cys Leu Val Val Lys Asp Lys Val Ile Arg His Ala Ala
1               5                  10                  15

Phe Ala Ala Thr Ile Ile Ile Arg Arg Arg Arg Val Ser Phe Ile Ile
                20                  25                  30

Leu Gly Leu Ile Ile Ala Thr Met Thr Pro Phe Phe Thr Lys Val Phe
                35                  40                  45

Phe Phe Gln Arg Cys Leu Ser Ile Met Arg Phe Tyr Ser Ser Leu Pro
                50                  55                  60

Thr Phe Ile Leu Ile Glu Ile Ala Met Leu Phe Phe Met Ser Val Thr
65                  70                  75                  80

Cys Phe Leu Arg Cys Leu Ser Ile Ile Arg Phe Tyr Ser Ser Ile Ser
                    85                  90                  95

Thr Phe Ile Leu Ile Asp Phe Val Met Pro Phe Phe Thr Leu Phe Thr
                    100                 105                 110

Tyr Phe Leu Arg Cys Leu Ser Ile Met Arg Phe Ser Phe Ser Leu Leu
                    115                 120                 125

Thr Phe Ile Arg Ile Asp Phe Val Met Pro Phe Phe Met Ser Val Thr
                    130                 135                 140

Cys Phe Leu Arg Cys Leu Ser Ile Ile Arg Phe Tyr Ser Ser Ile Ser
145                 150                 155                 160

Thr Phe Ile Leu Ile Asp Phe Val Met Pro Phe Phe Thr Leu Phe Thr
                    165                 170                 175

Tyr Phe Leu Arg Cys Leu Ser Ile Ile Arg Phe Tyr Ser Ser Ile Ser
                    180                 185                 190

Thr Phe Ile Leu Ile Asp Phe Val Met Pro Phe Phe Thr Leu Phe Thr
                    195                 200                 205
```

```
Tyr Phe Leu Arg Cys Leu Ser Ile Met Arg Phe Ser Phe Ser Leu Leu
    210                 215                 220

Thr Phe Ile Arg Ile Gly Phe Ala Met Pro Phe Phe Thr Leu Phe Ile
225                 230                 235                 240

Tyr Phe Leu Cys Arg
                245

(2) INFORMATION FOR SEQ ID NO:33:

(i) SEQUENCE CHARACTERISTICS:
        (A) LENGTH: 293 amino acids
        (B) TYPE: amino acid
        (C) STRANDEDNESS:
        (D) TOPOLOGY: linear (xi) SEQUENCE DESCRIPTION: SEQ ID NO:33:

Thr Ala Phe Ala Ala Phe Leu Ala Phe Gly Asn Ile Ser Pro Val Leu
1               5                   10                  15

Ser Ala Gly Gly Ser Gly Gly Asn Gly Gly Asn Gly Gly Gly His Gln
                20                  25                  30

Glu Gln Asn Asn Ala Asn Asp Ser Ser Asn Pro Thr Gly Ala Gly Gly
            35                  40                  45

Gln Pro Asn Asn Glu Ser Lys Lys Ala Val Lys Leu Asp Leu Asp
        50                  55                  60

Leu Met Lys Glu Thr Lys Asn Val Cys Thr Thr Val Asn Thr Lys Leu
65                  70                  75                  80

Val Gly Lys Ala Lys Ser Lys Leu Asn Lys Leu Glu Gly Glu Ser His
                85                  90                  95

Lys Glu Tyr Val Ala Glu Lys Thr Lys Glu Ile Asp Glu Lys Asn Lys
            100                 105                 110

Lys Phe Asn Glu Asn Leu Val Lys Ile Glu Lys Lys Lys Lys Ile Lys
        115                 120                 125

Val Pro Ala Asp Thr Gly Ala Glu Val Asp Ala Val Asp Asp Gly Val
    130                 135                 140

Ala Gly Ala Leu Ser Asp Leu Ser Ser Asp Ile Ser Ala Ile Lys Thr
145                 150                 155                 160

Leu Thr Asp Asp Val Ser Glu Lys Val Ser Glu Asn Leu Lys Asp Asp
                165                 170                 175

Glu Ala Ser Ala Thr Glu His Thr Asp Ile Lys Glu Lys Ala Thr Leu
            180                 185                 190

Leu Gln Glu Ser Cys Asn Gly Ile Gly Thr Ile Leu Asp Lys Leu Ala
        195                 200                 205

Glu Tyr Leu Asn Asn Asp Thr Thr Gln Asn Ile Lys Lys Glu Phe Asp
    210                 215                 220

Glu Arg Lys Lys Asn Leu Thr Ser Leu Lys Thr Lys Val Glu Asn Lys
225                 230                 235                 240

Asp Glu Asp Tyr Val Asp Val Thr Met Thr Ser Lys Thr Asp Leu Ile
                245                 250                 255

Ile His Cys Leu Thr Cys Thr Asn Asp Ala His Gly Leu Phe Asp Phe
            260                 265                 270

Glu Ser Lys Ser Leu Ile Lys Gln Thr Phe Lys Leu Arg Ser Lys Asp
        275                 280                 285

Glu Gly Glu Leu Cys
    290
```

-continued (2) INFORMATION FOR SEQ ID NO:34:

(i) SEQUENCE CHARACTERISTICS:
        (A) LENGTH: 431 amino acids
        (B) TYPE: amino acid
        (C) STRANDEDNESS:
        (D) TOPOLOGY: linear (xi) SEQUENCE DESCRIPTION: SEQ ID NO:34:

```
Gly Pro Lys Met Lys Val Asn Ser Ala Asn Leu Asp Phe Arg Trp Ala
 1               5                  10                  15

Met Tyr Met Leu Asn Ser Lys Ile His Leu Ile Glu Ser Ser Leu Ile
            20                  25                  30

Asp Asn Phe Thr Leu Asp Asn Pro Ser Ala Tyr Glu Ile Leu Arg Val
        35                  40                  45

Ser Tyr Asn Ser Asn Glu Phe Gln Val Gln Ser Pro Gln Asn Ile Asn
50                  55                  60

Asn Glu Met Glu Ser Ser Thr Pro Glu Ser Asn Ile Ile Trp Val Val
65                  70                  75                  80

His Ser Asp Val Ile Met Lys Arg Phe Asn Cys Lys Asn Arg Lys Ser
                85                  90                  95

Leu Ser Thr His Ser Leu Thr Glu Asn Asp Ile Leu Lys Phe Gly Arg
            100                 105                 110

Ile Glu Leu Ser Val Lys Cys Ile Ile Met Gly Ala Gly Ile Thr Ala
        115                 120                 125

Ser Asp Leu Asn Leu Lys Gly Leu Gly Phe Ile Ser Pro Asp Lys Gln
    130                 135                 140

Ser Thr Asn Val Cys Asn Tyr Phe Glu Asp Met His Glu Ser Tyr His
145                 150                 155                 160

Ile Leu Asp Thr Gln Arg Ala Ser Asp Cys Val Ser Asp Asp Gly Ala
                165                 170                 175

Asp Ile Asp Ile Ser Asn Phe Asp Met Val Gln Asp Gly Asn Ile Asn
            180                 185                 190

Ser Val Asp Ala Asp Ser Glu Thr Cys Met Ala Asn Ser Gly Val Thr
        195                 200                 205

Val Asn Asn Thr Glu Asn Val Ser Asn Ser Glu Asn Phe Gly Lys Leu
    210                 215                 220

Lys Ser Leu Val Ser Thr Thr Thr Pro Leu Cys Arg Ile Cys Leu Cys
225                 230                 235                 240

Gly Glu Ser Asp Pro Gly Pro Leu Val Thr Pro Cys Asn Cys Lys Gly
                245                 250                 255

Ser Leu Asn Tyr Val His Leu Glu Cys Leu Arg Thr Trp Ile Lys Gly
            260                 265                 270

Arg Leu Ser Ile Val Lys Asp Asp Ala Ser Phe Phe Trp Lys Glu
        275                 280                 285

Leu Ser Cys Glu Leu Cys Gly Lys Pro Tyr Pro Ser Val Leu Gln Val
    290                 295                 300

Asp Asp Thr Glu Thr Asn Leu Met Asp Ile Lys Lys Pro Asp Ala Pro
305                 310                 315                 320

Tyr Val Val Leu Glu Met Arg Ser Asn Ser Gly Asp Gly Cys Phe Val
                325                 330                 335

Val Ser Val Ala Lys Asn Lys Ala Ile Ile Gly Arg Gly His Glu Ser
            340                 345                 350

Asp Val Arg Leu Ser Asp Ile Ser Val Ser Arg Met His Ala Ser Leu
        355                 360                 365
```

```
Glu Leu Asp Gly Gly Lys Val Val Ile His Asp Gln Gln Ser Lys Phe
    370                 375                 380

Gly Thr Leu Val Arg Ala Lys Ala Pro Phe Ser Met Pro Ile Lys Gly
385                 390                 395                 400

Pro Ile Cys Leu Gln Val Ser Ile Phe Phe Leu Asn Leu Lys Ile Ser
                405                 410                 415

Thr His Ser Leu Thr Met Glu Arg Gly Met Glu His Val Leu Leu
                420                 425                 430
```

(2) INFORMATION FOR SEQ ID NO:35:

(i) SEQUENCE CHARACTERISTICS:
        (A) LENGTH: 6 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 1
        (D) OTHER INFORMATION: /note= "Residue can be either GLU
            or GLY"

(ix) FEATURE:
        (A) NAME/KEY: Modified-site
        (B) LOCATION: 2
        (D) OTHER INFORMATION: /note= "Residue can be either ALA
            or THR"

(ix) FEATURE:
        (A) NAME/KEY: Modified-site
        (B) LOCATION: 3
        (D) OTHER INFORMATION: /note= "Residue can be either GLY
            or VAL"

(ix) FEATURE:
        (A) NAME/KEY: Modified-site
        (B) LOCATION: 4
        (D) OTHER INFORMATION: /note= "Residue can be either TRP
            or GLY"

(ix) FEATURE:
        (A) NAME/KEY: Modified-site
        (B) LOCATION: 5
        (D) OTHER INFORMATION: /note= "Residue can be either PRO
            or SER"

(xi) SEQUENCE DESCRIPTION: SEQ ID NO:35:

```
Xaa Xaa Xaa Xaa Xaa Ser
1                   5
```

(2) INFORMATION FOR SEQ ID NO:36:

(i) SEQUENCE CHARACTERISTICS:
        (A) LENGTH: 32 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 6
        (D) OTHER INFORMATION: /note= "Residue can be either Met
            or Ile"

(ix) FEATURE:
        (A) NAME/KEY: Modified-site
        (B) LOCATION: 9
        (D) OTHER INFORMATION: /note= "Residue can be either Tyr
            or Ser"

(ix) FEATURE:
        (A) NAME/KEY: Modified-site

```
        (B) LOCATION: 10
        (D) OTHER INFORMATION: /note= "Residue can be either Ser
            or Phe"

(ix) FEATURE:
        (A) NAME/KEY: Modified-site
        (B) LOCATION: 12
        (D) OTHER INFORMATION: /note= "Residue can be either Leu
            or Ile"

(ix) FEATURE:
        (A) NAME/KEY: Modified-site
        (B) LOCATION: 13
        (D) OTHER INFORMATION: /note= "Residue can be Pro, Ser or
            Leu"

(ix) FEATURE:
        (A) NAME/KEY: Modified-site
        (B) LOCATION: 17
        (D) OTHER INFORMATION: /note= "Residue can be either Leu
            or Arg"

(ix) FEATURE:
        (A) NAME/KEY: Modified-site
        (B) LOCATION: 19
        (D) OTHER INFORMATION: /note= "Residue can be Glu, Asp or
            Gly"

(ix) FEATURE:
        (A) NAME/KEY: Modified-site
        (B) LOCATION: 20
        (D) OTHER INFORMATION: /note= "Residue can be either Ile
            or Phe"

(ix) FEATURE:
        (A) NAME/KEY: Modified-site
        (B) LOCATION: 21
        (D) OTHER INFORMATION: /note= "Residue can be either Ala
            or Val"

(ix) FEATURE:
        (A) NAME/KEY: Modified-site
        (B) LOCATION: 23
        (D) OTHER INFORMATION: /note= "Residue can be either Leu
            or Pro"

(ix) FEATURE:
        (A) NAME/KEY: Modified-site
        (B) LOCATION: 26
        (D) OTHER INFORMATION: /note= "Residue can be either Met
            or Thr"

(ix) FEATURE:
        (A) NAME/KEY: Modified-site
        (B) LOCATION: 27
        (D) OTHER INFORMATION: /note= "Residue can be either Ser
            or Leu"

(ix) FEATURE:
        (A) NAME/KEY: Modified-site
        (B) LOCATION: 28
        (D) OTHER INFORMATION: /note= "Residue can be either Val
            or Phe"

(ix) FEATURE:
        (A) NAME/KEY: Modified-site
        (B) LOCATION: 29
        (D) OTHER INFORMATION: /note= "Residue can be either Thr
            or Ile"

(ix) FEATURE:
        (A) NAME/KEY: Modified-site
        (B) LOCATION: 30
        (D) OTHER INFORMATION: /note= "Residue can be either Cys
            or Tyr"

(xi) SEQUENCE DESCRIPTION: SEQ ID NO:36:

Arg Cys Leu Ser Ile Xaa Arg Phe Xaa Xaa Ser Xaa Xaa Thr Phe Ile
```

```
 1               5              10              15
Xaa Ile Xaa Xaa Xaa Met Xaa Phe Phe Xaa Xaa Xaa Xaa Xaa Phe Leu
            20                  25                  30
```

(2) INFORMATION FOR SEQ ID NO:37:

(i) SEQUENCE CHARACTERISTICS:
        (A) LENGTH: 1820 base pairs
        (B) TYPE: nucleic acid
        (C) STRANDEDNESS: single
        (D) TOPOLOGY: linear
    (xi) SEQUENCE DESCRIPTION: SEQ ID NO:37:

```
CGGCACGAGT AGCCCCCACC ATCTTTTGCA TTCATTTCAA GTTTCTCCAA ATCTCGATGG      60

GACCTCCAAT TTTGGCTCCA CCACAAACAA GTCTGACATA TTGAGCAAAA CATATTGATT     120

TAATTTAAAG AACAGACATC TGGCCATTCA TGCTAAGAGG TCTCTTCATT GTTGAGTGGG     180

AACAGCCTTG TATACGGGCT TACAAACACA TGGAAAAACA CCTTGTAGAA GAGATCATGC     240

TTCACTCAGT GCTAGATGTT GATGCCAGTG ATTTGCTTGG GGTAGTAAGC CAGTACTAGA     300

ATACAGGATG CACTTGGACT GGCAAACAGA ATACACCTGT TGCCTGAATA GAAACTCACA     360

GAGACCCGAT GCTGTCTGGT ACCAACAAGG TTCTGCTTCT GGGAAGAATT TACAGATATT     420

ATGTTGGGAA AAGAGACACC CTGTATGTGT AGAAACAAAG AAGCACAGAT CTTAGATGAA     480

TTAATATAAG AATGATACTT CTCTAGAAAC AAATGTAGTT ACCAACTATA TTCCAGAACC     540

CAATGCGGAT TCAGAATCTG TACATGTTGA ATCCAGGAA CATGATAACA TCAATCCACA      600

AGACGCTTGC GATAGTGAGC CGCTCGAACA AATGGATTCT GATACCAGGG TGTTGCCCGA     660

AAGTTTGGAT GAGGGGGTAC CACACCAATT CTCTAGATTA GGGCACCACT CAGACATGGC     720

ATCTGATATA AATGATGAAG AACCATCATT TAAAATCGGC GAGAATGACA TAATTCAACC     780

ACCCTGGGAA GATACAGCTC CATACCATTC AATAGATGAT GAAGAGCTTG ACAACTTAAT     840

GAGACTAACG GCGCAAGAAA CAAGTGACGA TCATGAAGAA GGGAATGGCA AACTCAATAC     900

GAATAAAAGT GAGAAGACTG AAAGAAAATC GCATGATACT CAGACACCGC AAGAAATATA     960

TGAAGAGCTT GACAACTTAC TGAGACTAAC GGCACAAGAA ATATATGAAG AGCGTAAAGA    1020

AGGGCATGGC AAACCCAATA CGAATAAAAG TGAGAAGGCT GAAAGAAAAT CGCATGATAC    1080

TCAGACAACG CAAGAAATAT GTGAAGAGTG TGAAGAAGGG CATGACAAAA TCAATAAGAA    1140

TAAAAGTGGA AATGCTGGAA TAAAATCGTA TGATACTCAG ACAACGCAAG AAATATGTGA    1200

AGAGTGTGAA GAAGGGCATG ACAAAATCAA TAAGAATAAA AGTGGAAATG CTGGAATAAA    1260

ATCGTATGAT ACTCAGACAC CGCAGGAAAC AAGTGACGCT CATGAAGAAG GGCATGACAA    1320

AATCAATACG AATAAAAGTG AGAAGGCTGA AGAAAATCG CATGATACTC AGACAACGCA     1380

AGAAATATGT GAAGAGTGTG AAGAAGGGCA TGACAAAATC AATAAGAATA AAAGTGGAAA    1440

TGCTGGAATA AAATCGTATG ATACTCAGAC ACCGCAGGAA ACAAGTGACG CTCATGAAGA    1500

AGAGCATGGC AATCTCAATA GAATAAAAG TGGGAAGGCT GGAATAAAAT CGCATAATAC     1560

TCAGACACCG CTGAAAAAAA AAGACTTTTG TAAAGAAGGG TGTCATGGTT GCAATAATAA    1620

GCCCGAGGAT AATGAAAGAG ACCCGTCGTC GCCTGATGAT GATGGTGGCT GCGAATGCGG    1680

CATGACGAAT CACTTTGTCT TTGACTACAA GACAACACTC TTGTTAAAGA GCCTCAAGAC    1740

TGAAACATCC ACTCATTATT ACATTGCCAT GGCTGCAATT TTTACTATTT CATTATTCCC    1800

ATGCATGTTT AAGGCTTTCC                                               1820
```

(2) INFORMATION FOR SEQ ID NO:38:

(i) SEQUENCE CHARACTERISTICS:
    (A) LENGTH: 445 amino acids
    (B) TYPE: amino acid
    (C) STRANDEDNESS:
    (D) TOPOLOGY: linear (xi) SEQUENCE DESCRIPTION: SEQ ID NO:38:

```
Tyr Lys Asn Asp Thr Ser Leu Glu Thr Asn Val Val Thr Asn Tyr Ile
 1               5                  10                  15

Pro Glu Pro Asn Ala Asp Ser Glu Ser Val His Val Glu Ile Gln Glu
            20                  25                  30

His Asp Asn Ile Asn Pro Gln Asp Ala Cys Asp Ser Glu Pro Leu Glu
        35                  40                  45

Gln Met Asp Ser Asp Thr Arg Val Leu Pro Glu Ser Leu Asp Glu Gly
50                  55                  60

Val Pro His Gln Phe Ser Arg Leu Gly His His Ser Asp Met Ala Ser
65                  70                  75                  80

Asp Ile Asn Asp Glu Glu Pro Ser Phe Lys Ile Gly Glu Asn Asp Ile
                85                  90                  95

Ile Gln Pro Pro Trp Glu Asp Thr Ala Pro Tyr His Ser Ile Asp Asp
            100                 105                 110

Glu Glu Leu Asp Asn Leu Met Arg Leu Thr Ala Gln Glu Thr Ser Asp
        115                 120                 125

Asp His Glu Glu Gly Asn Gly Lys Leu Asn Thr Asn Lys Ser Glu Lys
130                 135                 140

Thr Glu Arg Lys Ser His Asp Thr Gln Thr Pro Gln Glu Ile Tyr Glu
145                 150                 155                 160

Glu Leu Asp Asn Leu Leu Arg Leu Thr Ala Gln Glu Ile Tyr Glu Glu
                165                 170                 175

Arg Lys Glu Gly His Gly Lys Pro Asn Thr Asn Lys Ser Glu Lys Ala
            180                 185                 190

Glu Arg Lys Ser His Asp Thr Gln Thr Gln Glu Ile Cys Glu Glu
        195                 200                 205

Cys Glu Glu Gly His Asp Lys Ile Asn Lys Asn Lys Ser Gly Asn Ala
        210                 215                 220

Gly Ile Lys Ser Tyr Asp Thr Gln Thr Gln Glu Ile Cys Glu Glu
225                 230                 235                 240

Cys Glu Glu Gly His Asp Lys Ile Asn Lys Asn Lys Ser Gly Asn Ala
                245                 250                 255

Gly Ile Lys Ser Tyr Asp Thr Gln Thr Pro Gln Glu Thr Ser Asp Ala
            260                 265                 270

His Glu Glu Gly His Asp Lys Ile Asn Thr Asn Lys Ser Glu Lys Ala
        275                 280                 285

Glu Arg Lys Ser His Asp Thr Gln Thr Gln Glu Ile Cys Glu Glu
        290                 295                 300

Cys Glu Glu Gly His Asp Lys Ile Asn Lys Asn Lys Ser Gly Asn Ala
305                 310                 315                 320

Gly Ile Lys Ser Tyr Asp Thr Gln Thr Pro Gln Glu Thr Ser Asp Ala
                325                 330                 335

His Glu Glu His Gly Asn Leu Asn Lys Asn Lys Ser Gly Lys Ala
            340                 345                 350

Gly Ile Lys Ser His Asn Thr Gln Thr Pro Leu Lys Lys Lys Asp Phe
        355                 360                 365

Cys Lys Glu Gly Cys His Gly Cys Asn Asn Lys Pro Glu Asp Asn Glu
```

```
            370             375             380
Arg Asp Pro Ser Ser Pro Asp Asp Gly Gly Cys Glu Cys Gly Met
385                 390                 395                 400

Thr Asn His Phe Val Phe Asp Tyr Lys Thr Thr Leu Leu Leu Lys Ser
                405                 410                 415

Leu Lys Thr Glu Thr Ser Thr His Tyr Tyr Ile Ala Met Ala Ala Ile
            420                 425                 430

Phe Thr Ile Ser Leu Phe Pro Cys Met Phe Lys Ala Phe
            435                 440                 445

(2) INFORMATION FOR SEQ ID NO:39:

(i) SEQUENCE CHARACTERISTICS:
        (A) LENGTH: 32 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 3
        (D) OTHER INFORMATION: /note= "Residue can be either Gly
            or Asp"

(ix) FEATURE:
        (A) NAME/KEY: Modified-site
        (B) LOCATION: 5
        (D) OTHER INFORMATION: /note= "Residue can be either Pro
            or Ile"

(ix) FEATURE:
        (A) NAME/KEY: Modified-site
        (B) LOCATION: 7
        (D) OTHER INFORMATION: /note= "Residue can be either Lys
            or Thr"

(ix) FEATURE:
        (A) NAME/KEY: Modified-site
        (B) LOCATION: 11
        (D) OTHER INFORMATION: /note= "Residue can be either Glu
            or Gly"

(ix) FEATURE:
        (A) NAME/KEY: Modified-site
        (B) LOCATION: 12
        (D) OTHER INFORMATION: /note= "Residue can be either Lys
            or Asn"

(ix) FEATURE:
        (A) NAME/KEY: Modified-site
        (B) LOCATION: 14
        (D) OTHER INFORMATION: /note= "Residue can be either Glu
            or Gly"

(ix) FEATURE:
        (A) NAME/KEY: Modified-site
        (B) LOCATION: 15
        (D) OTHER INFORMATION: /note= "Residue can be either Ile
            or Arg"

(ix) FEATURE:
        (A) NAME/KEY: Modified-site
        (B) LOCATION: 18
        (D) OTHER INFORMATION: /note= "Residue can be either His
            or Tyr"

(ix) FEATURE:
        (A) NAME/KEY: Modified-site
        (B) LOCATION: 23
        (D) OTHER INFORMATION: /note= "Residue can be either Thr
            or Pro"

(ix) FEATURE:
        (A) NAME/KEY: Modified-site
```

(B) LOCATION: 26
(D) OTHER INFORMATION: /note= "Residue can be either Ile or Thr"

(ix) FEATURE:
(A) NAME/KEY: Modified-site
(B) LOCATION: 27
(D) OTHER INFORMATION: /note= "Residue can be either Cys or Ser"

(ix) FEATURE:
(A) NAME/KEY: Modified-site
(B) LOCATION: 28
(D) OTHER INFORMATION: /note= "Residue can be either Asp or Glu"

(ix) FEATURE:
(A) NAME/KEY: Modified-site
(B) LOCATION: 29
(D) OTHER INFORMATION: /note= "Residue can be either Glu or Ala"

(ix) FEATURE:
(A) NAME/KEY: Modified-site
(B) LOCATION: 30
(D) OTHER INFORMATION: /note= "Residue can be either Cys or His"

(xi) SEQUENCE DESCRIPTION: SEQ ID NO:39:

```
Gly His Xaa Lys Xaa Asn Xaa Asn Lys Ser Xaa Xaa Ala Xaa Xaa Lys
1               5                   10                  15

Ser Xaa Asp Thr Gln Thr Xaa Gln Glu Xaa Xaa Xaa Xaa Xaa Glu Glu
            20                  25                  30
```

(2) INFORMATION FOR SEQ ID NO:40:

(i) SEQUENCE CHARACTERISTICS:
(A) LENGTH: 2430 base pairs
(B) TYPE: nucleic acid
(C) STRANDEDNESS: single
(D) TOPOLOGY: linear (xi) SEQUENCE DESCRIPTION: SEQ ID NO:40:

```
TGTATTGTGT AGATAAAAAT GATGTTTCAT TATGGAAATC AAAACCTATA ACAACTGTCA      60

GTACCACTAA TGATACTATT ACAAATACAC ACACTACTAA TGTAATTAAT GCCAATCTTA     120

TTGGCCACTT TAATTATAAG GATAGGGAAC CTTTAACAAT AGTATTTGTA TACATGATCG     180

ATGAATCAGA ACAAAATAAA TTATCACATC CGAATAAAAT TGATAAAATC AAAATTTCTG     240

ATTATATAAT TGAATTTGAT GACAATGCTA AATTACCAAC TGGTAGTGTT ATTGATTTAA     300

ACATCTATAC TTGCAAACAT AATAATCCAG TATTAATTGA ATTTTATGTT TCTATAGAAG     360

GATCTTTCTG CTATTATTTC TCTCATTGAA TAATGATACA AATGAATGGA ATAATCACAA     420

AATAAAATAT GATAAAAAAT ATAAAGAATA TACGGACATG AATGGTATTC ATTATTATTA     480

TATTGATGGT AGTTTACTTG TAAGTGGCGA AGTTACATCT AATTTTCGTT ATATTTCTAA     540

AGAATATGAA TATGAGCATA CAGGATTAGT AAAAAAATAT TGTAATGAAG AAAGATGTGT     600

AAAATTGGAT AACATTAAGA TAAAGGATAA TAATTTGGAA ATTTATGTGA AATAATTTAA     660

TGAAGTATAA TATTATTTAT AATAATTCAA AGATTAATAT AATCAATTAT TATAATTACA     720

AAAATAATTA ATTGTAGAAT ATTATATTAT TAATCAATTC AGATTATAAA TACATATTTT     780

TACATACATT TCAATTTAAA CATTCAAATT AATGTCATTT TTATCTACAT TATTATAATT     840

ATAACTATAA TATTCATTAA ATACTATTAA AAAAAATATC CTCTACATTA TATTAATTAT     900

TATAGTATGT CATTATATAA CATATTCACA ACGTATAACA AATCAATCAT TAACATATAC     960
```

```
ATATATGATA TCATTAATAA TCAATATTTA ATTGATACAA TAATCAATAG TCATCTGTAA    1020

TATAATCATT GTATACTAAT TTATTATAAA TTATTACAAA ATACACTCTT TTACTTCATT    1080

TTATTTCTGT TAAATTTCAT ATTCTAATAT TATATTCATC TTTCTCATGT TACTTTAATC    1140

TATTTCCATA TTTATCCCAA TTTCTTCATT TAAGACTGAG ATGTTCGTTC GTTCATACAT    1200

AAATAATGTG TAAATTTTGT AATATATAAT AATGTATACA TCTGGTATTA CATCTATTTT    1260

GTAATAAATA TTAAAAAAAC GGTTAAAGTT AGTGCCTTAA TTCCAGGAAT TATTACATTA    1320

GAAACTTTGG TGATTTTAGT GATTTCGGTG ATCATTGAAA GAAATGGTTT GAAACTTGCA    1380

ATACTGTCAT ACTCATCATA ATCCCCAATG TTGGAAATCA TGATGTCAAC AATTTTATTA    1440

AATTCTTCTG CTGCACTATT CAACTCCTTA ATCATGTCCT CAAAATGAGT GTTATAATCT    1500

CCATCCTTTT TAGTGATCTT ATCCCTCAAA ACTAAAGCTT TAGATTTGGA TTCGTCAAAA    1560

TTTTTCTTGA TATCATTAAC GGTATTGTCA TAATAGAATT TATAGATTAA ATGTTGTAAT    1620

AATAAGTCAC AATATATAAA CATATCTTTA AGTACAATAG ACTTCCATAT ATTACGGAAA    1680

TGGTCAAAAT TATCAGCAGC TGGACCTTCC AATGTACCAT AGGCCTTGTT TGATATTTCA    1740

TCAACCAATA ACTTATATTT TGAAGAGATA GTGGATGCAT TATCAAATAT TCTAGCCAAT    1800

TCTTCTTTCT TCATAAGGGA ATATTGTTCA GGAAAACATT TTTCCAATTC TTTTTTCAAT    1860

TTATTCTTCT CCTTGGTTTT TTCTTCAATG TAGTCTTTAT GACCATCGTT CACCCTATCT    1920

CGTTCCAATA TCATAACACT ATGTTTGTAT ATATAAGATA AACAAACTTC ATTAAATATA    1980

ACTATTCTTC TAGAATACGG AAGAAGCTGA TATCCAAATC GTTCACTAGA CCAACCAGCT    2040

TCACTAGGCC AACCAGTTCC ACTAGGCCAA CCAGTTCCAC TAGGCCCACC AGCTTCACTA    2100

GGCCCACCAG CTTCACTAGG CCCACCAGCT TCACTAGGCC CACCAGCTTC ACTAGGCCAA    2160

CCAGTTCCAC TAGGCCCACC AGCTTCACTA GGCCCACCAG CTTCACTGGG CCCAACAGTT    2220

CCACTAGGCC CACCAGCTTC ACTAGGCCCA CCAGCTTCGG GATCGGTATC ACTTGCAAAG    2280

ACAGCACCGC TCATTAAAAA GAGTGTAATA TAAGGAACTA ATATTGATTT AAATGACACC    2340

ATCTTTATAA ACCATAGTTA TTGGTACATT ATTAGTACAT TATTGGTATA TGATTGGTAC    2400

GTGGTAGTGA TTGTGGTGCT GCATCTAGTT                                    2430
```

(2) INFORMATION FOR SEQ ID NO:41:

(i) SEQUENCE CHARACTERISTICS:
        (A) LENGTH: 128 amino acids
        (B) TYPE: amino acid
        (C) STRANDEDNESS:
        (D) TOPOLOGY: linear (xi) SEQUENCE DESCRIPTION: SEQ ID NO:41:

```
Tyr Cys Val Asp Lys Asn Asp Val Ser Leu Trp Lys Ser Lys Pro Ile
1               5                   10                  15

Thr Thr Val Ser Thr Thr Asn Asp Thr Ile Thr Asn Thr His Thr Thr
                20                  25                  30

Asn Val Ile Asn Ala Asn Leu Ile Gly His Phe Asn Tyr Lys Asp Arg
            35                  40                  45

Glu Pro Leu Thr Ile Val Phe Val Tyr Met Ile Asp Glu Ser Glu Gln
        50                  55                  60

Asn Lys Leu Ser His Pro Asn Lys Ile Asp Lys Ile Lys Ile Ser Asp
65                  70                  75                  80

Tyr Ile Ile Glu Phe Asp Asp Asn Ala Lys Leu Pro Thr Gly Ser Val
                85                  90                  95
```

Ile Asp Leu Asn Ile Tyr Thr Cys Lys His Asn Asn Pro Val Leu Ile
            100                 105                 110

Glu Phe Tyr Val Ser Ile Glu Gly Ser Phe Cys Tyr Tyr Phe Ser His
            115                 120                 125

(2) INFORMATION FOR SEQ ID NO:42:

(i) SEQUENCE CHARACTERISTICS:
        (A) LENGTH: 1271 base pairs
        (B) TYPE: nucleic acid
        (C) STRANDEDNESS: single
        (D) TOPOLOGY: linear (xi) SEQUENCE DESCRIPTION: SEQ ID NO:42:

TGAGAAAACG CATATAATTG TAACTACGCC AGAGAAGTTT GACGTAGTTA CACGTAAAAC      60

AGGCAATGAG CCCCTGCTTG AGCGGCTTAG ATTGGTTATA ATTGATGAAA TACACCTACT     120

CCATGACACT AGGGGTCCAG TGCTGGAGGC TATTGTGGCC CGCCTGAGTC AGAGGCCCGA     180

ACGCGTAAGG CTAGTTGGTC TATCGGCCAC GCTTCCAAAC TACGAAGACG TGGCTAGATT     240

TCTCACTGTT AATCTAGACC GAGGGCTTTT CTACTTGGC AGCCACTTTA GGCCTGTGCC      300

CTTGGAGCAG GTGTATTATG GCGTGAAGGA GAAGAAGGCT ATCAAACGTT TCAACGCAAT     360

CAACGAAATT CTCTACCAAG AGGTGATTAA CGATGTTTCT AGCTGCCAAA TTCTTGTTTT     420

TGTGCATTCT AGAAAGGAAA CGTACAGGAC GGCAAAATTT ATCAAAGACA CGGCCCTTTC     480

ACGGACAAC TTGGGAGCCT AAACCCTAAA CCCTAAACCC TAAACCCTAA CCCTAAACCC      540

TAAACCCTAA ACCCTAAACC CTAAACCCTA ACCCTAACCC TAACCCTAAC CCTAACCTAG     600

CCTTCATTGA CGTCTATCCC CAATCTTAGA AAAATCTTCA AATCGATTCT AGAATAACTG     660

GAAGCAATTA TCAGAAATTG TATAACTGCT TATTAGCTTA TTAGCTTATT AGTTAGGATG     720

TATGCACATT GATGACAACT AGATGCAGCA CCACAATCAC TACCACGTAC CAATCATATA     780

CCAATAATGT ACTAATAATG TACCAATAAC TATGGTTTAT AAAGATGGTG TCATTTAAAT     840

CAATATTAGT TCCTTATATT ACACTCTTTT TAATGAGCGG TGCTGTCTTT GCAGGTGATA     900

CCGATCGCGA AGCTGGTGGG CCTAGTGGAA CTGTTGGGCC TAGTGAAGCT GGTGGGCCTA     960

GTGAAGCTGG TGGGCCTAGT GAAGCTGGTG GGCCTAGTGA AGCTGGTGGG CCTAGTGAAG    1020

CTGGTGGGCC TAGTGAAGCT GGTGGGCCTA GTGAAGCTGG TGGGCCTAGT GAAGCTGGTG    1080

GGCCTAGTGG AACTGGTTGG CCTAGTGAAG CTGGTGGGCC TAGTGAAGCT GGTGGGCCTA    1140

GTGAAGCTGG TGGGCCTAGT GGAACTGGTT GGCCTAGTGA AGCTGGTTGG CCTAGTGAAG    1200

CTGGTTGGCC TAGTGAAGCT GGTTGGCCTA GTGAAGCTGG TTGGCCTAGT GAAGCTGGTT    1260

GGCCTAGTGA A                                                        1271

(2) INFORMATION FOR SEQ ID NO:43:

(i) SEQUENCE CHARACTERISTICS:
        (A) LENGTH: 166 amino acids
        (B) TYPE: amino acid
        (C) STRANDEDNESS:
        (D) TOPOLOGY: linear (xi) SEQUENCE DESCRIPTION: SEQ ID NO:43:

Glu Lys Thr His Ile Ile Val Thr Thr Pro Glu Lys Phe Asp Val Val
1               5                   10                  15

Thr Arg Lys Thr Gly Asn Glu Pro Leu Leu Glu Arg Leu Arg Leu Val
            20                  25                  30

Ile Ile Asp Glu Ile His Leu Leu His Asp Thr Arg Gly Pro Val Leu

```
                35                  40                  45
Glu Ala Ile Val Ala Arg Leu Ser Gln Arg Pro Glu Arg Val Arg Leu
 50                  55                  60

Val Gly Leu Ser Ala Thr Leu Pro Asn Tyr Glu Asp Val Ala Arg Phe
 65                  70                  75                  80

Leu Thr Val Asn Leu Asp Arg Gly Leu Phe Tyr Phe Gly Ser His Phe
                     85                  90                  95

Arg Pro Val Pro Leu Glu Gln Val Tyr Tyr Gly Val Lys Glu Lys Lys
                    100                 105                 110

Ala Ile Lys Arg Phe Asn Ala Ile Asn Glu Ile Leu Tyr Gln Glu Val
                    115                 120                 125

Ile Asn Asp Val Ser Ser Cys Gln Ile Leu Val Phe Val His Ser Arg
                    130                 135                 140

Lys Glu Thr Tyr Arg Thr Ala Lys Phe Ile Lys Asp Thr Ala Leu Ser
145                 150                 155                 160

Arg Asp Asn Leu Gly Ala
                    165

(2) INFORMATION FOR SEQ ID NO:44:

(i) SEQUENCE CHARACTERISTICS:
        (A) LENGTH: 154 amino acids
        (B) TYPE: amino acid
        (C) STRANDEDNESS:
        (D) TOPOLOGY: linear (xi) SEQUENCE DESCRIPTION: SEQ ID NO:44:

Leu Trp Phe Ile Lys Met Val Ser Phe Lys Ser Ile Leu Val Pro Tyr
 1                   5                  10                  15

Ile Thr Leu Phe Leu Met Ser Gly Ala Val Phe Ala Gly Asp Thr Asp
                    20                  25                  30

Arg Glu Ala Gly Gly Pro Ser Gly Thr Val Gly Pro Ser Glu Ala Gly
                    35                  40                  45

Gly Pro Ser Glu Ala Gly Gly Pro Ser Glu Ala Gly Gly Pro Ser Glu
 50                  55                  60

Ala Gly Gly Pro Ser Glu Ala Gly Gly Pro Ser Glu Ala Gly Gly Pro
 65                  70                  75                  80

Ser Glu Ala Gly Gly Pro Ser Glu Ala Gly Gly Pro Ser Gly Thr Gly
                    85                  90                  95

Trp Pro Ser Glu Ala Gly Gly Pro Ser Glu Ala Gly Gly Pro Ser Glu
                   100                 105                 110

Ala Gly Gly Pro Ser Gly Thr Gly Trp Pro Ser Glu Ala Gly Trp Pro
                   115                 120                 125

Ser Glu Ala Gly Trp Pro Ser Glu Ala Gly Trp Pro Ser Glu Ala Gly
                   130                 135                 140

Trp Pro Ser Glu Ala Gly Trp Pro Ser Glu
145                 150

(2) INFORMATION FOR SEQ ID NO:45:

(i) SEQUENCE CHARACTERISTICS:
        (A) LENGTH: 4223 base pairs
        (B) TYPE: nucleic acid
        (C) STRANDEDNESS: single
        (D) TOPOLOGY: linear (xi) SEQUENCE DESCRIPTION: SEQ ID NO:45:

CTCGTGCCTT TCTCAACTGA TAACAGCTAA CAAAAAGTCT CTTATCTTAA ACCATCCTAT        60
```

```
ACCTCGTATT ATAATATGAA AAGGGCCTTT TCTAAATCTT TCCCCAAAGT TCTGCTATTT      120

AATTAAAAAA AAAAAAGACT CATTCAATAA ACGGGTGGGG CAGAAAGGGT ACCTTTCCAA      180

GTGTTCTTCC ATGACGACCC ACAATGCAAA GTTCTTCTTA CAAAGAAAAG AGAAAGATCC      240

ACTGAGTGAT AAGTAACCCA GCTGGGGCCG GGCGGTGGTG GCGCACACCT TTAATCCCAG      300

CACTCGGGAG GCAGAGGCAG GCGGATCTCT GTGAGTTCGA GACCAGGCTG GACCGACAGC      360

CTCCAAAACA ATACAGAGAA ACCCTGTCTC ATAAAAAACC AAAAAAAAAG TAACCCAGCT      420

GGATTTGGTA ACTGTCTCAG AAACAGACTA TATAAAACCT CATCACCCTA CAACAAGTAG      480

GAAGCTAGCG CTCCCCACCC CATCCCAACA CACACACACA CACACACACA CACACACACA      540

CACACACACA CACGCACACA CGCACGCACG CACACACGCA CGCACGCACA CACGCACACA      600

CGCACGCACA CACGCACACA CGCACGCACG CACGCACGCA CGCACGCACG CACGCCCTTC      660

TGTGTCTGTT CTGTTCAAGA AGGGTACCAC AAAAAAGTAC CTTATGGCCA CATCAATGAC      720

AATTATTACT GTATATAAAA TGCCCCCATG GATGGCATTG TATTGTCGAA ATTAAAGGCA      780

CCCCCGAAAG AACAGCACAG AGGGGCTACC ACCAATTAAC TCCCAGGAGG AAATAAAGAC      840

AGAAGTGTGA AGGAGGGAGA GAGGGAGGGA GGAAGGGAGG GAGAAAAGGA GGGAAAGGAA      900

CAAGGAGTAA CAGGGACAAA AGCAGCAGAT GGTGCCAGGC AGGAGTGTGC CTACCACACC      960

GGGCCTTCCC GTTACTTCAT TTACTCTCCT TTGCAGCCTG GAATAAACA AGTCACGCGT      1020

CACCCGGTGT CTCAAGCTCA GCATGGCTTG ATCTGAGTGC CCGTGTATGT GTTCATTCTA     1080

TAACTGATTT AAGGAACAAC TTTCTGCTCA TTGCCTCTAT CTTCTCAAAC ATTTCGAAGC     1140

AGTTATTTTT TATAAGAAAA TATAAAACAG GCCGACTAAA TTCGATCTTT CTCTCCCCAG     1200

CTGCTAGTTT CTTATCTAGC TGCTTTAGGC AGTCTCCACA GATTGCAGCC AGGCCCCTAT     1260

TCTCAATTCC ATCTGACTTC TGACAGCGCT CTCCATTTCT TATTTGCAGC TTAGACATCT     1320

TCACTGAGAG CAGGAGTAAT TCATTCAAAT GACAATGAGG TATCTGAATA TCACACAAAC     1380

ACTTCAAATT CTGTTTATTG GAAATAGATC TGCTCCTGCC CCATCATAAC AATCCTTTTT     1440

ATCTTACTTA ACAGGGCAA GAAAATCTTT CACTTCATTT CCTATCATCT CAAATGAGTT      1500

CCTGTACATG AATGACTTAA GGTAACCATA TCCAACAACT TGAAGCCAAC CAGTCCCTGG     1560

TCCTACTACA GACGTTAGGG AACATATGTG AAAACCTGGT GTACAACCTA AATCATAACT     1620

AGACAGAAGA CAGCACTATT TCCTGGTCAC ATAGAAAGCA GAATAGCATC CTCACACCAA     1680

TGAGGAAAAT GTCATGAAGG CAGGAGAGAT CATGACTGAG GTGATACTTT TACCAAAGAC     1740

TTGCCAGTGA TTAATTTCTC AATTAGTTAG CAAAAAATAT GGCTCTCTAG TGAATTTGTG     1800

TCCACACCAT TTTCCAGATG TTTTGATGTC ACTTAAATCA ATCTAATTAT TTAAGTTAAA     1860

AAATGTTACA GATCATTGCT TTTTTTCTTT TTTAGAAGAC ATCAAAACAA TAGGATTTCT     1920

ATGAAATATT CTCACTTCAC AGCTGTGTCA GTTAAAGTGC TTTGGGTTAT ACATAAAGAA     1980

AACAGACTCA AGAAAGTAAG AACAGGAATT TGGAGCTTGC AACACTGATG TTCTTTGTAA     2040

AAAGAGAGAC TTTATCCAGG GATTAGATTC TGTCACAAGG CCTGGAACTC TCTCTTCTCA    2100

GCCTTATTTC CCCAATATGG ATTAGAATCT TACACTGCAA GCTTCCCACA AGGGTGGACA    2160

GGTCCTCACC ATTTGTTTCA GCAGGAAAAA GAGTCTGTAT GCATCCGTGA TATCTAAGTC    2220

ACAATTCCAG AAGTGAGCTT TCCTGGCTCC TATTGGTCGG ACTTAGGTCA GGTGTCACAT    2280

TTCCTTTTGG ATTAGTCTGT GATTAATGAA TGGGCCCACT TTGCTCACCC ATTAAGACAA    2340

TAGGCTTCCA TTCTCGAAGC TGGAAGCATG ACATGTCCCA CAGAAACTGT AATAAGAGAG    2400
```

```
AACATAGGTT GCTGTGTGGA GAAACGAGGC AACCGGCAAG TCATAAGATG ACAAAGTCTT    2460

GGAAAGTCTA AGTCAGTGGT TCTCAGCCTT CCCTAAACCC TAAACCCTAA ACCCTAAACC    2520

CTAAACCCTA AACCCTAAAC CCCTAAACCC TAAACCCTAA ACCCTAAACC CTAAACCCTA    2580

ACCCTAAACC CTAAACCCTA AACCCTAAAC CCTAAACCCT AACCCTAACC CTAACCCTAA    2640

CCCTAACCTA GCCTTCATTG ACGTCTATCC CCAATCTTAG AAAAATCTTC AAATCGATTC    2700

TAGAATAACT GGAAGCAATT ATCAGAAATT GTATAACTGC TTATTAGCTT ATTAGCTTAT    2760

TAGTTAGGAT GTATGCACAT TGATGACAAC TAGATGCAGC ACCACAATCA CTACCACGTA    2820

CCAATCATAT ACCAATAATG TACTAATAAT GTACCAATAA CTATGGTTTA TAAAGATGGT    2880

GTCATTTAAA TCAATATTAG TTCCTTATAT TACACTCTTT TTAATGAGCG GTGCTGTCTT    2940

TGCAGGTGAT ACCGATCGCG AAGCTGGTGG GCCTAGTGGA ACTGTTGGGC CTAGTGAAGC    3000

TGGTGGGCCT AGTGAAGCTG GTGGGCCTAG TGAAGCTGGT GGGCCTAGTG AAGCTGGTGG    3060

GCCTAGTGAA GCTGGTGGGC CTAGTGAAGC TGGTGGGCCT AGTGAAGCTG GTGGGCCTAG    3120

TGGAACTGTT GGGCCTAGTG AAGCTGGTGG GCCTAGTGAA GCTGGTGGGC CTAGTGAAGC    3180

TGGTGGGCCT AGTGAAGCTG GTTGGCCTAG TGAAGCTGGT TGGCCTAGTG AAGCTGGTTG    3240

GCCTAGTGAA GCTGGTTGGC CTAGTGAAGC TGGTTGGCCT AGTGAAGCTG GTTGGCCTAG    3300

TGAACGATTT GGATATCAGC TTCTTTGGTA TTCTAGAAGA ATAGTTATAT TTAATGAAAT    3360

TTATTTATCT CATATATACG AACATAGTGT TATGATATTG GAACGAGATA GGGTGAACGA    3420

TGGTCATAAA GACTACATTG AAGAAAAAAC CAAGGAGAAG AATAAATTGA AAAAAGAATT    3480

GGAAAAATGT TTTCCTGAAC AATATTCCCT TATGAAGAAA GAAGAATTGG CTAGAATAAT    3540

TGATAATGCA TCCACTATCT CTTCAAAATA TAAGTTATTG GTTGATGAAA TATCCAACAA    3600

AGCCTATGGT ACATTGGAAG GTCCAGCTGC TGATGATTTT GACCATTTCC GTAATATATG    3660

GAAGTCTATT GTACCTAAAA ATATGTTTCT ATATTGTGAC TTATTATTAA ACATTTAAT    3720

CCGTTTAACC CCCAGAAAGA GCTGACCAGA CAAAGGTTAA CTCTTGAATC CCAGGCATCA    3780

GCCTGGGAAT CCATCATGGG ACTGATCAAG ACCCCCTGAA TGTGGGTGTC AGTGAGGAGG    3840

CCTAGGTAAT CTATTGAGCC TCGGGCAGCA GATCAGTACC CATCCCAATT ATACACAATT    3900

GCAGTGTTGT GGTTTCACAG TGAATAATTG TAGGTCACAG TCCATTATAT TGATGTCACA    3960

GTTTTTAATT GTCATGTCAC AGTGCAAGCT AGTGATGTCA GAGTGTATAA CTGTGTTCAT    4020

AGAGAATGTA TTGATGTCAC AGTCAATAAT CGTGATGTCA TAGTGCAGTA TATTGATGTC    4080

ACAATGTATA ATTGTGATGT TAAAGTGCAA GATAGTGAAG TCACAGTATA TAATTGTGAT    4140

GTCATATTGC ATTATAATGA TGTCACACTT TATAATTTTT TACATACAGC ACTATAGTGA    4200

TGTAACAGCC AATAATTGTG ATG                                         4223
```

(2) INFORMATION FOR SEQ ID NO:46:

(i) SEQUENCE CHARACTERISTICS:
        (A) LENGTH: 294 amino acids
        (B) TYPE: amino acid
        (C) STRANDEDNESS:
        (D) TOPOLOGY: linear (xi) SEQUENCE DESCRIPTION: SEQ ID NO:46:

```
Leu Trp Phe Ile Lys Met Val Ser Phe Lys Ser Ile Leu Val Pro Tyr
 1               5                  10                  15

Ile Thr Leu Phe Leu Met Ser Gly Ala Val Phe Ala Gly Asp Thr Asp
            20                  25                  30
```

-continued

```
Arg Glu Ala Gly Gly Pro Ser Gly Thr Val Gly Pro Ser Glu Ala Gly
        35                  40                  45

Gly Pro Ser Glu Ala Gly Gly Pro Ser Glu Ala Gly Gly Pro Ser Glu
 50                  55                  60

Ala Gly Gly Pro Ser Glu Ala Gly Gly Pro Ser Glu Ala Gly Gly Pro
 65                  70                  75                  80

Ser Glu Ala Gly Gly Pro Ser Gly Thr Val Gly Pro Ser Glu Ala Gly
                 85                  90                  95

Gly Pro Ser Glu Ala Gly Pro Ser Glu Ala Gly Gly Pro Ser Glu
            100                 105                 110

Ala Gly Trp Pro Ser Glu Ala Gly Trp Pro Ser Glu Ala Gly Trp Pro
            115                 120                 125

Ser Glu Ala Gly Trp Pro Ser Glu Ala Gly Trp Pro Ser Glu Ala Gly
            130                 135                 140

Trp Pro Ser Glu Arg Phe Gly Tyr Gln Leu Leu Trp Tyr Ser Arg Arg
145                 150                 155                 160

Ile Val Ile Phe Asn Glu Ile Tyr Leu Ser His Ile Tyr Glu His Ser
                165                 170                 175

Val Met Ile Leu Glu Arg Asp Arg Val Asn Asp Gly His Lys Asp Tyr
            180                 185                 190

Ile Glu Glu Lys Thr Lys Glu Lys Asn Lys Leu Lys Lys Glu Leu Glu
            195                 200                 205

Lys Cys Phe Pro Glu Gln Tyr Ser Leu Met Lys Lys Glu Leu Ala
210                 215                 220

Arg Ile Ile Asp Asn Ala Ser Thr Ile Ser Ser Lys Tyr Lys Leu Leu
225                 230                 235                 240

Val Asp Glu Ile Ser Asn Lys Ala Tyr Gly Thr Leu Glu Gly Pro Ala
                245                 250                 255

Ala Asp Asp Phe Asp His Phe Arg Asn Ile Trp Lys Ser Ile Val Pro
            260                 265                 270

Lys Asn Asn Phe Leu Tyr Cys Asp Leu Leu Lys His Leu Ile Arg
275                 280                 285

Leu Thr Pro Arg Lys Ser
290
```

(2) INFORMATION FOR SEQ ID NO:47:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:47:

```
Ser Glu Ala Gly Gly Pro Ser Glu Ala Gly Gly Pro Ser Gly Thr Gly
 1               5                  10                  15

Trp Thr Ser Gly Thr Gly Trp Pro Ser Glu Ala Gly Trp Ser
            20                  25                  30
```

(2) INFORMATION FOR SEQ ID NO:48:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:48:

```
Glu Ala Gly Gly Pro Ser Gly Thr Val Gly Pro Ser Gly Thr Gly Trp
1               5                   10                  15

Pro Ser Glu Ala Gly Trp Gly Ser Glu Ala Gly Trp Ser Ser
            20                  25                  30
```

(2) INFORMATION FOR SEQ ID NO:49:

(i) SEQUENCE CHARACTERISTICS:
        (A) LENGTH: 367 amino acids
        (B) TYPE: amino acid
        (C) STRANDEDNESS: single
        (D) TOPOLOGY: linear (xi) SEQUENCE DESCRIPTION: SEQ ID NO:49:

```
Met Val Ser Phe Lys Ser Ile Leu Val Pro Tyr Ile Thr Leu Phe Leu
1               5                   10                  15

Met Ser Gly Ala Val Phe Ala Ser Asp Thr Asp Pro Glu Ala Gly Gly
                20                  25                  30

Pro Ser Glu Ala Gly Gly Pro Ser Gly Thr Val Gly Pro Ser Glu Ala
                35                  40                  45

Gly Gly Pro Ser Glu Ala Gly Gly Pro Ser Gly Thr Gly Trp Pro Ser
        50                  55                  60

Glu Ala Gly Gly Pro Ser Glu Ala Gly Gly Pro Ser Glu Ala Gly Gly
65                  70                  75                  80

Pro Ser Glu Ala Gly Gly Pro Ser Gly Thr Gly Ser Glu Ala Gly Gly
                85                  90                  95

Trp Pro Ser Gly Thr Gly Trp Pro Ser Glu Ala Gly Trp Ser Ser Glu
                100                 105                 110

Arg Phe Gly Tyr Gln Leu Leu Pro Tyr Ser Arg Arg Ile Val Ile Phe
            115                 120                 125

Asn Glu Val Cys Leu Ser Tyr Ile Tyr Lys His Ser Val Met Ile Leu
130                 135                 140

Glu Arg Asp Arg Val Asn Asp Gly His Lys Asp Tyr Ile Glu Glu Lys
145                 150                 155                 160

Thr Lys Glu Lys Asn Lys Leu Lys Lys Glu Leu Glu Lys Cys Phe Pro
                165                 170                 175

Glu Gln Tyr Ser Leu Met Lys Lys Glu Glu Leu Ala Arg Ile Phe Asp
            180                 185                 190

Asn Ala Ser Thr Ile Ser Ser Lys Tyr Lys Leu Leu Val Asp Glu Ile
            195                 200                 205

Ser Asn Lys Ala Tyr Gly Thr Leu Glu Gly Pro Ala Ala Asp Asn Phe
    210                 215                 220

Asp His Phe Arg Asn Ile Trp Lys Ser Ile Val Leu Lys Asp Met Phe
225                 230                 235                 240

Ile Tyr Cys Asp Leu Leu Leu Gln His Leu Ile Tyr Lys Phe Tyr Tyr
                245                 250                 255

Asp Asn Thr Val Asn Asp Ile Lys Lys Asn Phe Asp Glu Ser Lys Ser
                260                 265                 270

Lys Ala Leu Val Leu Arg Asp Lys Ile Thr Lys Lys Asp Gly Asp Tyr
            275                 280                 285

Asn Thr His Phe Glu Asp Met Ile Lys Glu Leu Asn Ser Ala Ala Glu
            290                 295                 300

Glu Phe Asn Lys Ile Val Asp Ile Met Ile Ser Asn Ile Gly Asp Tyr
305                 310                 315                 320

Asp Glu Tyr Asp Ser Ile Ala Ser Phe Lys Pro Phe Leu Ser Met Ile
                325                 330                 335
```

```
             Thr Glu Ile Thr Lys Ile Thr Lys Val Ser Asn Val Ile Ile Pro Gly
                         340                 345                 350

Ile Lys Ala Leu Thr Leu Thr Val Phe Leu Ile Phe Ile Thr Lys
                     355                 360                 365

(2) INFORMATION FOR SEQ ID NO:50:

(i) SEQUENCE CHARACTERISTICS:
         (A) LENGTH: 1908 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Babesia Microti (xi) SEQUENCE DESCRIPTION: SEQ ID NO:50:

AAAAGATTTA ATGAACATAC TGACATGAAT GGTATTCATT ATTATTATAT TGATGGTAGT       60

TTACTTGCGA GTGGCGAAGT TACATCTAAT TTTCGTTATA TTTCTAAAGA ATATGAATAT     120

GAGCATACAG AATTAGCAAA AGAGCATTGC AAGAAAGAAA AATGTGTAAA TGTGGATAAC     180

ATTGAGGATA ATAATTTGAA ATATATATGCG AAACAGTTTA AATCTGTAGT TACTACTCCA    240

GCTGATGTAG CGGGTGTGTC AGATGGATTT TTTATACGTG GCCAAAATCT TGGTGCTGTG     300

GGCAGTGTAA ATGAACAACC TAATACTGTT GGTATGAGTT TAGAACAATT CATCAAGAAC     360

GAGCTTTATT CTTTTAGTAA TGAAATTTAT CATACAATAT CTAGTCAAAT CAGTAATTCT     420

TTCTTAATAA TGATGTCTGA TGCAATTGTT AAACATGATA ACTATATTTT AAAAAAAGAA     480

GGTGAAGGCT GTGAACAAAT CTACAATTAT GAGGAATTTA TAGAAAAGTT GAGGGGTGCT     540

AGAAGTGAGG GGAATAATAT GTTTCAGGAA GCTCTGATAA GGTTTAGGAA TGCTAGTAGT     600

GAAGAAATGG TTAATGCTGC AAGTTATCTA TCCGCCGCCC TTTTCAGATA TAAGGAATTT     660

GATGATGAAT TATTCAAAAA GGCCAACGAT AATTTTGGAC GCGATGATGG ATATGATTTT     720

GATTATATAA ATACAAAGAA AGAGTTAGTT ATACTTGCCA GTGTGTTGGA TGGTTTGGAT     780

TTAATAATGG AACGTTTGAT CGAAAATTTC AGTGATGTCA ATAATACAGA TGATATTAAG     840

AAGGCATTTG ACGAATGCAA ATCTAATGCT ATTATATTGA AGAAAAAGAT ACTTGACAAT     900

GATGAAGATT ATAAGATTAA TTTTAGGGAA ATGGTGAATG AAGTAACATG TGCAAACACA     960

AAATTTGAAG CCCTAAATGA TTTGATAATT TCCGACTGTG AGAAAAAAGG TATTAAGATA    1020

AACAGAGATG TGATTTCAAG CTACAAATTG CTTCTTTCCA CAATCACCTA TATTGTTGGA    1080

GCTGGAGTTG AAGCTGTAAC TGTTAGTGTG TCTGCTACAT CTAATGGAAC TGAATCTGGT    1140

GGAGCTGGTA GTGGAACTGG AACTAGTGTG TCTGCTACAT CTACTTTAAC TGGTAATGGT    1200

GGAACTGAAT CTGGTGGAAC AGCTGGAACT ACTACGTCTA GTGGAACTGA AGCTGGTGGA    1260

ACTAGTGGAA CTACTACGTC TAGTGGAGCT GCTAGTGGTA AAGCTGGAAC TGGAACAGCT    1320

GGAACTACTA CGTCTAGTGA AGGTGCTGGT AGTGATAAAG CTGGAACTGG AACTAGTGGA    1380

ACTACTACGT CTAGTGGAAC TGGTGCTGGT GGAGCTGGTA GTGGTGGACC TAGTGGACAT    1440

GCTTCTAATG CAAAAATTCC TGGAATAATG ACACTAACTC TATTTGCATT ATTAACATTT    1500

ATTGTAAATT GAATGAAACA CATGATTTAT ACATTATTAT ATATTACAAA ATTTACACAT    1560

TATTTATGTA TGAACGAACG AACATCTTGC TCTTAAATAA AGAAATTGAG ATATATATGG    1620

AAATAGATTA AAGTAACATG AGAAAGATGA ATATAATATT AGAATATGAA ATTTAACAGA    1680
```

```
AATAAAATGA AGTAAAAGAG TGTATTTTGT AATAATTTAT AATAAATTAG TATACAATGA      1740

TTATATTACA AATGGCTATT AAATATTTTA TTAATTAAAT ATTGATTAGT AATGATATTA      1800

TGTATGTACA TGTTAGGGTT GATTGTTATA CATTGTGAAT ATATTATATA ATTGTATATT      1860

ATATTGATTG ATATAATGTA GAGGATATTT TTTTAAATAG TATTTAAT                   1908
```

(2) INFORMATION FOR SEQ ID NO:51:

(i) SEQUENCE CHARACTERISTICS:
        (A) LENGTH: 1460 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Babesia Microti (xi) SEQUENCE DESCRIPTION: SEQ ID NO:51:

```
AATCCAACAT CTAGCCTAGT TAGTATATAT AGGTTAATAT CACATTATAG ATTATCTTTG        60

GATGATTGGT TATTATATAA CATGTCGCTG AATGACGATT ATTTTGCTAG ATAATATAAC       120

TACCGGTGAT TCTGAGGACC TACTTTAAAG AGAATAATTA ACATATCTAC CAGAATCAGT       180

TCCAATTTAT GTATTTTAAA GCTAATCACT ACTCGAAAAC TACGGTGAAA ATGGAAAAAC       240

AAGTGGAAGC TGTATGTCGT GGAAAGTCAC TACATTTTAT GTGGGCAAAT TTAATAATTC       300

TAAATACTAT GTTTTTGATG TTAAAAAGCG AAAAACACAC TTTAATGCAC ATTTTAACAT       360

CATCTGTATA ATATATATAT CAGCGTTGAA ATCATATGGC AAAGGTAATA AAGCGTTACA       420

TTTTGAGCGA ATAAAGGCAC ATATGCAAAC GTATGAAGCC TTGTATATTT GTGGAATTAT       480

ATTATGCTAG TAATTTGTGA TTAATAATGG CAATATTTAT ATACAAATAT TCGAGCGTTC       540

TATTATATGC ATGCACATAA TTAATCACAA ACTCTCATAT CATGGGGCGG TTTCGCCCAT       600

CATAAACATT ACTGTTAGCA CTCTGGTAGA TTAGCATGGT GAATCTCTCG ATACCTGGGC       660

TACTGTTGCT TTCCGCATAT TCCTTAAATT CTGCAAGTGC GGGGGATGTA TATGAGATAT       720

CTTCTGGTAA TCCACCCGAC ATAGAGCCAA CATCTACTTC TCTAGAAACA AATGTAGTTA       780

CCAACTATAT TCCAGAACCC AATGCGGATT CAGAATCTGT ACATGTTGAA ATCCAGGAAC       840

ATGATAACAT CAATCCACAA GACGCTTGCG ATAGTGAGCC GCTCGAACAA ATGGATTCTG       900

ATACCAGGGT GTTGCCCGAA AGTTTGGATG AGGGGGTACC ACACCAATTC TCTAGATTAG       960

GGCACCACTC AGACATGGCA TCTGATATAA ATGATGAAGA ACCATCATTT AAAATCGGCG      1020

AGAATGACAT AATTCAACCA CCCTGGGAAG ATACAGCTCC ATACCATTCA ATAGATGATG      1080

AAGAGCTTGA CAACTTAATG AGACTAACGG CGCAAGAAAC AAGTGACGAT CATGAAGAAG      1140

GGAATGGCAA ACTCAATACG AATAAAAGTG AGAAGACTGA AAGAAAATCG CATGATACTC      1200

AGACACCGCA AGAAATATAT GAAGAGCTTG ACAACTTACT GAGACTAACG GCACAAGAAA      1260

TATATGAAGA GCGTAAAGAA GGGCATGGCA ACCCAATAC GAATAAAAGT GAGAAGGCTG      1320

AAAGAAAATC GCATGATACT CAGACAACGC AAGAAATATG TGAAGAGTGT GAAGAAGGGC      1380

ATGACAAAAT CAATAAGAAT AAAAGTGGAA ATGCTGGAAT AAAATCGTAT GATACTCAGA      1440

CACCGCAGGA AACAAGTGAC                                                 1460
```

(2) INFORMATION FOR SEQ ID NO:52:

(i) SEQUENCE CHARACTERISTICS:
        (A) LENGTH: 503 amino acids

```
        (B) TYPE: amino acid
        (C) STRANDEDNESS: single
        (D) TOPOLOGY: linear (ii) MOLECULE TYPE: DNA (genomic)

(vi) ORIGINAL SOURCE:
        (A) ORGANISM: Babesia Microti (xi) SEQUENCE DESCRIPTION: SEQ ID NO:52:

Lys Arg Phe Asn Glu His Thr Asp Met Asn Gly Ile His Tyr Tyr Tyr
1               5                   10                  15

Ile Asp Gly Ser Leu Leu Ala Ser Gly Glu Val Thr Ser Asn Phe Arg
            20                  25                  30

Tyr Ile Ser Lys Glu Tyr Glu Tyr Glu His Thr Glu Leu Ala Lys Glu
        35                  40                  45

His Cys Lys Lys Glu Lys Cys Val Asn Val Asp Asn Ile Glu Asp Asn
    50                  55                  60

Asn Leu Lys Ile Tyr Ala Lys Gln Phe Lys Ser Val Val Thr Thr Pro
65                  70                  75                  80

Ala Asp Val Ala Gly Val Ser Asp Gly Phe Phe Ile Arg Gly Gln Asn
                85                  90                  95

Leu Gly Ala Val Gly Ser Val Asn Glu Gln Pro Asn Thr Val Gly Met
            100                 105                 110

Ser Leu Glu Gln Phe Ile Lys Asn Glu Leu Tyr Ser Phe Ser Asn Glu
        115                 120                 125

Ile Tyr His Thr Ile Ser Ser Gln Ile Ser Asn Ser Phe Leu Ile Met
    130                 135                 140

Met Ser Asp Ala Ile Val Lys His Asp Asn Tyr Ile Leu Lys Lys Glu
145                 150                 155                 160

Gly Glu Gly Cys Glu Gln Ile Tyr Asn Tyr Glu Glu Phe Ile Glu Lys
                165                 170                 175

Leu Arg Gly Ala Arg Ser Glu Gly Asn Asn Met Phe Gln Glu Ala Leu
            180                 185                 190

Ile Arg Phe Arg Asn Ala Ser Ser Glu Glu Met Val Asn Ala Ala Ser
        195                 200                 205

Tyr Leu Ser Ala Ala Leu Phe Arg Tyr Lys Glu Phe Asp Asp Glu Leu
    210                 215                 220

Phe Lys Lys Ala Asn Asp Asn Phe Gly Arg Asp Asp Gly Tyr Asp Phe
225                 230                 235                 240

Asp Tyr Ile Asn Thr Lys Lys Glu Leu Val Ile Leu Ala Ser Val Leu
                245                 250                 255

Asp Gly Leu Asp Leu Ile Met Glu Arg Leu Ile Glu Asn Phe Ser Asp
            260                 265                 270

Val Asn Asn Thr Asp Asp Ile Lys Lys Ala Phe Asp Glu Cys Lys Ser
        275                 280                 285

Asn Ala Ile Ile Leu Lys Lys Ile Leu Asp Asn Asp Glu Asp Tyr
    290                 295                 300

Lys Ile Asn Phe Arg Glu Met Val Asn Glu Val Thr Cys Ala Asn Thr
305                 310                 315                 320

Lys Phe Glu Ala Leu Asn Asp Leu Ile Ile Ser Asp Cys Glu Lys Lys
                325                 330                 335

Gly Ile Lys Ile Asn Arg Asp Val Ile Ser Ser Tyr Lys Leu Leu Leu
            340                 345                 350

Ser Thr Ile Thr Tyr Ile Val Gly Ala Gly Val Glu Ala Val Thr Val
        355                 360                 365
```

```
Ser Val Ser Ala Thr Ser Asn Gly Thr Glu Ser Gly Gly Ala Gly Ser
    370                 375                 380
Gly Thr Gly Thr Ser Val Ser Ala Thr Ser Thr Leu Thr Gly Asn Gly
385                 390                 395                 400
Gly Thr Glu Ser Gly Gly Thr Ala Gly Thr Thr Thr Ser Ser Gly Thr
                405                 410                 415
Glu Ala Gly Gly Thr Ser Gly Thr Thr Thr Ser Ser Gly Ala Ala Ser
                420                 425                 430
Gly Lys Ala Gly Thr Gly Thr Ala Gly Thr Thr Ser Ser Glu Gly
            435                 440                 445
Ala Gly Ser Asp Lys Ala Gly Thr Gly Thr Ser Gly Thr Thr Thr Ser
    450                 455                 460
Ser Gly Thr Gly Ala Gly Gly Ala Gly Ser Gly Gly Pro Ser Gly His
465                 470                 475                 480
Ala Ser Asn Ala Lys Ile Pro Gly Ile Met Thr Leu Thr Leu Phe Ala
                485                 490                 495
Leu Leu Thr Phe Ile Val Asn
            500
```

(2) INFORMATION FOR SEQ ID NO:53:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: DNA (genomic)

(vi) ORIGINAL SOURCE:
        (A) ORGANISM: Babesia Microti (xi) SEQUENCE DESCRIPTION: SEQ ID NO:53:

```
Met Val Asn Leu Ser Ile Pro Gly Leu Leu Leu Ser Ala Tyr Ser
1               5                   10                  15
Leu Asn Ser Ala Ser Ala Gly Asp Val Tyr Glu Ile Ser Ser Gly Asn
                20                  25                  30
Pro Pro Asp Ile Glu Pro Thr Ser Thr Ser Leu Glu Thr Asn Val Val
            35                  40                  45
Thr Asn Tyr Ile Pro Glu Pro Asn Ala Asp Ser Glu Ser Val His Val
    50                  55                  60
Glu Ile Gln Glu His Asp Asn Ile Asn Pro Gln Asp Ala Cys Asp Ser
65                  70                  75                  80
Glu Pro Leu Glu Gln Met Asp Ser Asp Thr Arg Val Leu Pro Glu Ser
                85                  90                  95
Leu Asp Glu Gly Val Pro His Gln Phe Ser Arg Leu Gly His His Ser
            100                 105                 110
Asp Met Ala Ser Asp Ile Asn Asp Glu Glu Pro Ser Phe Lys Ile Gly
        115                 120                 125
Glu Asn Asp Ile Ile Gln Pro Arg Trp Glu Asp Thr Ala Pro Tyr His
    130                 135                 140
Ser Ile Asp Asp Glu Glu Leu Asp Asn Leu Met Arg Leu Thr Ala Gln
145                 150                 155                 160
Glu Thr Ser Asp Asp His Glu Glu Gly Asn Gly Lys Leu Asn Thr Asn
                165                 170                 175
Lys Ser Glu Lys Thr Glu Arg Lys Ser His Asp Thr Gln Thr Pro Gln
            180                 185                 190
```

-continued

```
Glu Ile Tyr Glu Glu Leu Asp Asn Leu Leu Arg Leu Thr Ala Gln Glu
    195                 200                 205

Ile Tyr Glu Glu Arg Lys Glu Gly His Gly Lys Pro Asn Thr Asn Lys
    210                 215                 220

Ser Glu Lys Ala Glu Arg Lys Ser His Asp Thr Gln Thr Thr Gln Glu
225                 230                 235                 240

Ile Cys Glu Glu Cys Glu Gly Gly His Asp Lys Ile Asn Lys Asn Lys
                245                 250                 255

Ser Gly Asn Ala Gly Ile Lys Ser Tyr Asp Thr Gln Thr Pro Gln Glu
                260                 265                 270

Thr Ser Asp
        275
```

COMPOUNDS AND METHODS FOR THE DIAGNOSIS AND TREATMENT OF B. MICROTI INFECTION

CROSS-REFERENCE TO RELATED APPLICATIONS

This application is a continuation-in-part of U.S. application Ser. No. 08/723,142 filed Oct. 1, 1996.

TECHNICAL FIELD

The present invention relates generally to the detection of Babesia microti infection. In particular, the invention is related to polypeptides comprising a B. microti antigen, to antigenic epitopes of such an antigen and the use of such polypeptides and antigenic epitopes for the serodiagnosis and treatment of B. microti infection.

BACKGROUND OF THE INVENTION

Babesiosis is a malaria-like illness caused by the rodent parasite Babesia microti (B. microti) which is generally transmitted to humans by the same tick that is responsible for the transmission of Lyme disease and ehrlichiosis, thereby leading to the possibility of co-infection with babesiosis, Lyme disease and ehrlichiosis from a single tick bite. While the number of reported cases of B. microti infection in the United States is increasing rapidly, infection with B. microti, including co-infection with Lyme disease, often remains undetected for extended periods of time. Babesiosis is potentially fatal, particularly in the elderly and in patients with suppressed immune systems. Patients infected with both Lyme disease and babesiosis have more severe symptoms and prolonged illness compared to those with either infection alone.

The preferred treatments for Lyme disease, ehrlichiosis and babesiosis are different, with penicillins, such as doxycycline and amoxicillin, being most effective in treating Lyme disease, tetracycline being preferred for the treatment of ehrlichiosis, and anti-malarial drugs, such as quinine and clindamycin, being most effective in the treatment of babesiosis. Accurate and early diagnosis of B. microti infection is thus critical but methods currently employed for diagnosis are problematic.

All three tick-borne illnesses share the same flu-like symptoms of muscle aches, fever, headaches and fatigue, thus making clinical diagnosis difficult. Microscopic analysis of blood samples may provide false-negative results when patients are first seen in the clinic. Indirect fluorescent antibody staining methods for total immunoglobulins to B. microti may be used to diagnose babesiosis infection, but such methods are time-consuming and expensive. There thus remains a need in the art for improved methods for the detection of B. microti infection.

SUMMARY OF THE INVENTION

The present invention provides compositions and methods for the diagnosis and treatment of B. microti infection. In one aspect, polypeptides are provided comprising an immunogenic portion of a B. microti antigen, or a variant of such an antigen that differs only in conservative substitutions and/or modifications. In one embodiment, the antigen comprises an amino acid sequence encoded by a DNA sequence selected from the group consisting of (a) sequences recited in SEQ ID NO: 1–17, 37, 40, 42, 45, 50 and 51; (b) the complements of said sequences; and (c) sequences that hybridize to a sequence of (a) or (b) under moderately stringent conditions.

In another aspect, the present invention provides an antigenic epitope of a B. microti antigen comprising the amino acid sequence -$X_1$-$X_2$-$X_3$-$X_4$-$X_5$-Ser- (SEQ ID NO: 35), wherein $X_1$ is Glu or Gly, $X_2$ is Ala or Thr, $X_3$ is Gly or Val, $X_4$ is Trp or Gly and $X_5$ is Pro or Ser. In one embodiment of this aspect, $X_1$ is Glu, $X_2$ is Ala and $X_3$ is Gly. In a second embodiment $X_1$ is Gly, $X_2$ is Thr and $X_5$ is Pro. The present invention further provides polypeptides comprising at least two of the above antigenic epitopes, the epitopes being contiguous.

In yet another aspect, the present invention provides an antigenic epitope of a B. microti antigen comprising an amino acid sequence selected from the group consisting of SEQ ID NO: 36 and 39, together with polypeptides comprising at least two such antigenic epitopes, the epitopes being contiguous.

In a related aspect, DNA sequences encoding the above polypeptides, recombinant expression vectors comprising these DNA sequence and host cells transformed or transfected with such expression vectors are also provided.

In another aspect, the present invention provides fusion proteins comprising either a first and a second inventive polypeptide, a first and a second inventive antigenic epitope, or, alternatively, an inventive polypeptide and an inventive antigenic epitope.

In further aspects of the subject invention, methods and diagnostic kits are provided for detecting B. microti infection in a patient. In one embodiment, the method comprises: (a) contacting a biological sample with at least one polypeptide comprising an immunogenic portion of a B. microti antigen; and (b) detecting in the sample the presence of antibodies that bind to the polypeptide, thereby detecting B. microti infection in the biological sample. In other embodiments, the methods comprise: (a) contacting a biological sample with at least one of the above polypeptides or antigenic epitopes; and (b) detecting in the sample the presence of antibodies that bind to the polypeptide or antigenic epitope. Suitable biological samples include whole blood, sputum, serum, plasma, saliva, cerebrospinal fluid and urine. The diagnostic kits comprise one or more of the above polypeptides or antigenic epitopes in combination with a detection reagent.

The present invention also provides methods for detecting B. microti infection comprising: (a) obtaining a biological sample from a patient; (b) contacting the sample with at least two oligonucleotide primers in a polymerase chain reaction, at least one of the oligonucleotide primers being specific for a DNA sequence encoding the above polypeptides; and (c) detecting in the sample a DNA sequence that amplifies in the presence of the first and second oligonucleotide primers. In one embodiment, the oligonucleotide primer comprises at least about 10 contiguous nucleotides of a DNA sequence encoding the above polypeptides.

In a further aspect, the present invention provides a method for detecting B. microti infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment of this aspect, the oligonucleotide probe comprises at least about 15 contiguous nucleotides of a DNA sequence encoding the above polypeptides.

In yet another aspect, the present invention provides antibodies, both polyclonal and monoclonal, that bind to the polypeptides described above, as well as methods for their use in the detection of B. microti infection.

Within other aspects, the present invention provides pharmaceutical compositions that comprise one or more of the above polypeptides or antigenic epitopes, or a DNA molecule encoding such polypeptides, and a physiologically acceptable carrier. The invention also provides vaccines comprising one or more of the inventive polypeptides or antigenic epitopes and a non-specific immune response enhancer, together with vaccines comprising one or more DNA sequences encoding such polypeptides and a non-specific immune response enhancer.

In yet another aspect, methods are provided for inducing protective immunity in a patient, comprising administering to a patient an effective amount of one or more of the above pharmaceutical compositions or vaccines.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 shows the genomic sequence of the B. microti antigen BMNI-3 (SEQ ID NO: 3) including a translation of the putative open reading frame (SEQ ID NO: 49). An internal six amino acid repeat sequence (SEQ ID NO: 35) is indicated by vertical lines within the open reading frame.

FIG. 3 shows the reactivity of the B. microti antigens MN-10 and BMNI-20 with sera from B. microti-infected patients and from normal donors as determined by ELISA.

DETAILED DESCRIPTION OF THE INVENTION

Figure 2A:
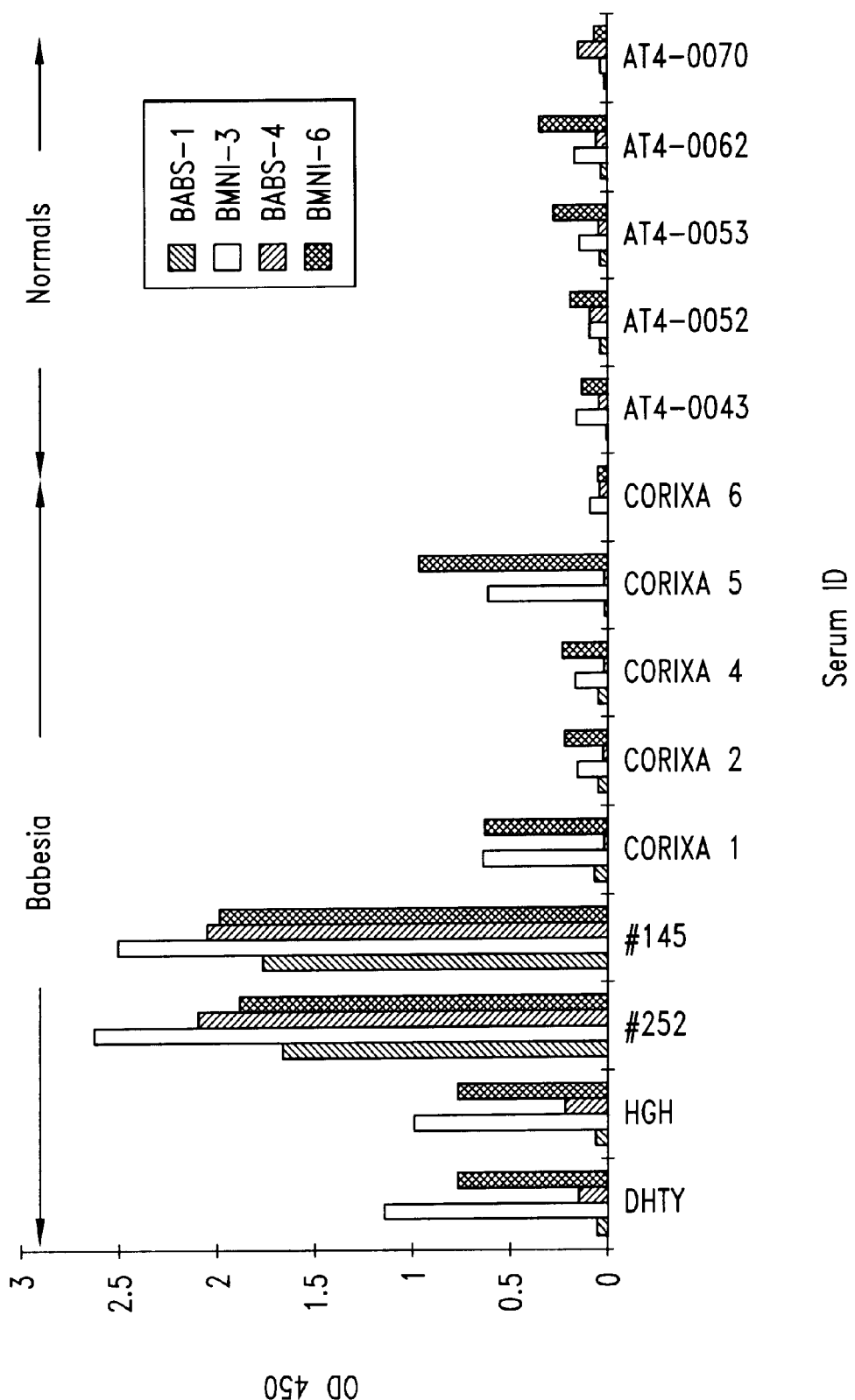
FIG. 2a shows the reactivity of the B. microti antigens BMNI-3 and BMNI-6, and the peptides BABS-1 and BABS-4 with sera from B. microti-infected individuals and from normal donors as determined by ELISA.

As noted above, the present invention is generally directed to compositions and methods for the diagnosis and treatment of B. microti infection. In one aspect, the compositions of the subject invention include polypeptides that comprise at least one immunogenic portion of a B. microti antigen, or a variant of such an antigen that differs only in conservative substitutions and/or modifications.

As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native B. microti antigen or may be heterologous, and such sequences may (but need not) be immunogenic.

An "immunogenic portion" of an antigen is a portion that is capable of reacting with sera obtained from a B. microti-infected individual (i.e., generates an absorbance reading with sera from infected individuals that is at least three standard deviations above the absorbance obtained with sera from uninfected individuals, in a representative ELISA assay described herein). Polypeptides comprising at least an immunogenic portion of one or more B. microti antigens as described herein may generally be used, alone or in combination, to detect B. microti in a patient.

The compositions and methods of this invention also encompass variants of the above polypeptides. A "variant," as used herein, is a polypeptide that differs from the native antigen only in conservative substitutions and/or modifications, such that the antigenic properties of the polypeptide are retained. Such variants may generally be identified by modifying one of the above polypeptide sequences, and evaluating the antigenic properties of the modified polypeptide using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In specific embodiments, the subject invention discloses polypeptides comprising at least an immunogenic portion of a B. microti antigen (or a variant of such an antigen), that comprises one or more of the amino acid sequences encoded by (a) a DNA sequence selected from the group consisting of SEQ ID NO: 1–17, 37, 40, 42, 45 50 and 51, (b) the complements of such DNA sequences or (c) DNA sequences substantially homologous to a sequence in (a) or (b).

The B. microti antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5× SSC, 0.5% SDS, 1.0 mM EDTA (pH 8.0); hybridizing at 50° C.–65° C., 5× SSC, overnight or, in the event of cross-species homology, at 45° C. with 0.5× SSC; followed by washing twice at 65° C. for 20 minutes with each of 2×, 0.5× and 0.2× SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

In general, B. microti antigens, and DNA sequences encoding such antigens, may be prepared using any of a variety of procedures. For example, DNA molecules encoding *B. microti* antigens may be isolated from a *B. microti* genomic or cDNA expression library by screening with sera from *B. microti*-infected individuals as described below in Example 1, and sequenced using techniques well known to those of skill in the art. DNA molecules encoding *B. microti* antigens may also be isolated by screening an appropriate *B. microti* expression library with anti-sera (e.g., rabbit) raised specifically against *B. microti* antigens.

Antigens may be induced from such clones and evaluated for a desired property, such as the ability to react with sera obtained from a *B. microti*-infected individual as described herein. Alternatively, antigens may be produced recombinantly, as described below, by inserting a DNA sequence that encodes the antigen into an expression vector and expressing the antigen in an appropriate host. Antigens may be partially sequenced using, for example, traditional Edman chemistry. See Edman and Berg, *Eur. J. Biochem.* 80:116–132,1967.

DNA sequences encoding antigens may also be obtained by screening an appropriate *B. microti* cDNA or genomic DNA library for DNA sequences that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning: A Laboratory Manual,* Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc., Foster City, Calif., and may be operated according to the manufacturer's instructions.

Immunogenic portions of *B. microti* antigens may be prepared and identified using well known techniques, such as those summarized in Paul, *Fundamental Immunology,* 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of a *B. microti* antigen generates at least about 20%, and preferably about 100%, of the signal induced by the full length antigen in a model ELISA as described herein.

Portions and other variants of *B. microti* antigens may be generated by synthetic or recombinant means. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli,* yeast or a mammalian cell line, such as COS or CHO. The DNA sequences expressed in this manner may encode naturally occurring antigens, portions of naturally occurring antigens, or other variants thereof.

In another aspect, the present invention provides epitope repeat sequences, or antigenic epitopes, of a *B. microti* antigen, together with polypeptides comprising at least two such contiguous antigenic epitopes. As used herein an "epitope" is a portion of an antigen that reacts with sera from *B. microti*-infected individuals (i.e. an epitope is specifically bound by one or more antibodies present in such sera). As discussed above, epitopes of the antigens described in the present application may be generally identified using techniques well known to those of skill in the art.

In one embodiment, antigenic epitopes of the present invention comprise the amino acid sequence -$X_1$-$X_2$-$X_3$-$X_4$-$X_5$-Ser- (SEQ ID NO: 35), wherein $X_1$ is Glu or Gly, $X_2$ is Ala or Thr, $X_3$ is Gly or Val, $X_4$ is Trp or Gly, and $X_5$ is Pro or Ser. In another embodiment, the antigenic epitopes of the present invention comprise an amino acid sequence selected from the group consisting of SEQ ID NO: 36 and 39. As discussed in more detail below, antigenic epitopes provided herein may be employed in the diagnosis and treatment of *B. microti* infection, either alone or in combination with other *B. microti* antigens or antigenic epitopes. Antigenic epitopes and polypeptides comprising such epitopes may be prepared by synthetic means, as described generally above and in detail in Example 2.

In general, regardless of the method of preparation, the polypeptides and antigenic epitopes disclosed herein are prepared in substantially pure form. Preferably, the polypeptides and antigenic epitopes are at least about 80% pure, more preferably at least about 90% pure and most preferably at least about 99% pure.

In a further aspect, the present invention provides fusion proteins comprising either a first and a second inventive polypeptide, a first and a second inventive antigenic epitope or an inventive polypeptide and an antigenic epitope of the present invention, together with variants of such fusion proteins. The fusion proteins of the present invention may also include a linker peptide between the polypeptides or antigenic epitopes.

A DNA sequence encoding a fusion protein of the present invention is constructed using known recombinant DNA techniques to assemble separate DNA sequences encoding, for example, the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric hindrance.

In another aspect, the present invention provides methods for using polypeptides comprising an immunogenic portion of a *B. microti* antigen and the antigenic epitopes described above to diagnose babesiosis. In this aspect, methods are provided for detecting *B. microti* infection in a biological sample, using one or more of the above polypeptides and antigenic epitopes, alone or in combination. For clarity, the term "polypeptide" will be used when describing specific embodiments of the inventive diagnostic methods. However, it will be clear to one of skill in the art that the antigenic epitopes of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to *B. microti* antigens which may be indicative of babesiosis.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *B. microti*. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratory Manual,* Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within a *B. microti*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*B. microti* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for babesiosis. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for babesiosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*B. microti* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 $\mu$g, and more preferably from about 50 ng to about 500 ng. Such tests can typically be performed with a very small amount (e.g., one drop) of patient serum or blood.

Of course, numerous other assay protocols exist that are suitable for use with the polypeptides and antigenic epitopes of the present invention. The above descriptions are intended to be exemplary only.

In yet another aspect, the present invention provides antibodies to the polypeptides and antigenic epitopes of the present invention. Antibodies may be prepared by any of a variety of techniques known to those of ordinary skill in the art. See, e.g., Harlow and Lane, *Antibodies: A Laboratory Manual,* Cold Spring Harbor Laboratory, Cold Spring Harbor, N.Y., 1988. In one such technique, an immunogen comprising the antigenic polypeptide or epitope is initially injected into any of a wide variety of mammals (e.g., mice, rats, rabbits, sheep and goats). The polypeptides and antigenic epitopes of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide or antigenic epitope may then be purified from such antisera by, for example, affinity chromatography using the polypeptide or antigenic epitope coupled to a suitable solid support.

Monoclonal antibodies specific for the antigenic polypeptide or epitope of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide or antigenic epitope of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide or antigenic epitope. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides or antigenic epitopes of this invention may be used in the purification process in, for example, an affinity chromatography step.

Antibodies may be used in diagnostic tests to detect the presence of *B. microti* antigens using assays similar to those detailed above and other techniques well known to those of skill in the art, thereby providing a method for detecting *B. microti* infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify *B. microti*-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. Ibid; Ehrlich, Ibid). Primers or probes may thus be used to detect *B. microti*-specific sequences in biological samples, preferably sputum, blood, serum, saliva, cerebrospinal fluid or urine. DNA probes or primers comprising oligonucleotide sequences described above may be used alone or in combination with each other.

In another aspect, the present invention provides methods for using one or more of the above polypeptides, antigenic epitopes or fusion proteins (or DNA molecules encoding such polypeptides) to induce protective immunity against *B. microti* infection in a patient. As used herein, a "patient" refers to any warm-blooded animal, preferably a human. A patient may be afflicted with a disease, or may be free of detectable disease and/or infection. In other words, protective immunity may be induced to prevent or treat babesiosis.

In this aspect, the polypeptide, antigenic epitope, fusion protein or DNA molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other *B. microti* antigens, either incorporated into a combination polypeptide or present within a separate polypeptide.

Alternatively, a vaccine may contain DNA encoding one or more polypeptides, antigenic epitopes or fusion proteins as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749, 1993 and reviewed by Cohen, Science 259:1691–1692, 1993. The uptake of naked DNA may be increased by coating the DNA onto biodegradable beads, which are efficiently transported into the cells.

In a related aspect, a DNA vaccine as described above may be administered simultaneously with or sequentially to either a polypeptide of the present invention or a known *B. microti* antigen. For example, administration of DNA encoding a polypeptide of the present invention, either "naked" or in a delivery system as described above, may be followed by administration of an antigen in order to enhance the protective immune effect of the vaccine.

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from *B. microti* infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

The following Examples are offered by way of illustration and not by way of limitation.

EXAMPLE 1

Isolation of DNA Sequences Encoding *B. Microti* Antigens

This example illustrates the preparation of DNA sequences encoding *B. microti* antigens by screening a *B. microti* expression library with sera obtained from patients infected with *B. microti*.

*B. microti* genomic DNA was isolated from infected hamsters and sheared by sonication. The resulting randomly sheared DNA was used to construct a *B. microti* genomic expression library (approximately 0.5–4.0 kbp inserts) with EcoRl adaptors and a Lambda ZAP Il/EcoRI/CIAP vector (Stratagene, La Jolla, Calif.). The unamplified library (1.2× $10^6$/ml) was screened with an *E. coli* lysate-absorbed *B. microti* patient serum pool, as described in Sambrook et al., *Molecular Cloning: A Laboratory Manual,* Cold Spring Harbor Laboratories, Cold Spring Harbor, N.Y., 1989. Positive plaques were visualized and purified with goat-anti-human alkaline phosphatase. Phagemid from the plaques was rescued and DNA sequence for positive clones was obtained using forward, reverse, and specific internal primers on a Perkin Elmer/Applied Biosystems Inc. Automated Sequencer Model 373A (Foster City, Calif.).

Seventeen antigens (hereinafter referred to as BMNI-1–BMNI-17) were purified and three were possibly redundant. The determined DNA sequences for BMNI-1–BMNI-17 are shown in SEQ ID NO: 1–17, respectively. The deduced amino acid sequences for BMNI-1–BMNI-6, BMNI-8 and BMNI-10–BMNI-17 are shown in SEQ ID NO: 18–32, respectively, with the predicted 5' and 3' protein sequences for BMNI-9 being shown in SEQ ID NO: 33 and 34, respectively.

The isolated DNA sequences were compared to known sequences in the gene bank using the DNA STAR system. Nine of the seventeen antigens (BMNI-1, BMNI-2, BMNI-3, BMNI-5, BMNI-6, BMNI-7, BMNI-12, BMNI-13 and BMNI-16) share some homology, with BMNI-1 and BMNI-16 being partial clones of BMNI-3. All of these nine antigens contain a degenerate repeat of six amino acids (SEQ ID NO: 35), with between nine to twenty-two repeats occurring in each antigen. The repeat portion of the sequences was found to bear some similarity to a *Plasmodium falciparum* merozoite surface antigen (MSA-2 gene). FIG. I shows the genomic sequence of BMNI-3 including a translation of the putative open reading frame, with the internal six amino acid repeat sequence being indicated by vertical lines within the open reading frame.

A second group of five antigens bear some homology to each other but do not show homology to any previously identified sequences (BMNI-4, BMNI-8, BMNI-9, BMNI-10 and BMNI-11). These antigens may belong to a family of genes or may represent parts of a repetitive sequence. BMNI-17 contains a novel degenerate repeat of 32 amino acids (SEQ ID NO: 36). Similarly, the reverse complement of BMNI-17 (SEQ ID NO: 37) contains an open reading frame that encodes an amino acid sequence (SEQ ID NO: 38) having a degenerate 32 amino acid repeat (SEQ ID NO: 39).

The reverse complement of BMNI-3 (SEQ ID NO: 40) has an open reading frame which shows homology with the BMNI-4-like genes. The predicted amino acid sequence encoded by this open reading frame is shown in SEQ ID NO: 41. The reverse complement of BMNI-5 (SEQ ID NO: 42) contains a partial copy of a BMNI-3-like sequence and also an open reading frame with some homology to two yeast genes (*S. cerevisiae* G9365 ORF gene, and *S. cerevisiae* accession no. U18922). The predicted 5' and 3' amino acid sequences encoded by this open reading frame are shown in SEQ ID NO: 43 and 44, respectively. The reverse complement of BMNI-7 (SEQ ID NO: 45) contains an open reading frame encoding the amino acid sequence shown in SEQ ID NO: 46.

A telomeric repeat sequence, which is conserved over a wide range of organisms, was found in five antigens (BMNI-2, BMNI-5, BMNI-6, BMNI-7 and BMNI-16), indicating that many of the isolated genes may have a telomere-proximal location in the genome. BMNI-10 appears to include a double insert, the 3'-most segment having some homology to *E. coli* aminopeptidase N. In addition, BMNI-7 contains apparently random insertions of hamster DNA. One such insertion has characteristics of a transposible element (i.e. poly A tail and flanked by a direct repeat).

In subsequent studies, two additional *B. microti* antigens were isolated by screening the *B. microti* genomic DNA expression library described above with a serum pool from *B. microti* infected patients that showed low reactivity with recombinant proteins generated from clones BMNI-2–BMNI-17. The determined DNA sequences for these two clones, hereinafter referred to as MN-10 and BMNI-20, are provided in SEQ ID NO: 50 and 51, respectively, with the corresponding predicted amino acid sequences being provided in SEQ ID NO: 52 and 53. MN-10 was found to extend the sequence of BMNI-4 in the 3' direction and BMNI-20 was found to extend the sequence of BMNI-17 in the 5' direction.

EXAMPLE 2

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

This procedure was used to synthesize two peptides (hereinafter referred to as BABS-1 and BABS-4) made to the repeat region of the isolated *B. microti* antigen BMNI-3. The sequences of BABS-1 and BABS-4 are shown in SEQ ID NO: 47 and 48, respectively.

EXAMPLE 3

Use of Representative Antigens and Peptides for Serodiagnosis of *B. Microti* Infection A. Diagnostic Properties of Representative Antigens and Peptides as Determined By ELISA The diagnostic properties of recombinant BMNI-3, BMNI-4, BMNI-6, BMNI-15, MN-10 and BMNI-20, and the BABS-1 and BABS-4 peptides were determined as follows.

Assays were performed in 96 well plates coated overnight at 4° C. with 200 ng antigen/well added in 50 μl of carbonate coating buffer. The plate contents were then removed and the wells were blocked for 2 hours with 200 μl of PBS/1% BSA. After the blocking step, the wells were washed six times with PBS/0.1% Tween 20™. Fifty microliters of sera, diluted 1:100 in PBS/0.1% Tween 20™/0.1% BSA, was then added to each well and incubated for 30 minutes at room temperature. The plates were then washed six times with PBS/0.1% Tween 20™.

The enzyme conjugate (horseradish peroxidase-Protein A, Zymed, San Francisco, Calif.) was then diluted 1:20,000 in PBS/0.1% Tween 20™/0.1% BSA, and 50 μl of the diluted conjugate was added to each well and incubated for 30 minutes at room temperature. Following incubation, the wells were washed six times with PBS/0.1% Tween 20™. 100 μl of tetramethylbenzidine peroxidase substrate (Kirkegaard and Perry Laboratories, Gaithersburg, Md.) was added, undiluted, and incubated for 15 minutes. The reaction was stopped by the addition of 100 μl of 1N $H_2SO_4$ to each well and the plates were read at 450 nm.

FIG. 2*a* shows the reactivity of the recombinant BMNI-3 and BMNI-6 antigens and the two peptides BABS-1 and BABS-4 in the ELISA assay. The recombinant antigens and the two peptides were negative in ELISA with all seven samples from normal (*B. microti* negative) individuals. In contrast, both BMNI-3 and BMNI-6 detected six of the nine *B. microti*-infected samples, as compared to two out of the nine for the BABS-1 and BABS-4 peptides. This would suggest that BMNI-3 and BMNI-6 may contain other antigenic epitopes in addition to those present in the repeat epitopes in BABS-1 and BABS-4, or that an insufficient number of repeats are available in the peptides to fully express the antigenic epitopes present in the recombinant antigens BMNI-3 and BMNI-6.

Figure 2B:
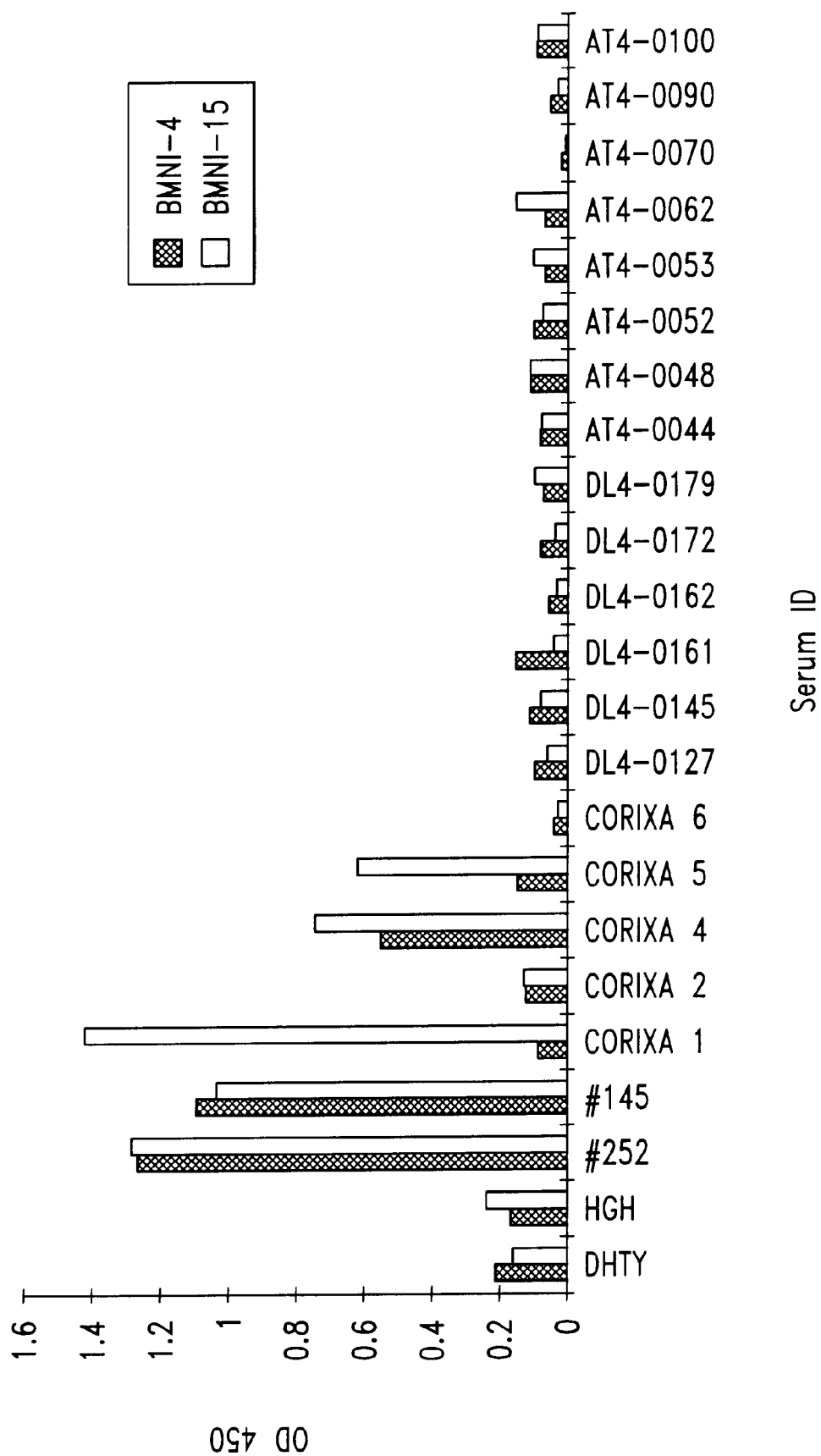
FIG. 2b shows the reactivity of the B. microti antigens BMNI-4 and BMNI-15 with sera from B. microti-infected individuals and from normal donors as determined by ELISA.

FIG. 2*b* shows the ELISA reactivity of the recombinant antigens BMNI-4 and BMNI-15. Both recombinants were negative with all fifteen samples from normal individuals. BMNI-4 detected four out of nine *B. microti*-infected samples and BMNI-15 detected six out of nine *B. microti*-infected samples Both BMNI-4 and BMNI-15 detected a *B. microti*-infected sample which was not detected by BMNI-3 or BMNI-6, suggesting that BMNI-4 and BMNI-15 might be complementary to BMNI-3 and BMNI-6 in the ELISA test described herein.

The ELISA reactivity of recombinant MN-10 and BMNI-20 with sera from *B. microti*-infected patients and from normal donors is shown in FIG. 3. MN-10 and BMNI-20 were found to be reactive with *B. microti*-infected sera that were not reactive with recombinant BMNI-2 through BMNI-17. Therefore, MN-10 and BMNI-20 may be usefully employed in combination with other *B. microti* antigens of the present invention for the detection of *B. microti* infection.

B. Diagnostic Properties of Representative Antigens and Peptides as Determined By Western Analysis Western blot analyses were performed on representative *B. microti* antigens as follows.

Antigens were induced as pBluescript SK-constructs (Stratagene), with 2 mM IPTG for three hours (T3), after which the resulting proteins from time 0 (T0) and T3 were separated by SDS-PAGE on 15% gels. Separated proteins were then transferred to nitrocellulose and blocked for 1 hr in 0.1% Tween 20™/PBS. Blots were then washed 3 times in 0.1% Tween 20™/PBS and incubated with a *B. microti* patient serum pool (1:200) for a period of 2 hours. After washing blots in 0.1% Tween 20™/PBS 3 times, immunocomplexes were detected by the addition of Protein A conjugated to $^{125}I$ (1/25000; NEN-Dupont, Billerica, Mass.) followed by exposure to X-ray film (Kodak XAR 5; Eastman Kodak Co., Rochester, N.Y.) at −70° C. for 1 day.

Figure 4:
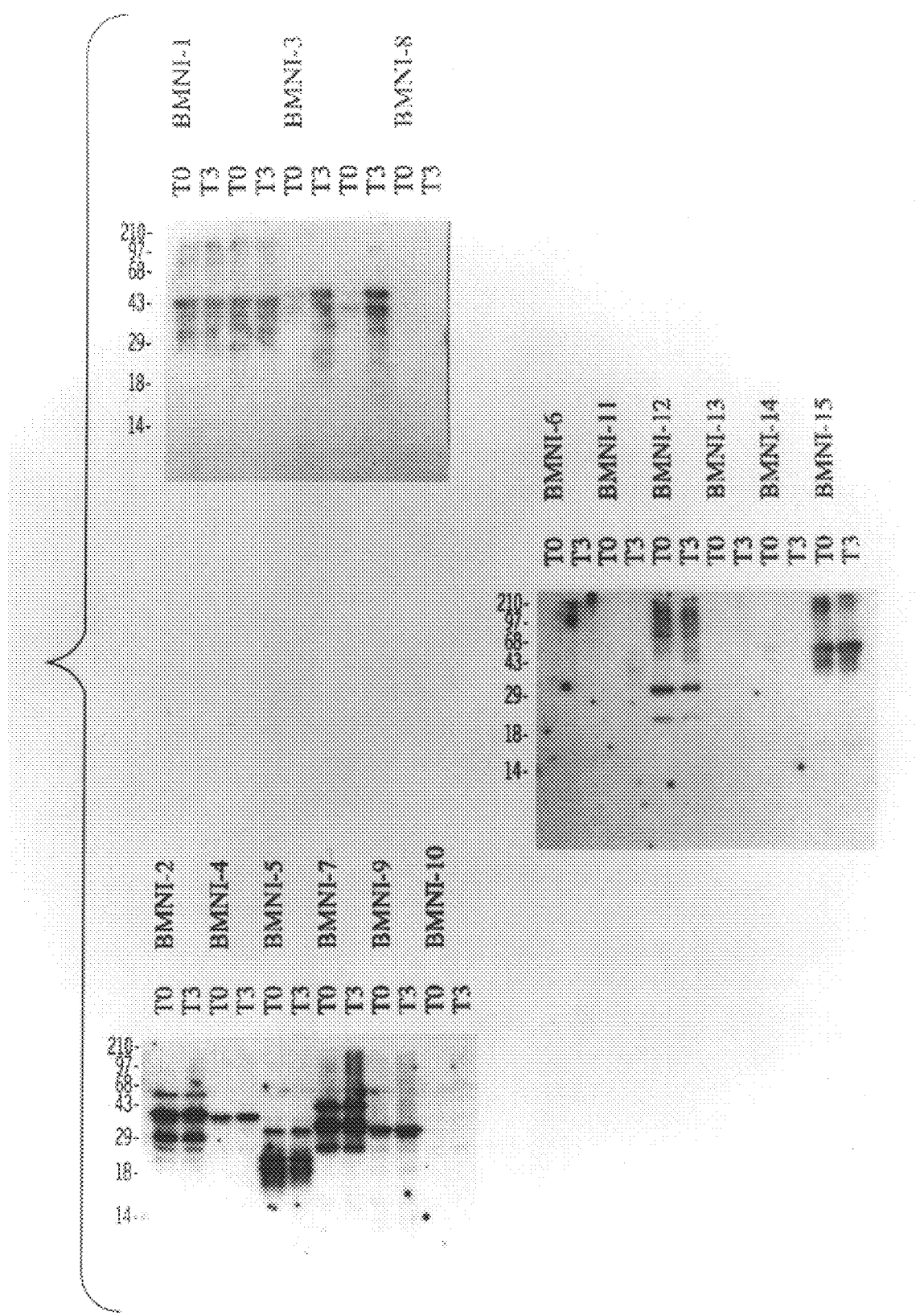
FIG. 4 shows the results of Western blot analysis of representative B. microti antigens of the present invention.

As shown in FIG. 4, resulting bands of reactivity with serum antibody were seen at 43 kDa for BMNI-1, 38 kDa for BMNI-2, 45 kDa for BMNI-3, 37 kDa for BMNI-4, 18 and 20 kDa for BMNI-5, 35 and 43 kDa for BMNI-7, 32 kDa for BMNI-9, 38 kDa for BMNI-11, 30 kDa for BMNI-12, 45 kDa for BMNI-15, and 43 kDa for BMNI-17 (not shown). Antigen BMNI-6, after reengineering as a pET 17b construct (Novagen, Madison, Wis.) showed a band of reactivity at 33 kDa (data not shown). Protein size standards, in kDa (Gibco BRL, Gaithersburg, MB), are shown to the left of the blots.

Western blots were performed on purified BMNI-3 recombinant antigen with a series of patient sera from B. microti patients and from patients with either Lyme disease or ehrlichiosis. Specifically, purified BMNI-3 (4 μg) was separated by SDS-PAGE on 12% gels. Protein was then transferred to nitrocellulose membrane for immunoblot analysis. The membrane was first blocked with PBS containing 1% Tween 20™ for 2 hours. Membranes were then cut into strips and incubated with individual sera (1/500) for two hours. The strips were washed 3 times in PBS/0.1% Tween 20™ containing 0.5 M NaCl prior to incubating with Protein A-horseradish peroxidase conjugate (1/20,000) in PBS/0.1% Tween 20™/0.5 M NaCl for 45 minutes. After further washing three times in PBS/0.1% Tween 20™/0.5 M NaCl, ECL chemiluminescent substrate (Amersham, Arlington Heights, Ill.) was added for 1 min. Strips were then reassembled and exposed to Hyperfilm ECL (Amersham) for 5–30 seconds.

Figure 5:
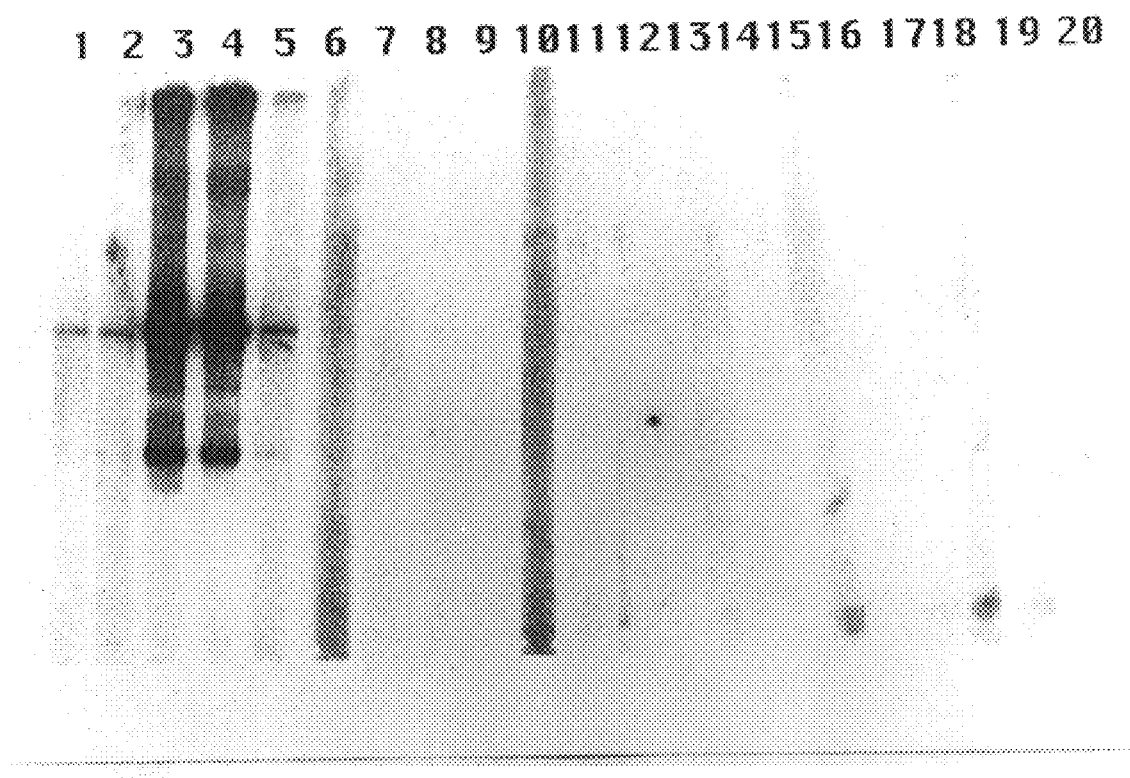
FIG. 5 shows the reactivity of purified recombinant B. microti antigen BMNI-3 with sera from B. microti-infected patients, Lyme disease-infected patients, ehrlichiosis-infected patients and normal donors as determined by Western blot analysis.

Lanes 1–9 of FIG. 5 show the reactivity of purified recombinant BMNI-3 with sera from nine B. microti-infected patients, of which five were clearly positive and a further two were low positives detectable at higher exposure to the hyperfilm ECL. This correlates with the reactivity as determined by ELISA. In contrast, no immunoreactivity was seen with sera from patients with either ehrlichiosis (lanes 10 and 11) or Lyme disease (lanes 12–14), or with sera from normal individuals (lanes 15–20). A major reactive band appeared at 45 kDa and a small break down band was seen at approximately 25 kDa.

Although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated polypeptide comprising an immunogenic portion of a *B. microti* antigen, wherein the polypeptide comprises SEQ ID NO: 52, or an immunogenic portion thereof.

2. The polypeptide of claim 1, produced by expression of a recombinant DNA sequence comprising SEQ ID NO: 50 or a portion thereof.

3. A fusion protein comprising a polypeptide according to claim 1.

4. A fission protein comprising at least one polypeptide according to claim 1 and at least one antigenic epitope comprising an amino acid sequence selected from the group consisting of:

(a) the sequence $-X_1-X_2-X_3-X_4-X_5-Ser-$, wherein $X_1$ is Glu or Gly, $X_2$ is Ala or Thr, $X_3$ is Gly or Val, $X_4$ is Trp or Gly and $X_5$ is Pro or Ser;

(b) SEQ ID NO: 36; and (c) SEQ ID NO: 39.

5. A method for detecting *B. microti* infection in a patient, comprising:

(a) obtaining a biological sample from the patient;

(b) contacting the sample with at least one polypeptide according to claim 1, and (c) detecting the presence of antibodies that bind to the polypeptide, thereby indicating the presence of *B. microti* infection.

6. A method for detecting *B. microti* infection in a patient, comprising:

(a) obtaining a biological sample from a patient;

(b) contacting the sample with at least one polypeptide according to claim 1 and at least one antigenic epitope comprising an amino acid sequence selected from the group consisting of: (i) the sequence $-X_1-X_2-X_3-X_4-X_5-Ser-$, wherein $X_1$ is Glu or Gly, $X_2$ is Ala or Thr, $X_3$ is Gly or Val, $X_4$ is Trp or Gly and $X_5$ is Pro or Ser; (ii) SEQ ID NO: 36 and (iii) SEQ ID NO: 39; and (c) detecting the presence of antibodies that bind to the polypeptide or antigenic epitope, thereby indicating the presence of *B. microti* infection.

7. A method for detecting *B. microti* infection in a patient, comprising:

(a) obtaining a biological sample from the patient;

(b) contacting the sample with a fusion protein according to any one of claims 3 and 4; and (c) detecting the presence of antibodies that bind to the fusion protein, thereby indicating the presence of *B. microti* infection.

8. The method of claims 5, 6 or 7, wherein the biological sample is selected from the group consisting of whole blood, serum, plasma, saliva, cerebrosphinal fluid and urine.

9. The method of claim 5, wherein the polypeptide is bound to a solid support.

10. The method of claim 7, wherein the fusion protein is bound to a solid support.

11. The method of claims 9 or 10, wherein the solid support comprises a material selected from the group consisting of nitrocellulose, latex and plastics.

* * * * *

UNITED STATES PATENT AND TRADEMARK OFFICE
CERTIFICATE OF CORRECTION

PATENT NO.     : 6,183,976 B1                                              Page 1 of 1
DATED          : February 6, 2001
INVENTOR(S)    : Steven G. Reed et al.

It is certified that error appears in the above-identified patent and that said Letters Patent is hereby corrected as shown below:

Title page,
Item [75], Inventors, "Steven G. Reed, Bellevue; Michael J. Lodes, Seattle; Raymond Houghton, Bothel; Paul R. Sleath, Seattle, all of WA (US)" should read as -- Steven G. Reed, Bellevue; Michael J. Lodes, Seattle; Raymond Houghton, Bothel, all of WA (US) --.

Column 115,
Line 30, "A fission protein" should read -- A fusion protein --.
Line 45, "according to claim 1, and" should read -- according to claim 1; and --.

Signed and Sealed this

Twenty-ninth Day of July, 2003

JAMES E. ROGAN
*Director of the United States Patent and Trademark Office*